US012708355B2

(12) United States Patent
Coleman et al.

(10) Patent No.: US 12,708,355 B2
(45) Date of Patent: Aug. 18, 2026

(54) WOUND CLOSURE AND TISSUE COUPLING SYSTEMS AND METHODS

(71) Applicant: Vasorum Ltd., Dublin (IE)

(72) Inventors: James E. Coleman, Dublin (IE); John P. Healy, County Meath (IE)

(73) Assignee: Vasorum Ltd., Dublin (IE)

( * ) Notice: Subject to any disclaimer, the term of this patent is extended or adjusted under 35 U.S.C. 154(b) by 488 days.

(21) Appl. No.: 18/087,559

(22) Filed: Dec. 22, 2022

(65) Prior Publication Data

US 2023/0380837 A1 Nov. 30, 2023

Related U.S. Application Data

(60) Provisional application No. 63/346,151, filed on May 26, 2022.

(51) Int. Cl.
*A61B 17/11* (2006.01)
*A61B 17/00* (2006.01)

(52) U.S. Cl.
CPC *A61B 17/0057* (2013.01); *A61B 2017/00606* (2013.01); *A61B 2017/00623* (2013.01); *A61B 2017/00654* (2013.01); *A61B 2017/00672* (2013.01); *A61B 2017/1107* (2013.01); *A61B 17/1114* (2013.01); *A61B 2017/1132* (2013.01)

(58) Field of Classification Search
CPC ........ A61B 17/0057; A61B 2017/1132; A61B 2017/00606; A61B 2017/00623; A61B 2017/00654; A61B 17/1114; A61B 2017/1107; A61B 2017/00672
See application file for complete search history.

(56) References Cited

U.S. PATENT DOCUMENTS

| | | | |
|---|---|---|---|
| 5,676,689 A | 10/1997 | Kensey et al. | |
| 7,998,174 B2 | 8/2011 | Malandain et al. | |
| 8,007,521 B2 | 8/2011 | Malandain et al. | |
| 8,034,080 B2 | 10/2011 | Malandain et al. | |
| 8,038,698 B2 | 10/2011 | Vandervelde et al. | |
| 8,097,018 B2 | 1/2012 | Malandain et al. | |
| 8,100,943 B2 | 1/2012 | Malandain et al. | |
| 2002/0022822 A1 | 2/2002 | Cragg et al. | |
| 2002/0062104 A1 | 5/2002 | Ashby et al. | |
| 2005/0070935 A1* | 3/2005 | Ortiz .................. | A61B 17/1114 606/155 |

(Continued)

FOREIGN PATENT DOCUMENTS

| | | | |
|---|---|---|---|
| EP | 2217155 B1 | 9/2014 | |
| KR | 101426627 B1 | 8/2014 | |
| WO | 2023227947 A2 | 11/2023 | |

*Primary Examiner* — Jing Rui Ou
(74) *Attorney, Agent, or Firm* — Mintz, Levin, Cohn, Ferris, Glovsky and Popeo, P.C.

(57) ABSTRACT

Surgical assemblies and related methods are provided for using an actuator to deploy an coupler configured to close a tissue puncture or natural opening in the body, or to create an anastomosis. The surgical method includes deploying first and second anastomotic couplers within a patient to create anastomoses in the body to aid in the treatment of various ailments. The first coupler is deployed to fluidly join a gall bladder and an ileum, and the second coupler is deployed to fluidly join a proximal ileal loop and a distal ileal loop. Fluid can flow between central lumens of the first and second couplers.

17 Claims, 72 Drawing Sheets

(56) References Cited

U.S. PATENT DOCUMENTS

| | | | | |
|---|---|---|---|---|
| 2005/0085854 | A1 | 4/2005 | Ginn | |
| 2007/0185529 | A1 | 8/2007 | Coleman et al. | |
| 2007/0225807 | A1 | 9/2007 | Phan et al. | |
| 2008/0027433 | A1 | 1/2008 | Kohm et al. | |
| 2008/0051895 | A1 | 2/2008 | Malandain et al. | |
| 2008/0071376 | A1 | 3/2008 | Kohm et al. | |
| 2008/0147101 | A1* | 6/2008 | Ortiz | A61B 17/1114 606/153 |
| 2009/0105733 | A1 | 4/2009 | Coleman et al. | |
| 2009/0281557 | A1* | 11/2009 | Sander | A61B 17/3468 606/151 |
| 2010/0114128 | A1 | 5/2010 | Coleman et al. | |
| 2011/0009901 | A1 | 1/2011 | Holman et al. | |
| 2013/0165963 | A1 | 6/2013 | Coleman et al. | |
| 2015/0142048 | A1 | 5/2015 | Coleman et al. | |
| 2015/0257753 | A1 | 9/2015 | Tang et al. | |
| 2017/0020894 | A1* | 1/2017 | Galli | A61P 25/30 |
| 2017/0360419 | A1 | 12/2017 | Phillips | |
| 2023/0380819 | A1 | 11/2023 | Coleman et al. | |
| 2023/0380836 | A1 | 11/2023 | Coleman et al. | |

* cited by examiner

WOUND CLOSURE AND TISSUE COUPLING SYSTEMS AND METHODS

CROSS-REFERENCE TO RELATED APPLICATIONS

This application claims priority to U.S. Provisional Patent Application No. 63/346,151, filed May 26, 2022 entitled "Wound Closure and Anastomosis Device for Sealing or Anastomosing Hollow Structures," the entire contents of which are hereby expressly incorporated by reference herein.

FIELD

Methods and device for wound closure and creating an anastomosis are provided.

BACKGROUND

Many surgical procedures involve creating punctures in tissue at a surgical site or anastomosing tissue to create an anastomosis, such as a bowel anastomosis or an arterio-venous fistula between an artery and a vein. In the case of fistula formation, the purpose of such a connection is to create either a high flow connection or to create a pathway for blood around an obstruction in a replacement conduit or bypass. The conduit or bypass can generally be a vein, artery, or prosthetic graft.

An anastomosis can be created during a surgical procedure by bringing two vessels or conduits—such as bowel—into direct contact with each other and then joining them with sutures, clips, or other means. The anastomosis can be end-to-end, end-to-side, or side-to-side. When done with blood vessels, the anastomosis is typically elliptical in shape and is joined by hand with a suture. Other methods of anastomosis creation can involve carbon dioxide lasers, prostheses, clips, and stents. One type of fistula, an arterio-venous fistula, is created by connecting an artery to a vein. This type of connection can be used for hemodialysis, an increase in exercise tolerance, the treatment of hypertension, maintenance of an opening in an artery or vein, as an access path for chemotherapy, and others.

Various apparatuses have been proposed for percutaneously sealing tissue openings or for joining hollow structures in a patient's body, including biodegradable plugs, sutures, surgical fasteners, and other devices. However, these devices and associated methods have a multitude of shortcomings, including surgical risks, high failure rates, complexity, and more. Accordingly, there remains a need for improved devices and associated methods for closing tissue punctures and anastomosing tissue structures in a patient's body, or for deploying such devices in a simple and effective manner.

SUMMARY

In general, methods and systems for creating an anastomosis and wound closure are provided.

In one embodiment, a surgical assembly is provided and includes an actuator assembly having an elongate shaft including an outer shaft and an inner shaft concentrically disposed within the outer shaft to define a fluid flow path there between, and a deployable coupler coupled to a distal end of the outer shaft. The deployable coupler can have a plurality of proximal and distal slits formed therein and can be configured to form proximal and distal wing. The proximal and distal slits can be configured to allow blood to flow therethrough into the fluid flow path to a fluid outlet port formed in the actuator assembly.

The surgical assembly can vary in a number of ways and may include any of the following features, alone or in combination. For example, the actuator assembly can include a handle operably coupled to the deployable coupler. In some aspects, the handle can include an actuator rotatable in a first direction to cause deployment of the distal wing and rotatable in a second direction to cause deployment of the proximal wing. In another aspect, the handle can include a deployment lever configured to decouple the deployable coupler from the distal end of the outer shaft. For example, the surgical assembly can include a delivery sheath configured to couple to the actuator assembly. The delivery sheath can define a central lumen configured to receive the elongate shaft. For example, a distal end of the outer shaft can include at least two opposed longitudinal gaps to allow blood to flow from the deployable coupler into the fluid flow path. In some aspects, the outer shaft can include a crown disposed around the at least two opposed longitudinal gaps. In some variations, the crown can include castellations, and the deployable coupler can be coupled to the castellations. For example, each of the slits in the plurality of proximal and distal slits can be substantially s-shaped.

In another embodiment, a surgical method is provided. The surgical method can include inserting an elongate shaft of an actuator assembly through a guide assembly extending through a puncture hole in a body lumen to position a deployable coupler coupled to a distal end of the elongate shaft within the body lumen such that blood flows into the deployable coupler, through the elongate shaft, and out of a port at a proximal end of the actuator assembly. The surgical method can also include subsequently actuating the actuator assembly to cause a distal wing on the deployable coupler to deploy radially outward. The surgical method can further include retracting the actuator assembly to pull the distal wing against an inner wall of the body lumen to cause the blood to stop flowing into the deployable coupler. The surgical method can further include actuating the actuator assembly to cause a proximal wing on the deployable coupler to deploy radially outward adjacent to an outer wall of the body lumen, thereby sealing the puncture hole in the body lumen. The surgical method can further include decoupling the deployable coupler from the distal end of the elongate shaft.

The surgical method can vary in a number of ways and may include any of the following features, alone or in combination. For example, the surgical method can include, subsequent to actuating the actuator to cause the distal wing to deploy radially outward and prior to actuating the actuator assembly to cause the proximal wing to deploy radially outward, pivoting the elongate shaft to position the distal wing relative to the inner wall of the body lumen. For example, the elongate shaft can include an inner shaft and an outer shaft concentrically disposed around the inner shaft, and blood can flow between the inner shaft and the outer shaft. In some aspects, a distal end of the outer shaft can include a pair of welded C-tubes defining gaps through which blood flows. For example, deployment of the proximal wing can include rotating the actuator assembly in a first direction. In some aspects, deployment of the distal wing can include rotating the actuator assembly in a second direction opposite the first direction.

In another embodiment, a surgical assembly is provided. The surgical assembly can include an actuator assembly including an elongate shaft a deployable coupler coupled to a distal end of the elongate shaft. The deployable coupler can include a plurality of proximal slits therein configured to form a set of proximal wing and a plurality of distal slits therein configured to form a set of distal wing. The actuator assembly can be configured to transform the deployable coupler from a delivery configuration in which the proximal wing and the distal wing are substantially parallel to the elongate shaft to a fully-deployed configuration in which one of the proximal and distal wings is substantially perpendicular to the elongate shaft and the other one of the proximal and distal wings is skew to the elongate shaft.

The surgical assembly can vary in a number of ways and may include any of the following features, alone or in combination. For example, each of the plurality of proximal slits can include first and second cuts having substantially equal lengths. The substantially equal lengths can cause the proximal wing to be substantially perpendicular to the elongate shaft in the deployed configuration. For example, each of the plurality of distal slits can include first and second cuts having substantially unequal lengths. The substantially unequal lengths can cause the distal wing to be substantially skew to the elongate shaft in the deployed configuration. For example, transformation of the deployable coupler from the delivery configuration to the deployed configuration can cause the proximal wing and the distal wing to fold about mid regions thereof. For example, the plurality of proximal slits and the plurality of distal slits can be substantially s-shaped. For example, the surgical assembly can include a secondary handle configured to couple to a proximal end of the actuator assembly. The secondary handle can have a distally extending plug configured to be passed through a central lumen at least partially defined by the elongate shaft and to be positioned within a central bore of the deployable coupler. In some aspects, the distally extending plug can be configured to seal the central bore.

In another embodiment, a surgical assembly is provided. The surgical assembly can include a delivery tool including an elongate shaft extending from a distal end thereof, and a deployable coupler coupled to a distal end of the elongate shaft. The deployable coupler can have proximal wing defined by first proximal and distal cuts and distal wing defined by second proximal and distal cuts. The delivery tool can be configured to transform the deployable coupler between a delivery configuration in which the elongate shaft is substantially parallel to the first and second wing and a deployed configuration in which the elongate shaft is substantially transverse to the first and second wing. A deployment angle of the proximal wing can be at least partially defined by a length ratio of the first proximal and distal cuts and a deployment angle of the distal wing can be at least partially defined by a length ratio of the second proximal and distal cuts.

The surgical assembly can vary in a number of ways and may include any of the following features, alone or in combination. For example, the length ratio of the first proximal and distal cuts can be substantially equal to 1 and can be configured to cause the deployment angle of the first wing to be approximately 90 degrees. For example, the length ratio of the second proximal and distal cuts can be substantially greater than 1 and can be configured to cause the deployment angle of the second wing to be substantially acute.

In another embodiment, a surgical coupler is provided. The surgical coupler can include a first tubular portion having a first plurality of longitudinal cuts, a second tubular portion having a second plurality of longitudinal cuts, and a connector portion disposed between the first and central tubular portions. Each of the longitudinal cuts in the first plurality of longitudinal cuts can have a proximal cut and a distal cut having a length ratio of approximately 1:1. Each of the longitudinal cuts in the second plurality of longitudinal cuts can have a proximal cut and a distal cut having a length ratio substantially less than 1:1. The first and second tubular portions and the connector portion can define a central lumen.

The surgical coupler can vary in a number of ways and may include any of the following features, alone or in combination. For example, the first tubular portion can be configured to reversibly form a wing that is substantially perpendicular to a longitudinal axis of the central lumen. For example, the second tubular portion can be configured to reversibly form a wing that is substantially skew to a longitudinal axis of the central lumen. For example, the connector portion can have a diameter that is greater than a diameter of the first tubular portion and a diameter of the second tubular portion. In some aspects, the diameter of the first tubular portion can be less than the diameter of the second tubular portion. For example, the coupler can be configured to couple with an actuator tool. The actuator tool can be configured to reversibly form the first and second tubular portions into wing. In some aspects, the actuator tool can be configured to receive a plug configured to prevent fluid flow the central lumen.

In another embodiment, a method is provided. The method can include inserting a delivery sheath over a guidewire through a puncture in an artery to position a deployable coupler coupled to a distal end of the delivery sheath within the artery. The method can also include pivoting the delivery sheath from an insertion orientation, in which blood can travel up the coupler, to an angled orientation, in which blood is prevented from traveling up the coupler. The method can further include actuating an actuator coupled to a proximal end of the delivery sheath to deploy a distal wing. The distal wing can be positioned within the artery adjacent to the puncture. The method can further include actuating the actuator to deploy a proximal wing on the deployable coupler such that the proximal wing are positioned outside of the artery adjacent to the puncture. The method can further include removing the guidewire from the central lumen. The method can further include advancing a plug into the central lumen of the deployable coupler to seal the puncture.

The method can vary in a number of ways and may include any of the following features, alone or in combination. For example, the plug can be operatively coupled to a secondary handle having a deployment lever thereon configured to deploy the plug into the deployable coupler. In some aspects, the method can include, after the plug is advanced into the central lumen, actuating the deployment lever to cause the plug to separate from the secondary handle. For example, the method can further include positioning the coupler relative to a puncture site using an external imaging system, the external imaging system detecting the radiopacity of the coupler.

In another embodiment, a surgical method is provided. The surgical method can include advancing a first coupler through a small intestine to a region of the small intestine proximate a gallbladder. The first coupler can be coupled to a distal end of an elongate shaft. The surgical method can also include piercing the region of the small intestine and the gallbladder using a penetrator advanced through the elongate shaft and the first coupler. The surgical method can further include advancing the first coupler at least partially within the gallbladder. The surgical method can further include deploying first distal wing of the first coupler within the gallbladder. The surgical method can further include retracting the elongate shaft to cause the first distal wing to contact an inner surface of the gallbladder. The surgical method can further include deploying first proximal wing of the first coupler within the small intestine to removably affix the first coupler to the gallbladder and the small intestine. The surgical method can further include ejecting the first coupler from the distal end of the elongate shaft.

The surgical method can vary in a number of ways and may include any of the following features, alone or in combination. For example, the surgical method can include advancing a second coupler through the small intestine into a distal ileal loop proximate a proximal ileal loop. The second coupler can be coupled to the distal end of the elongate shaft. The surgical method can also include piercing through an inner wall of the distal ileal loop to enter the proximal ileal loop using the penetrator advanced through the elongate shaft and the second coupler. The surgical method can further include deploying second distal wing of the second coupler within the proximal ileal loop. The surgical method can further include retracting the elongate shaft to cause the second distal wing to contact an inner surface of the proximal ileal loop. The surgical method can further include deploying second proximal wing of the second coupler within the distal ileal loop to removably affix the second coupler to the proximal ileal loop and the distal ileal loop. The surgical method can further include ejecting the second coupler from the distal end of the elongate shaft. For example, at least one of the first proximal wing and the first distal wing can deploy at an acute angle relative to a longitudinal axis of the elongate shaft. In some aspects, the other of the first proximal wing and the first distal wing can deploy at an acute angle relative to a longitudinal axis of the elongate shaft. In other aspects, a radial tip of the first proximal wing, in a deployed configuration, can contact an inner wall of the small intestine and a radial tip of the first distal wing, in a deployed configuration, contacts an inner wall of the gallbladder. For example, an angle of deployment of the first proximal wing and an angle of deployment of the first distal wing can be substantially equal. A length of the first proximal wing and a length of the first distal wing can be substantially equal. For example, the first proximal wing can include a first plurality of petals and the first distal wing can include a second plurality of petals. The first plurality of petals can be rotatably offset from the second plurality of petals.

In another embodiment, a method is provided. The method can include deploying, via an actuator tool having an elongate shaft and a first coupler coupled to a distal end of the elongate shaft, first distal wing of the first coupler within a gallbladder and first proximal wing of the first coupler within an ileum. The method can also include deploying, via the actuator tool having a second coupler coupled to the distal end, second distal wing of the second coupler within a first loop of the ileum distal to the deployed first coupler, and second proximal wing of the second coupler within a second loop of the ileum proximal to the deployed first coupler. The first coupler can define a first central lumen configured to fluidly join the gallbladder and the ileum therethrough. The second coupler can define a second central lumen configured to fluidly join the first and second loops therethrough.

The method can vary in a number of ways and may include any of the following features, alone or in combination. For example, the method can include piercing through a wall of the ileum and through a wall of the gall bladder with a penetrator coupled to the distal end of the elongate shaft to position the first coupler at least partially within the gallbladder and at least partially within the ileum. In some aspects, at least one of the first proximal wing and the first distal wing can deploy at an acute angle relative to a longitudinal axis of the elongate shaft. In some variations, the other of the first proximal wing and the first distal wing can deploy at an acute angle relative to a longitudinal axis of the elongate shaft. In other variations, a radial tip of the first proximal wing, in a deployed configuration, can contact an inner wall of the small intestine in and a radial tip of the first distal wing, in a deployed configuration, can contact an inner wall of the gallbladder. In other aspects, the angle of deployment of the first proximal wing and the angle of deployment of the first distal wing can be substantially equal. The length of the first proximal wing and the length of the first distal wing can be substantially equal. In further aspects, the first proximal wing can include a first plurality of petals and the first distal wing can include a second plurality of petals. The first plurality of petals can be rotatably offset from the second plurality of petals.

In another embodiment, a method is provided. The method can include introducing a first coupler into an ileum. The first coupler can be attached to an elongate shaft extending distally from an actuator tool. The first coupler and the elongate shaft can define a first central lumen therethrough. The method can also include contacting an outer wall of the ileum adjacent an outer wall of a gallbladder with a distal end of the first coupler. The method can further include extending a first penetrator through the first central lumen to pierce the inner wall of the ileum and the outer wall of the gallbladder. The method can further include advancing the first coupler from the ileum and into the gallbladder. The method can further include deploying, with the actuator tool, distal wing of the first coupler within the gallbladder. The method can further include retracting the first coupler to contact an inner wall of the gallbladder with the distal wing. The method can further include deploying, with the actuator tool, proximal wing of the first coupler within the ileum. The gallbladder and the ileum can be in fluid communication via the first coupler. The method can further include de-coupling the first coupler from the elongate shaft.

The method can vary in a number of ways and may include any of the following features, alone or in combination. For example, the method can include introducing a second coupler into a distal ileal loop distal of the first coupler. The second coupler can be attached to the elongate shaft. The second coupler and the elongate shaft can define a second central lumen therethrough. The method can also include incising a region of a proximal ileal loop proximal of the first coupler. The method can further include contacting an outer wall of the distal ileal loop adjacent the incised region of the proximal ileal loop. The method can further include extending a second penetrator through the second central lumen to pierce the inner wall of the distal ileal loop and the incised region. The method can further include advancing the second coupler from the distal ileal loop into the proximal ileal loop through the incised region. The method can further include deploying, with the actuator tool, distal wing of the second coupler within the proximal ileal loop. The method can further include retracting the second coupler to contact an inner wall of the proximal ileal loop with the distal wing. The method can further include deploying, with the actuator tool, proximal wing of the second coupler within the distal ileal loop. The proximal and distal ileal loops can be in fluid communication via the second coupler. The method can further include de-coupling the second coupler from the elongate shaft.

In another embodiment, a method is provided, including inserting a sheath through an ileum and into a gallbladder, advancing an expandable coupler coupled to a distal end of an actuator tool through the sheath and into the gallbladder, retracting the sheath from the gallbladder to expose the expandable coupler, deploying, with the actuator tool, a distal wing of the expandable coupler within the gallbladder, deploying, with the actuator tool, a proximal wing of the expandable coupler within the ileum, and de-coupling the expandable coupler from the actuator tool. The gallbladder and the ileum can be in fluid communication via the deployed expandable coupler.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

These and other features will be more readily understood from the following detailed description taken in conjunction with the accompanying drawings, in which.

Figure 1:
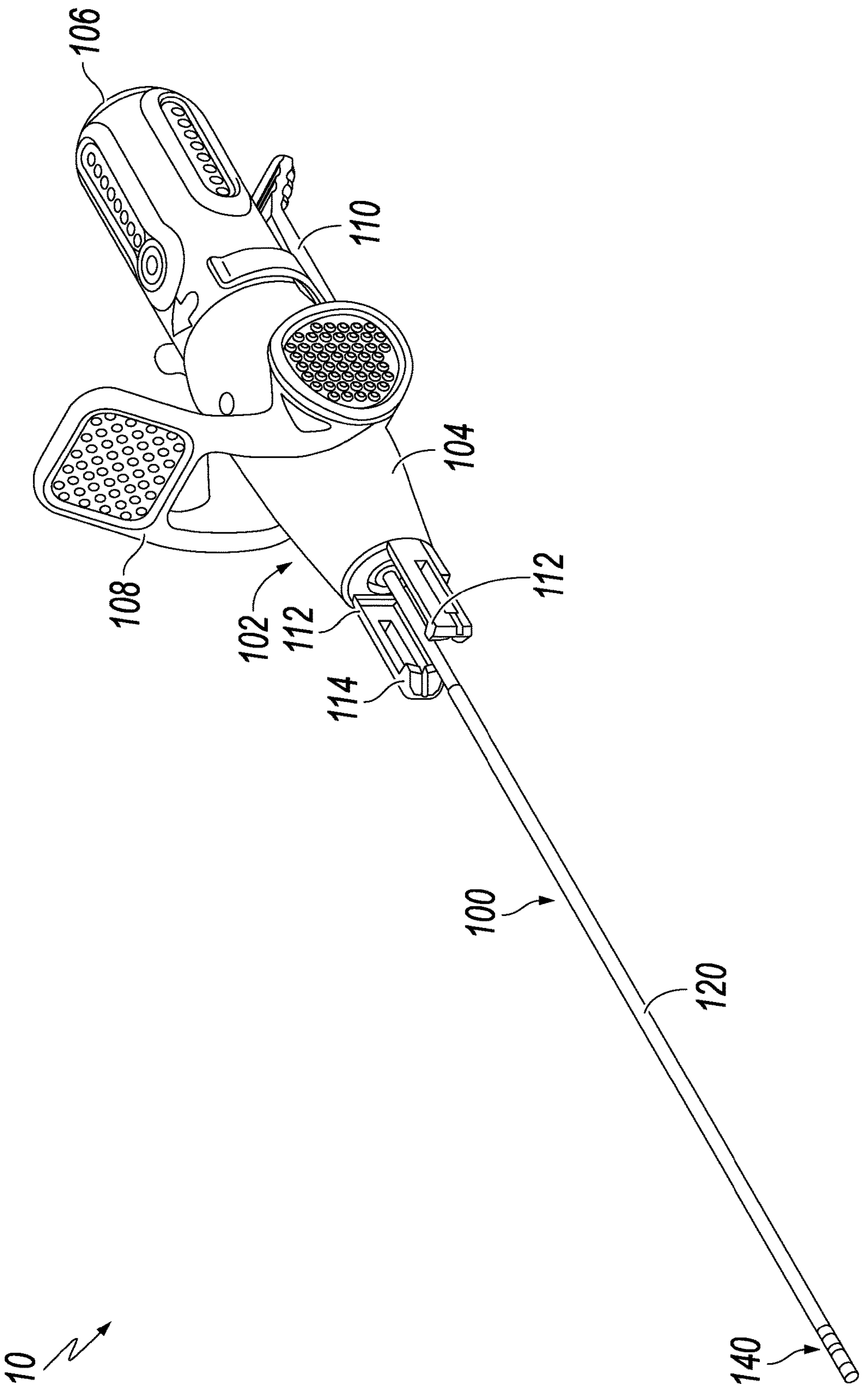
FIG. 1 is a perspective view of a portion of a closure assembly including an actuator assembly according to an embodiment.

It is noted that the drawings are not necessarily to scale. The drawings are intended to depict only typical aspects of the subject matter disclosed herein, and therefore should not be considered as limiting the scope of the disclosure.

DETAILED DESCRIPTION

Certain illustrative embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting illustrative embodiments and that the scope of the present invention is defined solely by the claims. The features illustrated or described in connection with one illustrative embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape.

Surgical assemblies for use with anastomotic couplers and closure couplers are provided. In general, the surgical assembly can include an actuator device configured to deploy an anastomotic coupler within a patient to join and fluidly link tissue. The actuator device can include a handle having an elongate shaft extending distally therefrom. A distal end of the elongate shaft can have an anastomotic coupler affixed thereto, and the handle can be actuated to cause the affixed coupler to reversibly deploy one or more proximal and/or distal wing to couple the tissue therebetween. The coupler can then be decoupled from the elongate shaft. In the case of the closure coupler, prior to deployment of the one or more proximal and/or distal wing, the surgical assembly can employ a blood signal, which can be used to determine a position and/or orientation of the coupler relative to tissue in order to ensure proper deployment of the coupler. Depending upon the position of the coupler, blood can flow through the coupler and up the elongate shaft to provide a surgeon with a visual indicator of the position of the coupler.

In certain embodiments, the coupler can have a large, centrally disposed bore. The bore can facilitate fluid flow between joined regions of tissue, as may be needed for various surgical procedures. When fluid flow through the coupler is not desired, a plug can be advanced through the actuator device and into the large bore. The plug can then be permanently or reversibly affixed to the large bore to prevent fluid flow therethrough.

The closure assembly can be used in various surgical procedures. For example, the closure assembly can be used for the percutaneous closure of the common femoral arteriotomy or venotomy following diagnostic and/or interventional therapeutic intra-arterial procedures, such as peripheral or coronary angiography, arterial stents, balloon angioplasty, and atherectomy procedures where the arteriotomy is in the common femoral artery and closure assemblies have been used. Further, the closure assembly can be used in additional procedures, including, for example, in procedures promoting weight loss and/or the treatment of Type-2 diabetes.

Figure 2:
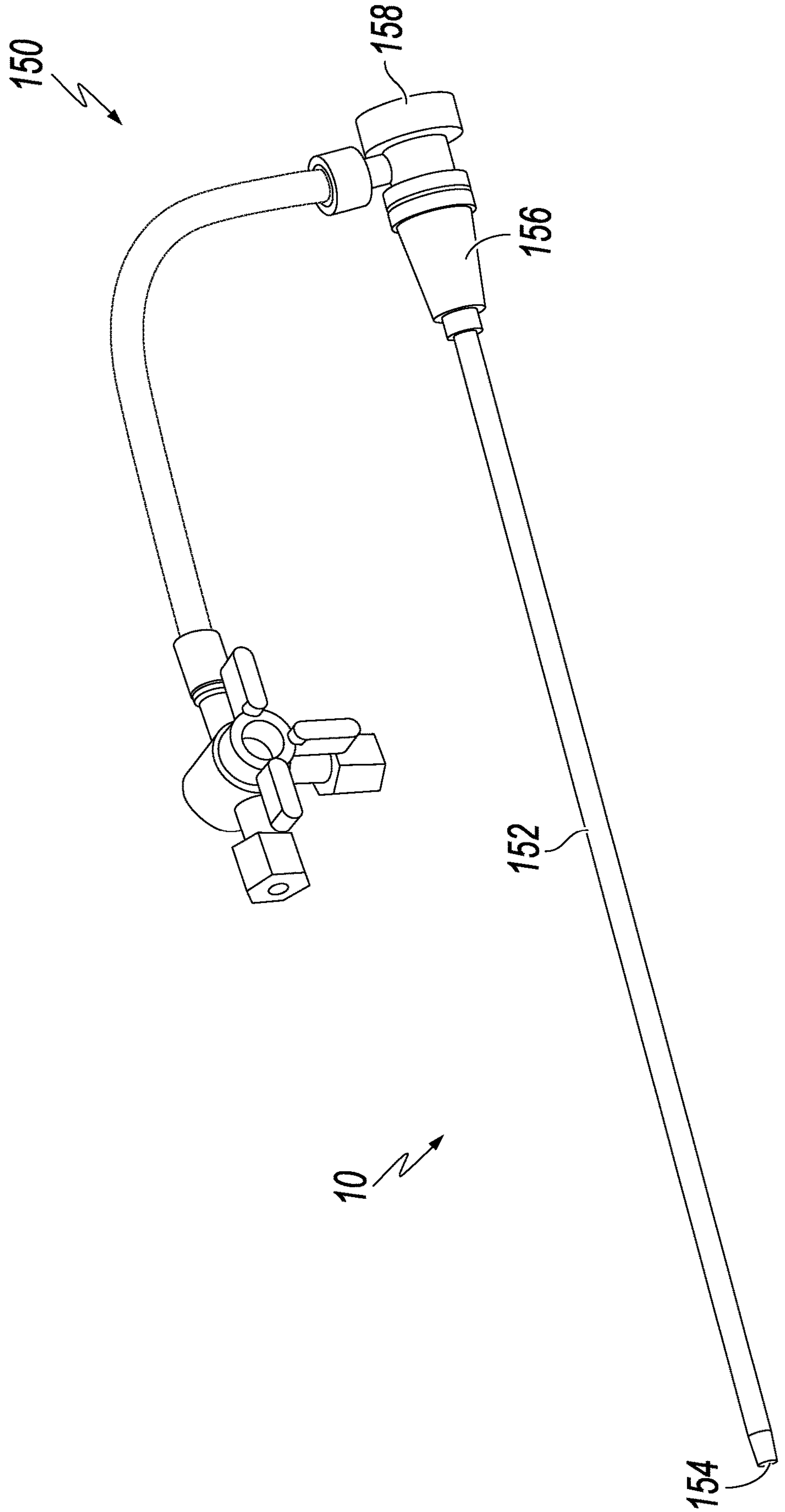
FIG. 2 is a perspective view of an introducer assembly of the closure assembly of FIG. 1.

FIGS. 1 and 2 illustrate an embodiment of a closure assembly 10. The illustrated closure assembly 10 includes an actuator assembly 100, a deployable coupler 140, and an introducer sheath 150. The actuator assembly 100 is configured to be manipulated in order to reversibly transform the deployable coupler 140 from a delivery configuration to a deployed configuration in order to close tissue or couple tissue, and then to eject the deployable coupler 140 from the actuator assembly 100 once the deployable coupler 140 is in a desired location. The deployable coupler 140 can join the tissue and can also provide a fluid pathway between the joined tissue, as will be described in greater detail below. The closure assembly 10 can be used with various introducer sheath 150 sizes.

The actuator assembly 100 can include a proximal actuator 102 and a distal flexible guide tube 120 extending therefrom. The proximal actuator 102 can include a substantially cylindrical body 104 with a proximal handle 106 rotatably coupled thereto. The proximal handle 106 can be rotated in either a first or a second direction (e.g., clockwise and counter-clockwise) to reversibly deploy one or more portions of the deployable coupler 140, depending upon the needs of a surgical procedure. An ejection lever 108 can extend outward and upward from the cylindrical body 104 and can be pivoted relative thereto. Actuation of the ejection lever 108 can cause the proximal actuator 102 to eject the deployable coupler 140. In order to prevent premature actuation of the proximal handle 106, a removable locking tab 110 can be affixed to the cylindrical body 104 and the proximal handle 106. The removable locking tab 110 can rotatably fix the proximal handle 106 relative to the cylindrical body 104. The removable locking tab can affix to both the cylindrical body 104 and the proximal handle 106 via one or more protrusions and/or recesses found on an underside of the proximal actuator 102 (not shown). The removable locking tab 110 can further wrap around the proximal handle 106 to be secured to the proximal actuator 102 until removal by an operator. An operator can remove the removable locking tab 110 from the cylindrical body 104 and the proximal handle 106, and then the operator can actuate the proximal handle 106 and/or the ejection lever 108 as desired. The proximal actuator 102 can include information for guiding a user through a surgical procedure. For example, arrows can be included on the proximal actuator 102 indicating an actuation direction and order for use during a surgical procedure, i.e., an arrow marked "1" pointing in a first direction to indicate that the proximal handle 106 should first be turned in that direction, and an arrow marked "2" pointing in a second direction to indicate that the proximal handle 106 should next be turned in that direction.

Figure 5:
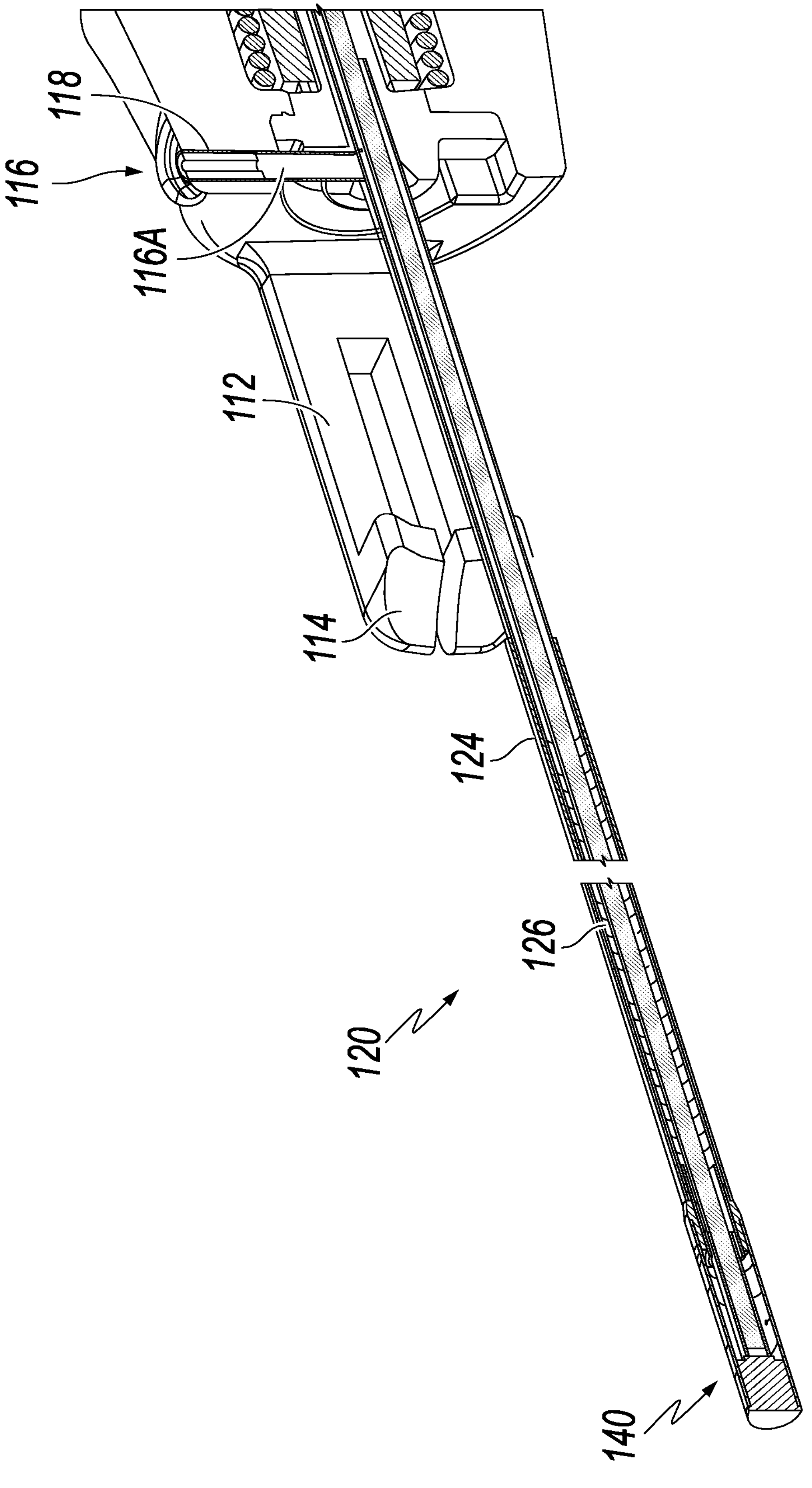
FIG. 5 is a partial-cross sectional view of the closure assembly of FIG. 1.
Figure 6:
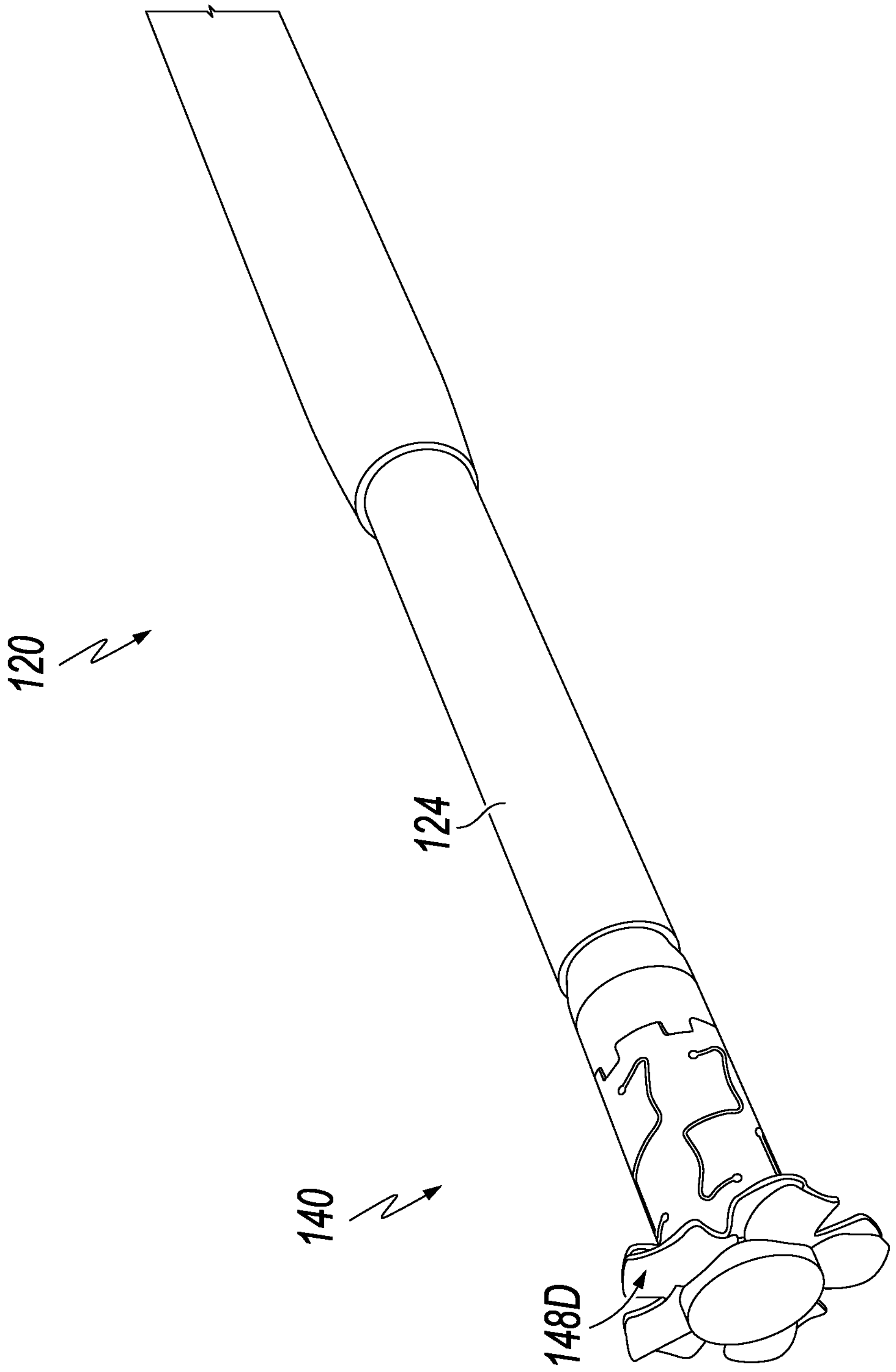
FIG. 6 is a perspective view of the deployable coupler of FIG. 4 having a deployed distal wing.
Figure 7:
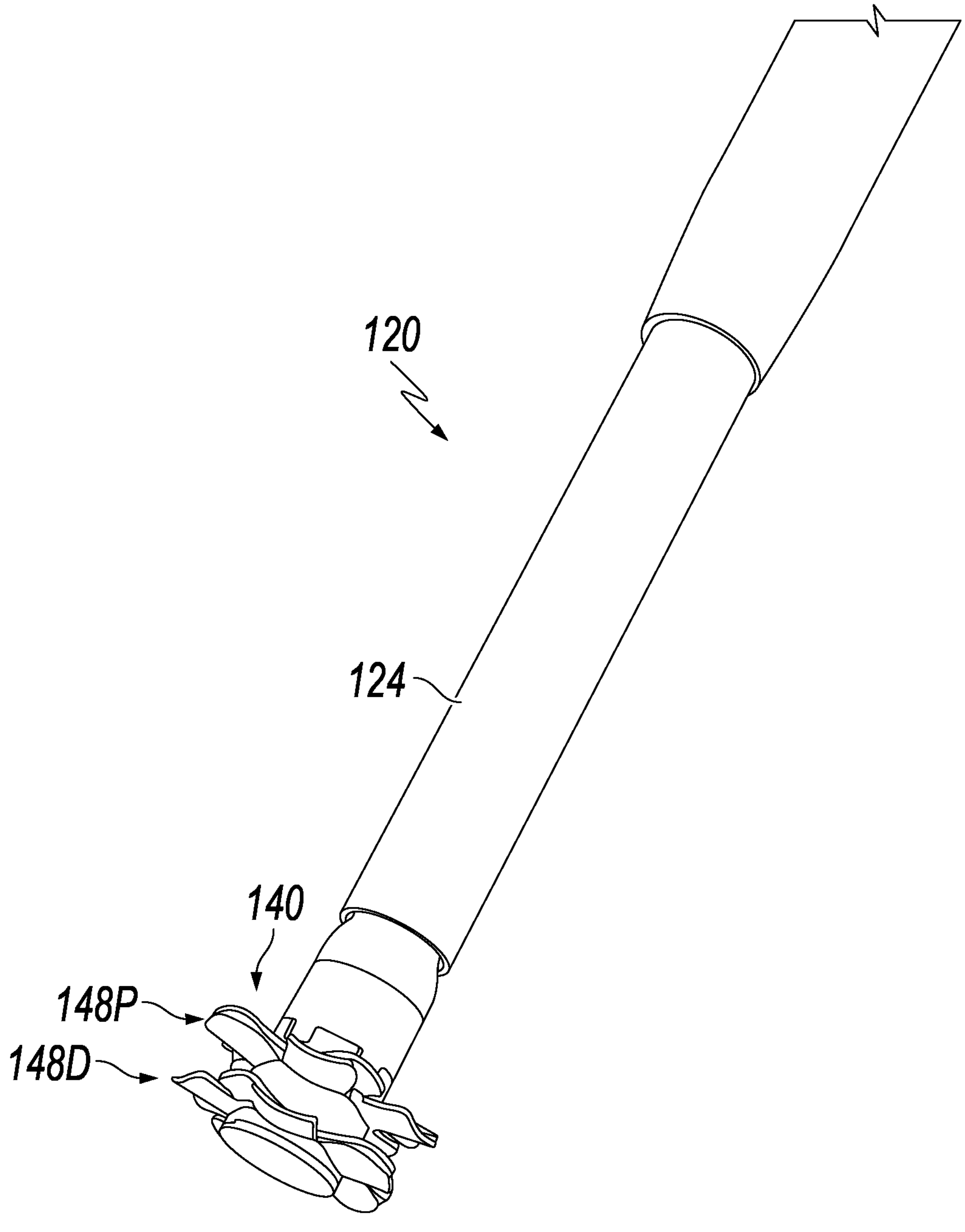
FIG. 7 is a perspective view of the deployable coupler of FIG. 4 having deployed distal and proximal wing.
Figure 8:
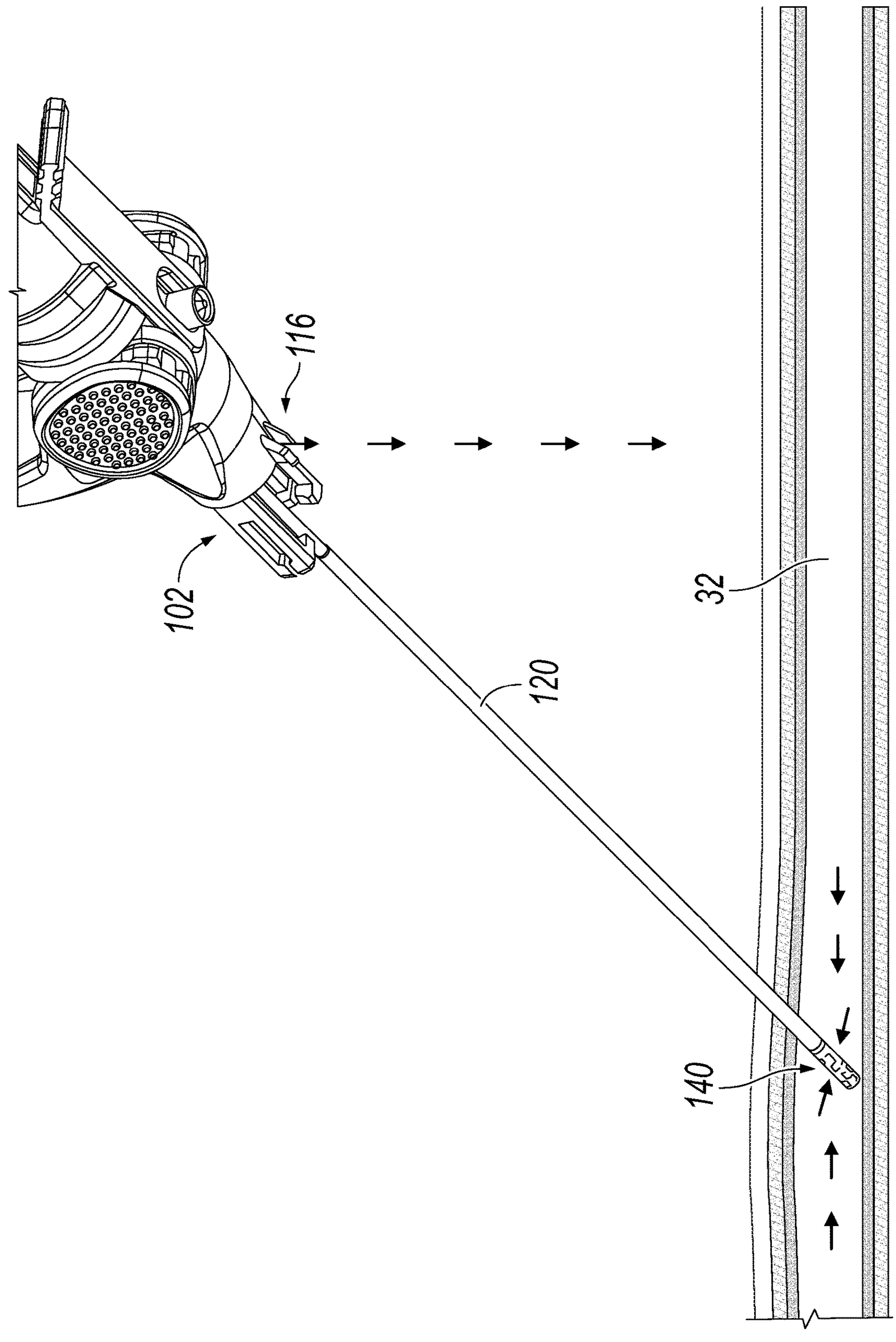
FIG. 8 is a partial perspective view of the closure assembly of FIG. 1 with the deployable coupler inserted into an arterial lumen.
Figure 9:
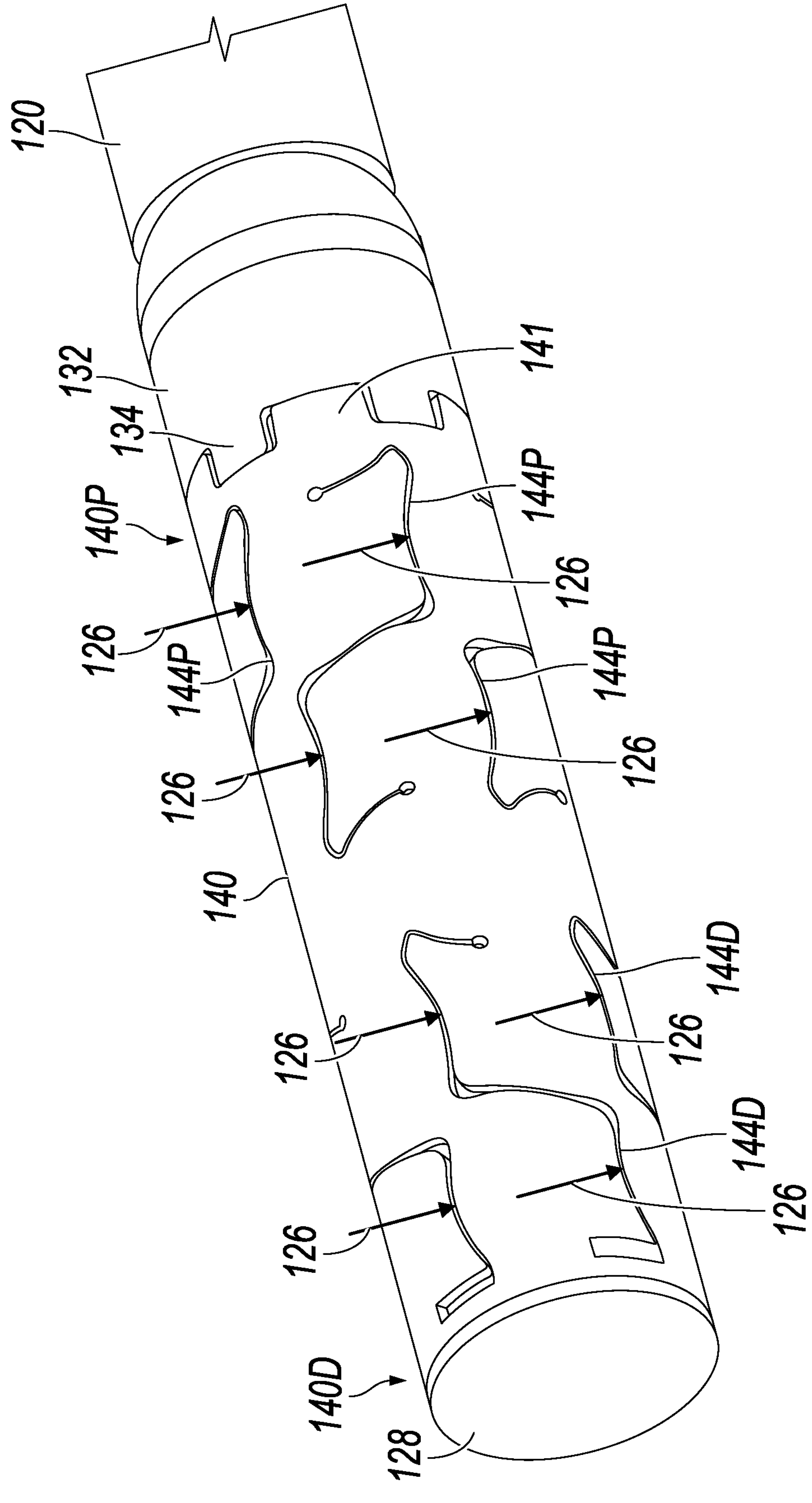
FIG. 9 is a perspective view of the distal end of the flexible guide tube of FIG. 4 with blood flowing through the deployable coupler.

A pair of sheath latches 112 can extend from the distal side of the cylindrical body 104. The sheath latches 112 can take on various forms and arrangements, but they can generally be a single or pair of opposed, linear prongs with inward-facing ends 114 configured to grip and retain the introducer sheath 150, as will be described in greater detail below. A blood signal outlet 116 can be located on the upper side of the cylindrical body 104, as shown in FIG. 5, or at any other location around the circumference of the cylindrical body 104. The blood signal outlet 116 can include a central hole 116A leading to an inner flow path configured to be in fluid communication with a patient's body. The blood signal outlet 116 can also include one or more horns 118 or a collar or tubing, etc. extending downward from the cylindrical body 104. Blood signals and the blood signal outlet 116 in operation will be described in greater detail below.

Figure 3:
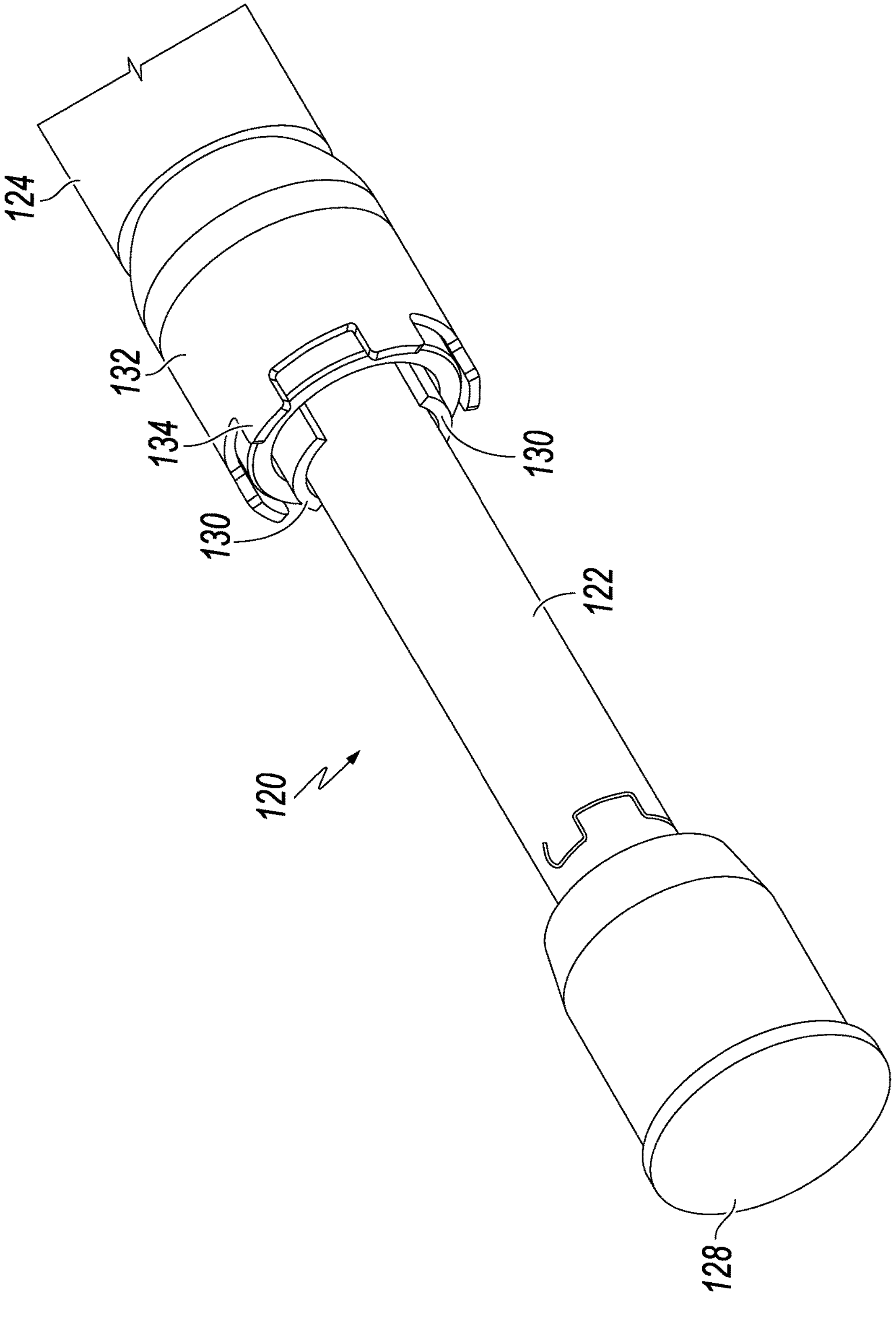
FIG. 3 is a perspective view of the distal end of a flexible guide tube of the closure assembly of FIG. 1, without an anastomotic coupler attached thereon.

The flexible guide tube 120 extends distally from the cylindrical body 104, between the sheath latches 112, and it can be substantially linear in form. In some variations, the flexible guide tube 120 can be rigid in structure. The flexible guide tube 120 can include a central dowel 122 surrounded by an outer sheath 124 to define a flow path 126 in a space between the central dowel 122 and the outer sheath 124. The flow path 126 can run the entire length of the flexible guide tube 120. The central dowel 122 can include a distal end cap 128 that flares outward, as shown in greater detail in FIG. 3. The outer sheath 124 can have a length less than a length of the central dowel 122 such that the deployable coupler 140 can be positioned around a portion of the central dowel 122 extending beyond the distal end of the outer sheath 124. The outer sheath 124 can include a pair of opposed extensions 130 with gaps therebetween, thereby forming a c-tube. The distal portion of the outer sheath 124 can further include a retainer 132 disposed around the c-tube portion of the outer sheath 124, and this retainer 132 can include a plurality of castellations 134 thereon.

Figure 4:
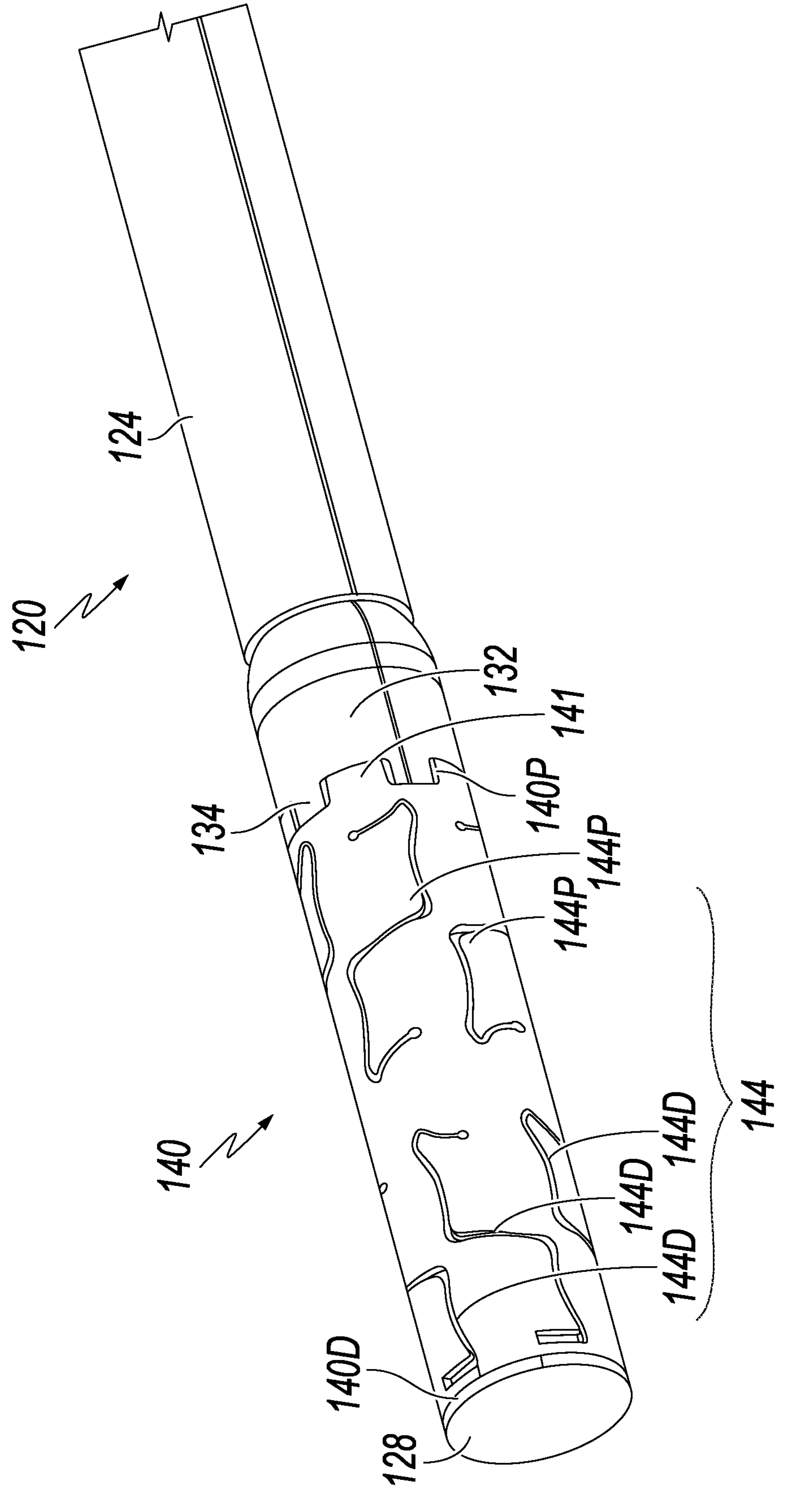
FIG. 4 is a perspective view of the distal end of the flexible or rigid guide tube of FIG. 3 with an deployable coupler attached thereon.

FIG. 4 illustrates a close-up view of the flexible guide tube 120 with a seated deployable coupler 140, and FIG. 5 provides a cross-sectional view of the flexible guide tube 120 having the seated deployable coupler 140 affixed thereon. The seated deployable coupler 140 can be substantially cylindrical, defining a central lumen configured to receive the central dowel 122 of the flexible guide tube 120 when seated thereon. The seated deployable coupler 140 can be made of various materials, including various metals, plastics, or combinations thereof. Specific materials can include stainless steel, titanium, or any biocompatible material(s). The seated deployable coupler 140 can include a proximal end with a complimentary castellation pattern 141 capable of meshing with the castellations 134 on the retainer 132. The seated deployable coupler 140 can also include a plurality of slits 144, located on a proximal end 140P and a distal end 140D. Proximal slits 144P and distal slits 144D can take on a variety of forms, and can be, for example, linear, curved, irregular, etc. In some variations, the slits 144 can be substantially a mirror image of each other and are substantially s-shaped or z-shaped or similar, as shown, for example, in FIG. 4. The slits 144 can also be sized to provide a gap large enough for blood to flow through and into the flexible guide tube 120, as will be described in greater detail below.

The seated deployable coupler 140 can reversibly transform between a delivery configuration and a deployed configuration. In the delivery configuration, the seated deployable coupler 140 can have a substantially linear formation, as shown, for example, in FIGS. 1 and 4 when the seated deployable coupler 140 is seated on the flexible guide tube 120. Transformation of the seated deployable coupler 140 to the deployed configuration can occur by actuating the proximal handle 106 to cause it to rotate in either the first direction and the second direction in sequence. Rotation of the proximal handle 106 in the first direction can cause both a torsional force and a compressive force to be applied to the seated deployable coupler 140, as discussed below, resulting in deployment of one or more wing. In the substantially-linear delivery configuration, the seated deployable coupler 140 can have a substantially uniform diameter along its length, while in the substantially-expanded, deployed configuration, the seated deployable coupler 140 transforms to have at least one proximal wing and at least one distal wing configured to retain tissue therebetween.

Transformation between the delivery configuration and the deployed configuration can occur via actuation of the proximal handle 106. During the transformation process, the proximal handle 106 can be rotated in a first direction to cause the outer sheath 124 of the flexible guide tube 120 to rotate as well. Rotation of the flexible guide tube 120 can result in the meshed castellations of both the retainer 132 and the seated deployable coupler 140 undergoing a torsional force. The meshed castellations 134, 141 of the both the retainer 132 and the seated deployable coupler 140 can cause the outer sheath 124 to apply a torsional force to the seated deployable coupler 140. Simultaneously, a linear compressive force can be applied to the seated deployable coupler 140 in a proximal direction, originating with the distal end cap 128. For example, the proximal handle 106 can be rotated in a first direction (e.g., clockwise or counter-clockwise) to rotate the end cap 128 in the first direction to torque and then compress the seated deployable coupler 140 and cause the distal end 140D to splay radially outward, thereby forming a distal wing 148D. When the deployable coupler 140 is adequately compressed and the distal wing 148D is formed, which occurs via an actuator spring (not shown) coupled to the proximal handle 106 to provide the necessary forces to compress the deployable coupler 140, the proximal wing 148P can be formed. The proximal handle 106 can be rotated in a second direction (which may be the same as or different than the first direction) to further compress the coupler and apply a torque in an opposite direction to cause the proximal end 140P to splay outward, thereby forming a proximal wing 148P. The proximal and distal wings 148P, 148D can have a variety of forms. For example, the wings 148P, 148D may include one or more petals or segments forming the shape of the wings 148P, 148D.

Together, the seated deployable coupler 140 and the proximal actuator 102 can define a blood flow path, which can be used during a surgical procedure as a blood signal to inform a surgeon about the position and/or orientation of the seated deployable coupler 140 within a patient's body. Proper positioning and orientation of the seated deployable coupler 140 can ensure that the wing of the seated deployable coupler 140 are not improperly deployed in a way that could be ineffective or harmful.

Figure 10:
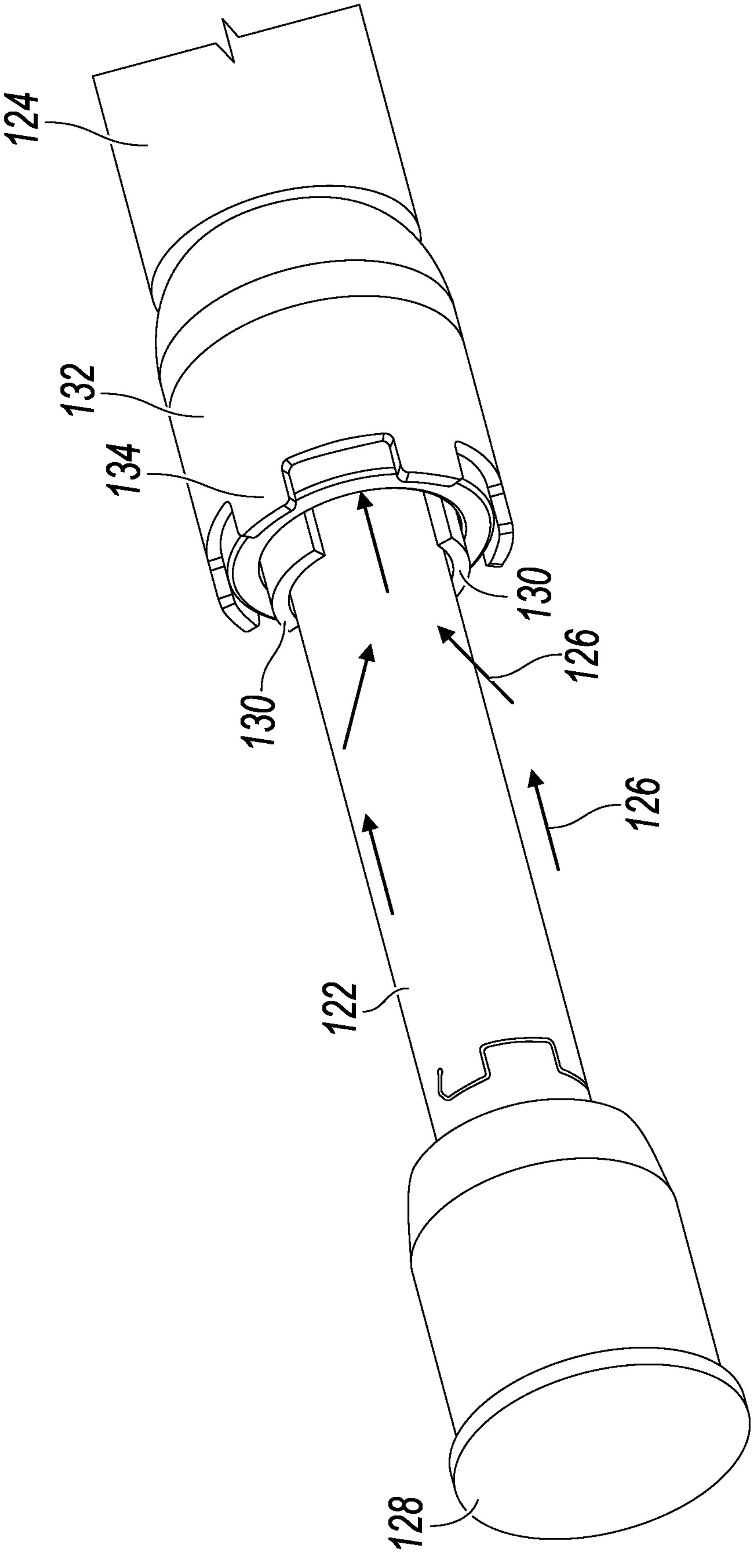
FIG. 10 is a perspective view of the distal end of the flexible guide tube of FIG. 4 with the deployable coupler removed and blood flowing into the flexible guide tube.
Figure 11:
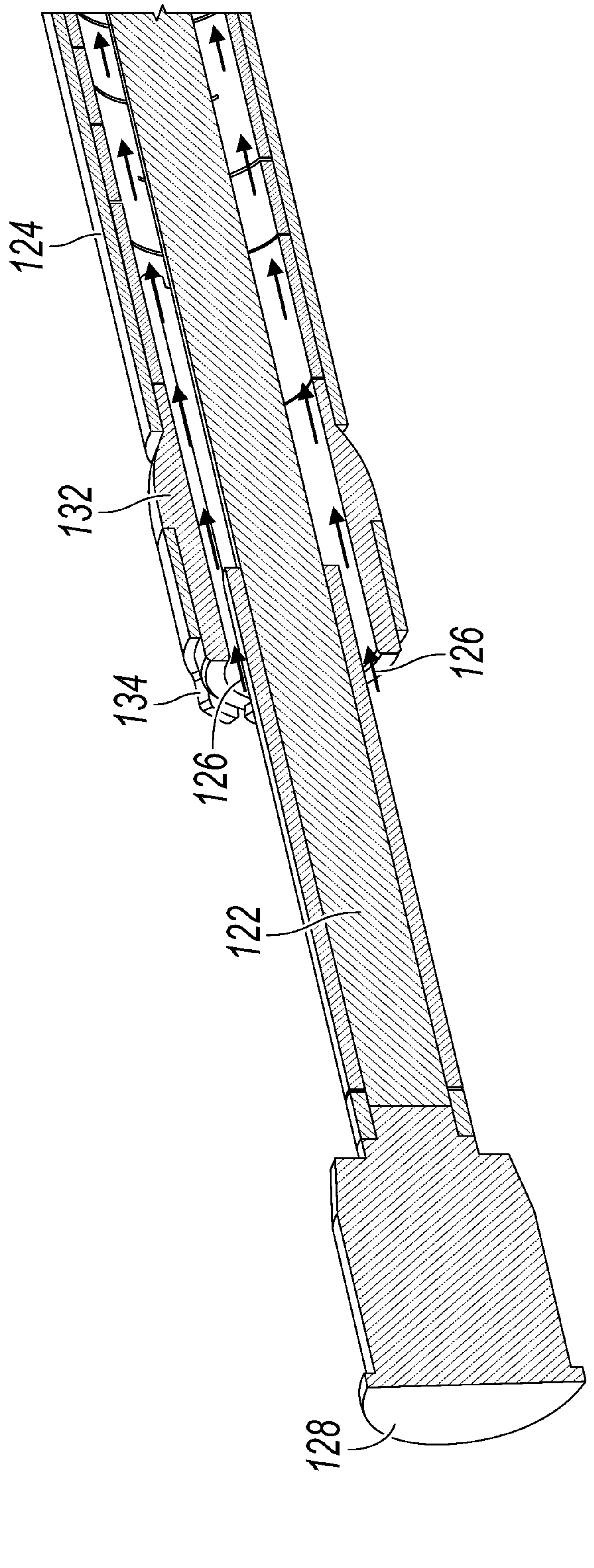
FIG. 11 is a partial cross-sectional view of the flexible guide tube of FIG. 4 with the deployable coupler removed and blood flowing through the flexible guide tube.
Figure 12:
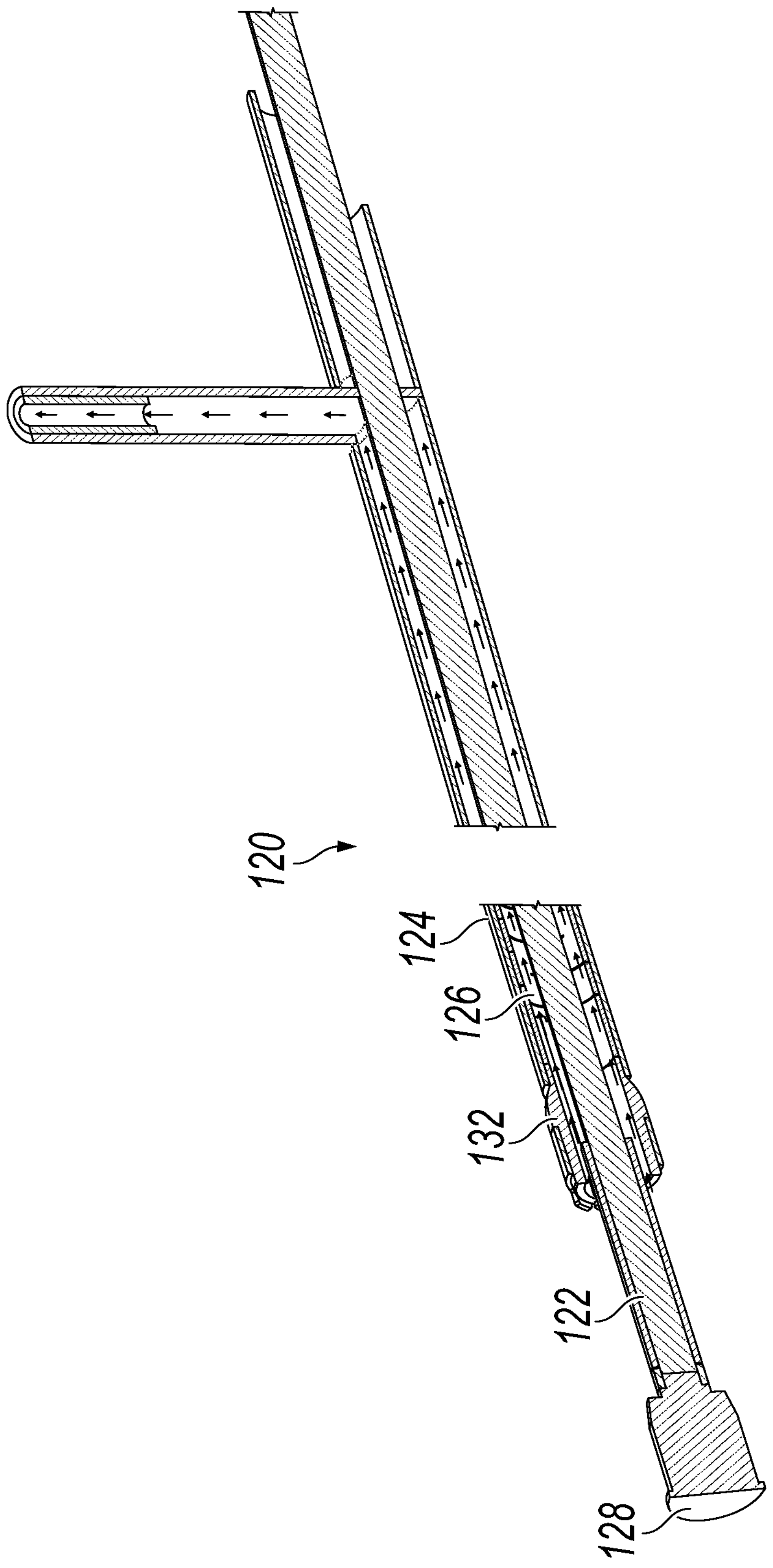
FIG. 12 is a partial cross-sectional view of the flexible guide tube of FIG. 4 including blood flowing through the blood signal outlet.

FIGS. 7-11 illustrate exemplary blood flow through a blood flow path defined by the seated deployable coupler 140 and the proximal actuator 102 during a procedure. Blood within a patient can be driven by a patient's blood pressure to travel into the seated deployable coupler 140 and through the proximal actuator 102 to be emitted from the cylindrical body 104 of the proximal actuator 102 as shown by arrows in FIG. 8. Blood can enter the coupler through the proximal and distal slits and openings 144P, 144D as illustrated by arrows in FIG. 9. Once the blood has entered the seated deployable coupler 140, it can flow through the gaps in the c-tube portion of the outer sheath 124, underneath the retainer 132, as illustrated in FIGS. 10-11. From there, the blood can travel in the space between the central dowel 122 and the outer sheath 124 all the way up the flexible guide tube 120. Eventually, the blood will reach a turning point in which the blood flow path 126 is directed toward the blood signal outlet 116, as illustrated in FIG. 12. The blood can finally be emitted from the blood signal outlet 116, where it can be expelled in a controlled manner.

Referring back to FIG. 2, the introducer sheath 150 can include a substantially elongate sheath 152 having a central lumen 154 sized to receive the flexible guide tube 120 with the seated deployable coupler 140 affixed thereon. The introducer sheath 150 can include a proximal funnel 156 having a flared base 158, which can be received by the sheath latches 112 in order to couple the proximal actuator 102 and the introducer sheath 150 together. The introducer sheath 150 can provide an access pathway for the actuator assembly 102 during a surgical procedure. The introducer sheath 150 can take on various forms and can be, for example, a cannula complete with any or all of the features described herein.

Figure 13:
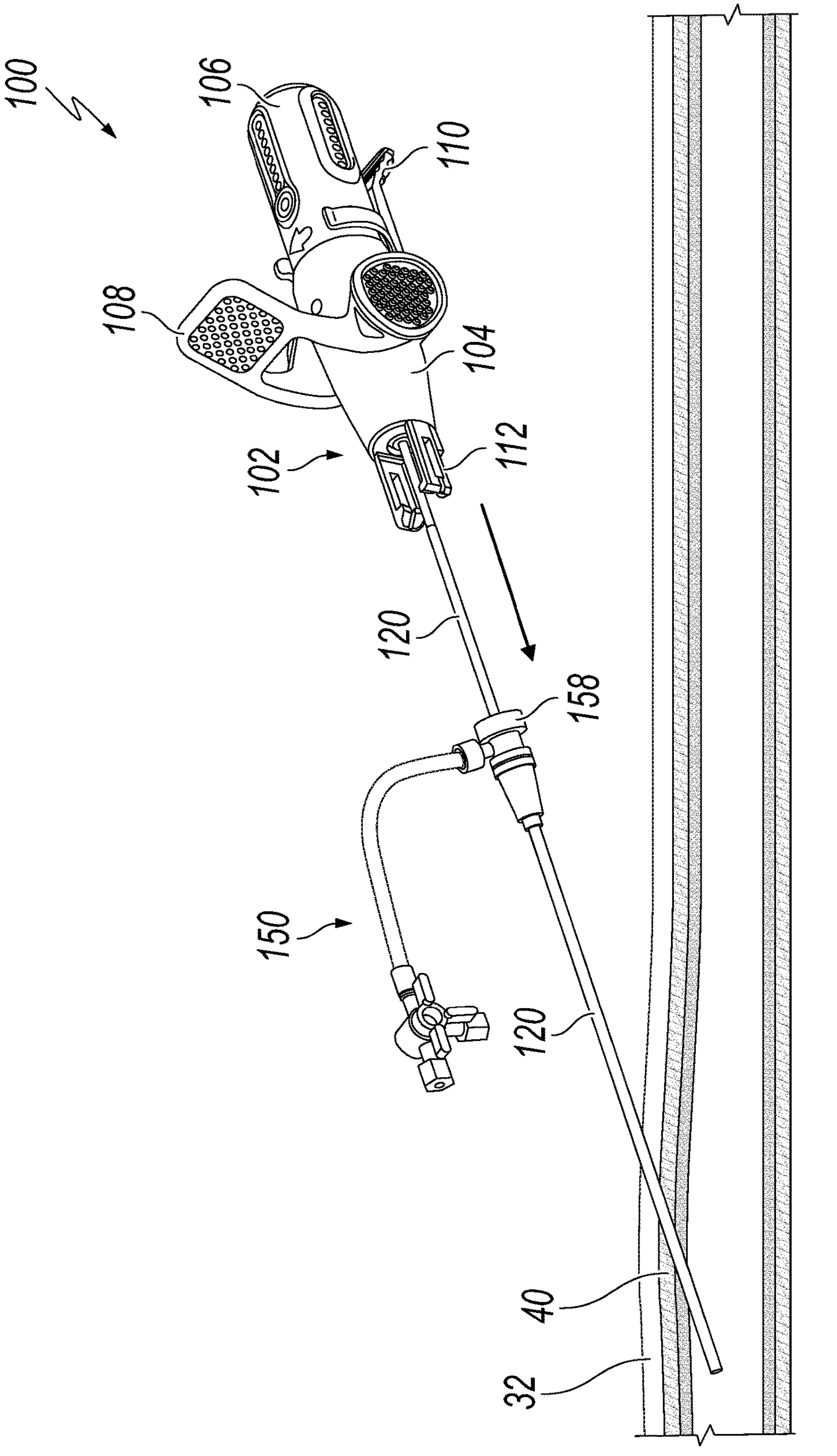
FIG. 13 is a perspective view of the actuator assembly of the closure assembly of FIG. 1 being inserted into the introducer sheath of the closure assembly of FIG. 1, located at least partially within an arterial lumen.
Figure 14:
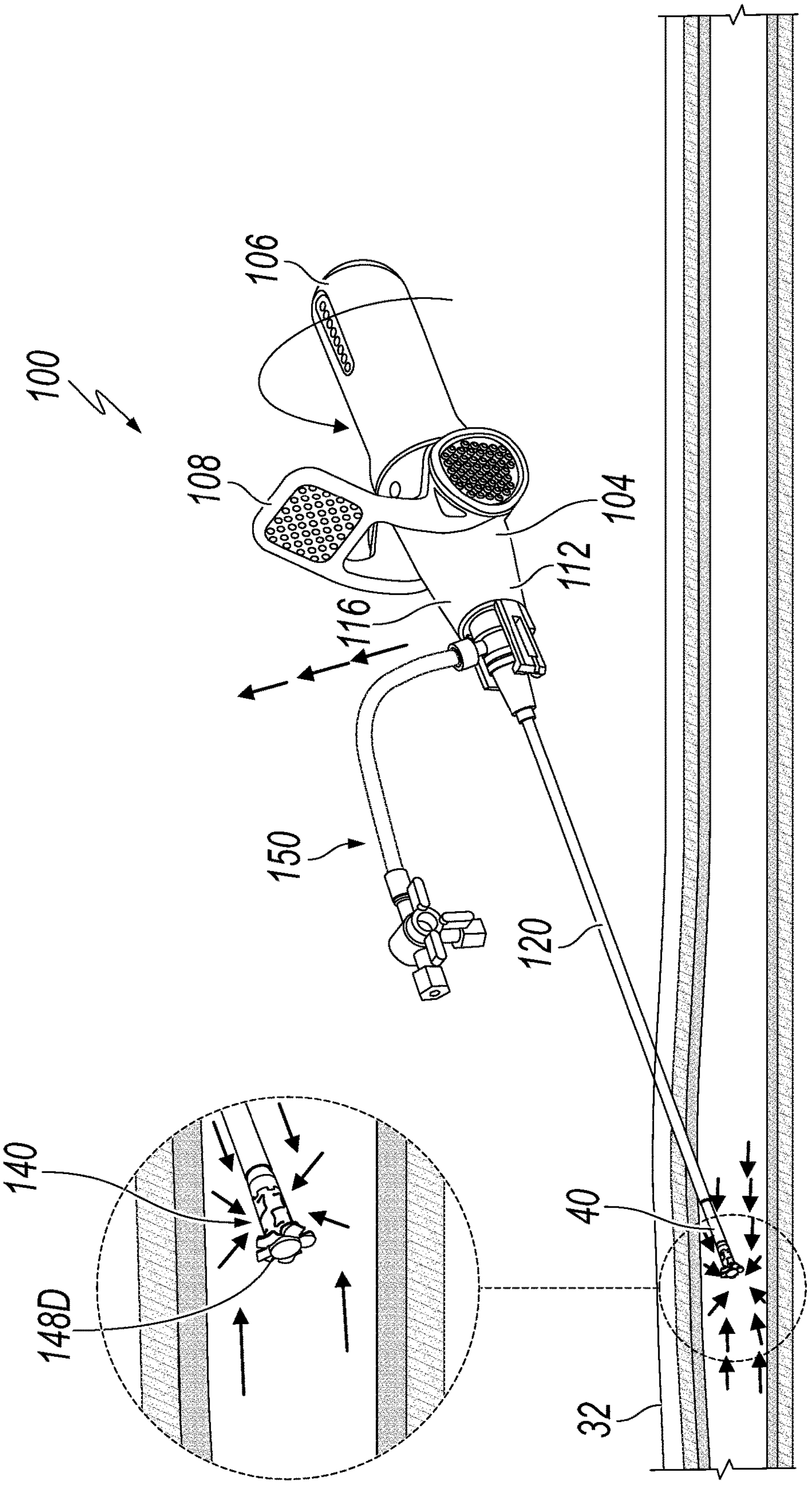
FIG. 14 is a perspective view of the closure assembly of FIG. 13 with the deployable coupler having a deployed distal wing, with an insert highlighting the deployed distal wing.

During an exemplary surgical procedure, shown in FIGS. 13-18, the actuator assembly 100 can be used to join tissue 40 located in an arterial lumen 32. At any or all of the stages of the surgical procedure, positioning, deployment, and more can be confirmed with various imaging techniques before proceeding to the next step, i.e., with fluoroscopy and the like. A prepared introducer sheath 150 can be inserted into the arterial lumen 32 of a patient in order to provide access to a treatment region. As shown in FIG. 13, the flexible guide tube 120 and a deployable coupler 140 can be inserted into the introducer sheath 150 and then advanced until the sheath latches 112 couple the cylindrical body 104 of the proximal actuator 102 to the introducer sheath 150 via the flared base 158. Initially, the angle between a surface of the tissue and the actuator assembly 100 can be shallow (e.g., less than 90 degrees relative to the axis of the lumen, and more preferably less than 45 degrees) so that, during insertion, the deployable coupler 140 does not "bottom out" in the arterial lumen 32, i.e., so that the deployable coupler 140 does not impact an opposite side of the arterial lumen 32 and potentially injure the patient. When the proximal actuator 102 and the deployable coupler 140 are in the proper position, blood can flow into the flexible guide tube 120 via the deployable coupler 140 and then out the blood signal outlet 116. FIG. 14 depicts the blood flow through the deployable coupler 140 and the proximal actuator 102, with close-up views of both the deployable coupler 140 and the upper side of the proximal actuator 102, highlighting the blood signal outlet 116. Once the blood is flowing out of the blood signal outlet 116, the removable locking tab 110 can be detached from the proximal actuator 102.

Figure 15:
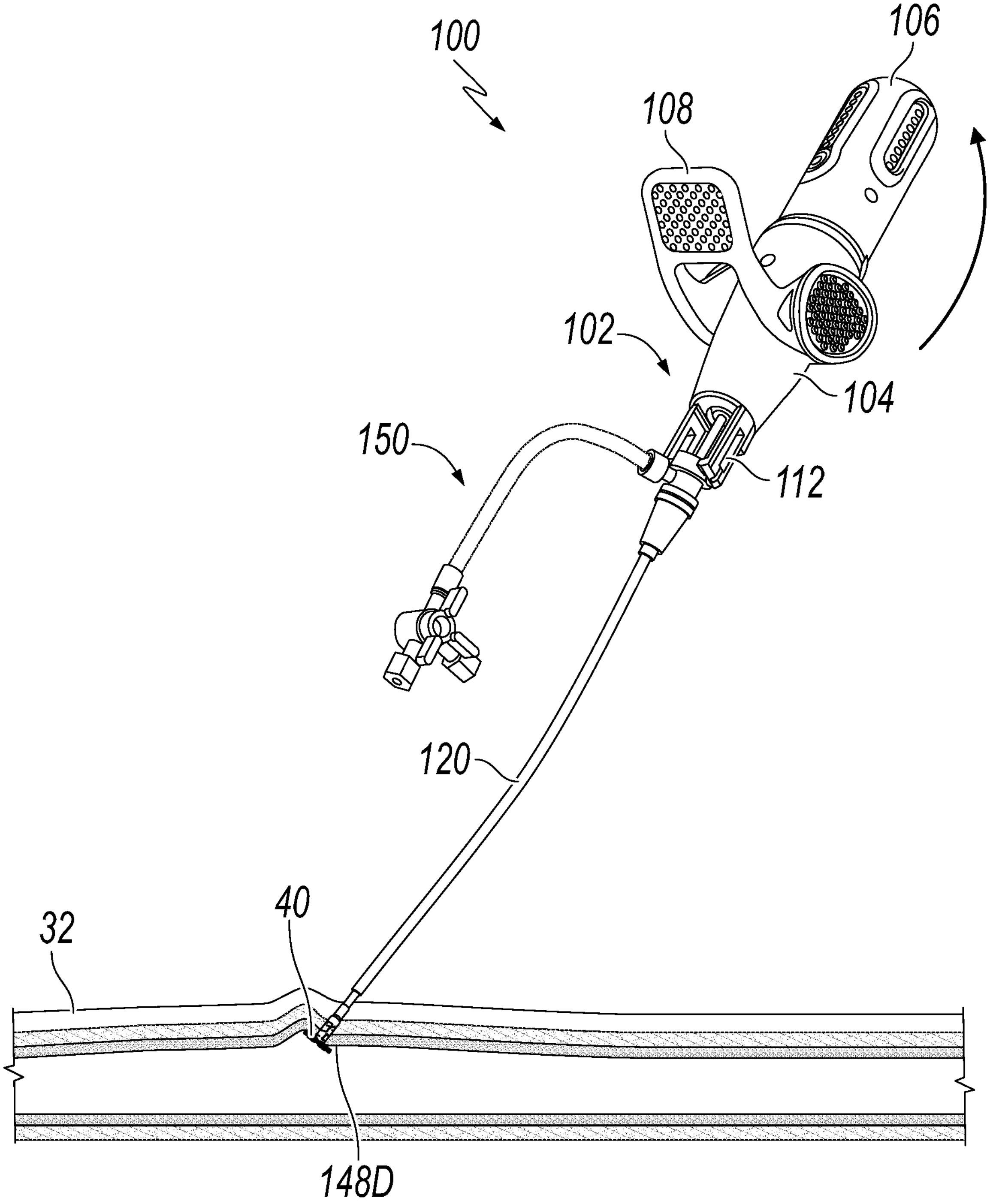
FIG. 15 is a perspective view of the closure assembly of FIG. 13 with the deployed distal wing tensioned against an inner wall of the arterial lumen and the closure assembly being moved to an elevated angle.
Figure 16:
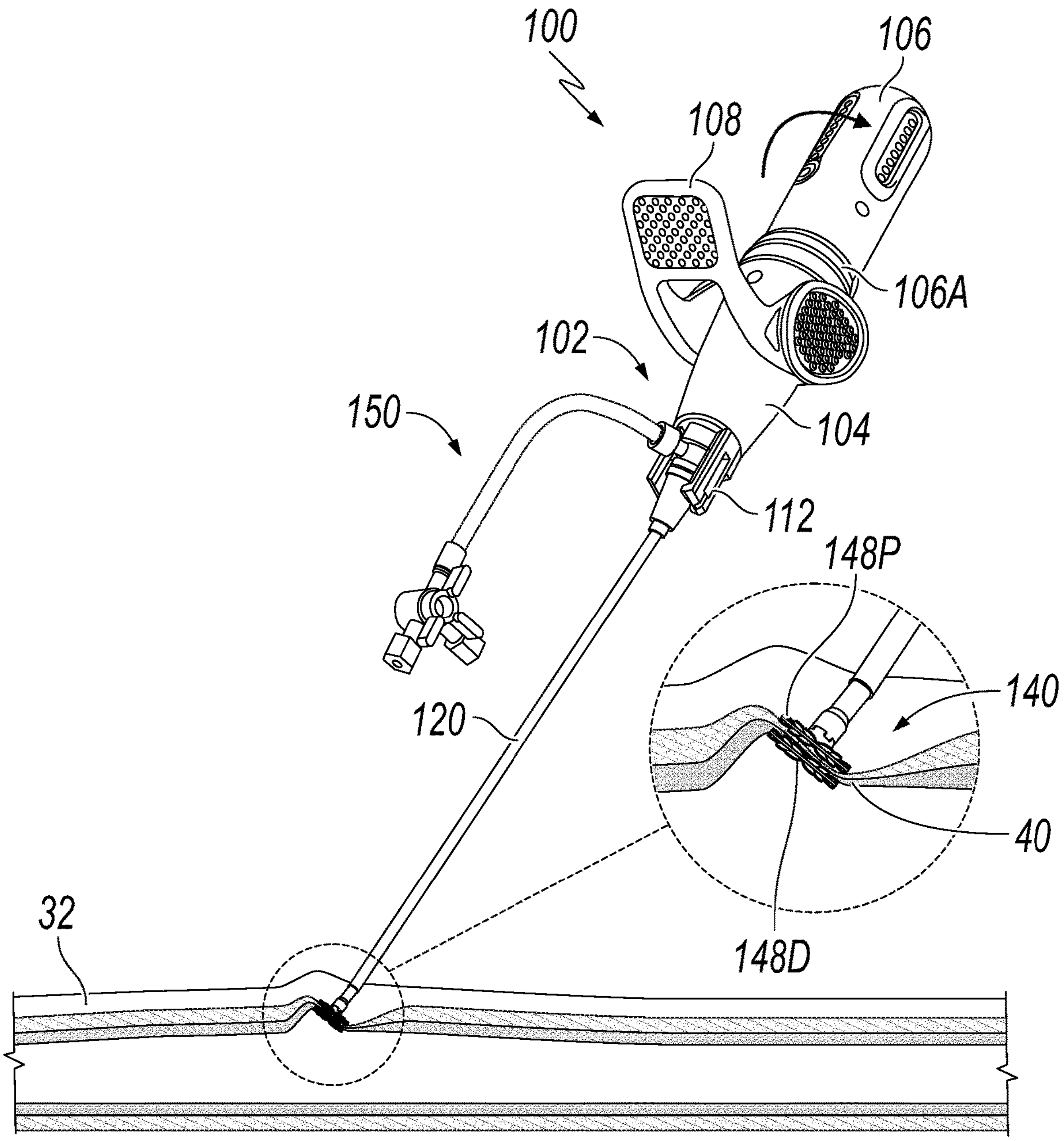
FIG. 16 is a perspective view of the closure assembly of FIG. 13 with deployed distal and proximal wings securing tissue therebetween, with an insert highlighting the deployed distal and proximal wings.
Figure 17:
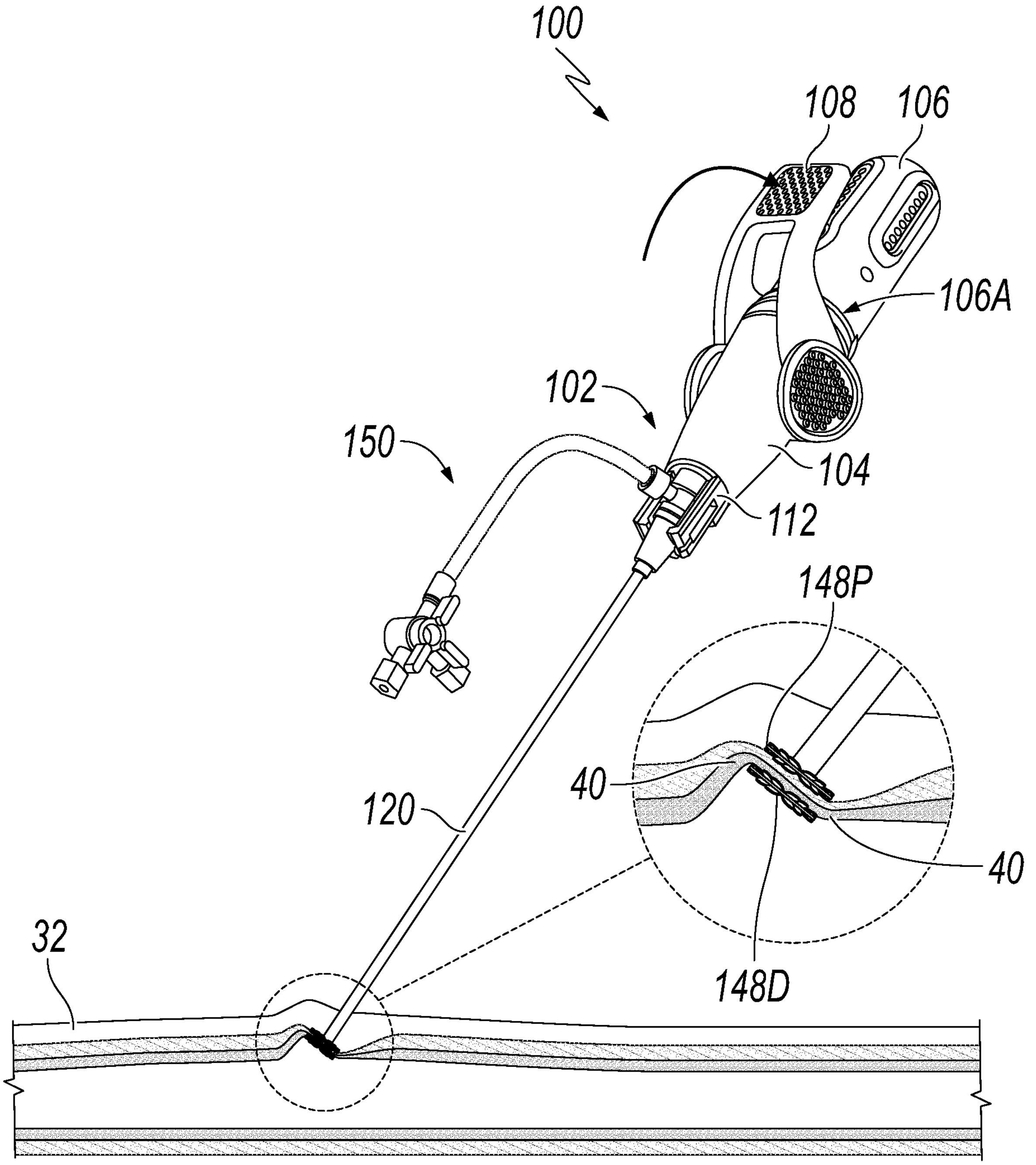
FIG. 17 is a perspective view of the closure assembly of FIG. 13 with an ejection lever being actuated, with an insert highlighting the secured tissue.
Figure 18:
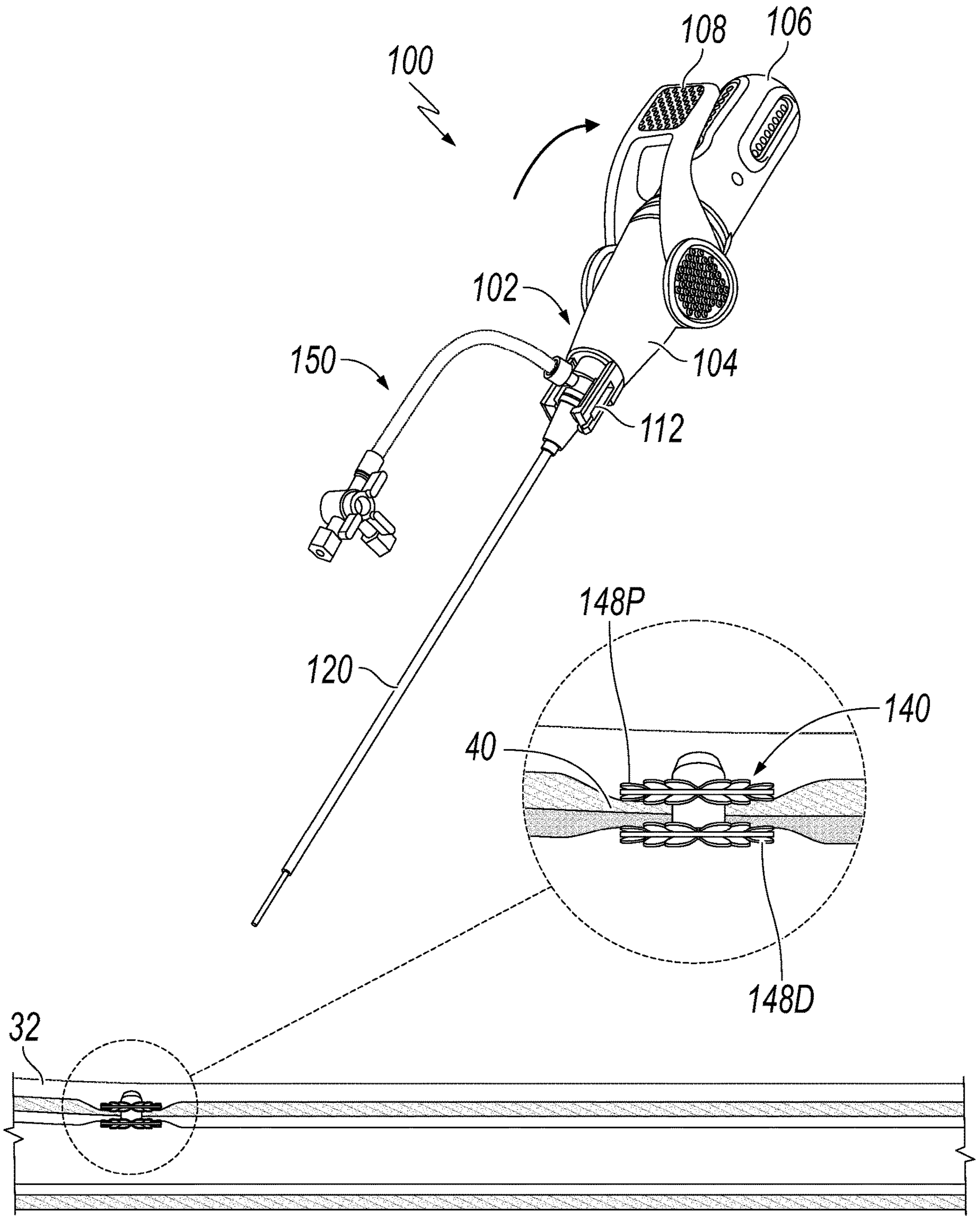
FIG. 18 is a perspective view of the closure assembly of FIG. 13 being removed from a surgical sight following ejection of the deployable coupler, with an insert highlighting the ejected coupler.
Figure 19:
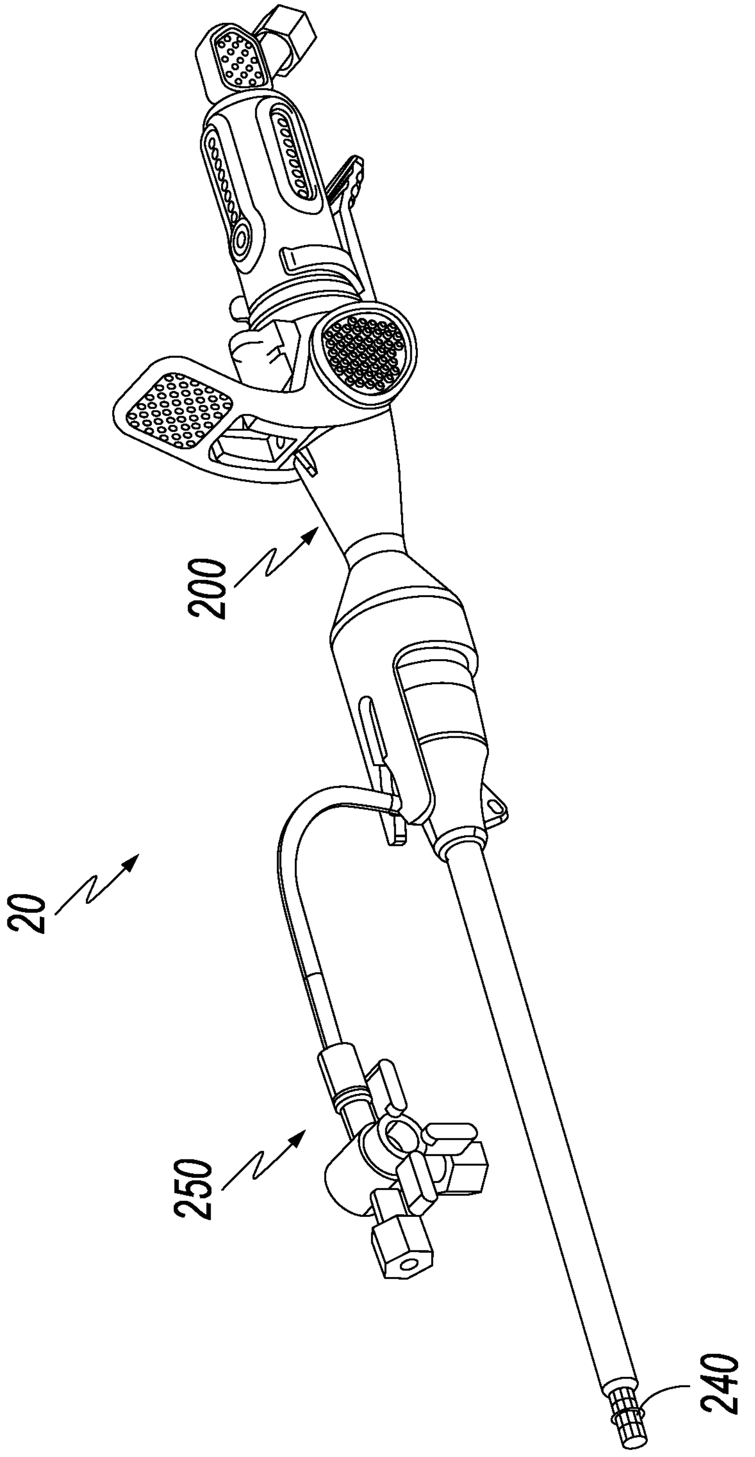
FIG. 19 is a perspective view of a closure assembly, including an actuator assembly and an introducer sheath, according to another embodiment.

FIG. 15 depicts the deployment of the distal wing 148D within the arterial lumen 32 via rotational actuation of the proximal handle 106. With the removable locking tab 110 removed, the proximal handle 106 can be actuated in a first direction (e.g., clockwise), to deploy the distal wing 148D of the deployable coupler 140 within the arterial lumen 32. After deployment of the distal wing 148D, the actuator assembly 100 can be withdrawn from the patient to cause the distal wing 148D to contact an inner surface of the arterial lumen 32, thereby positioning the slits 144 of the deployable coupler 140 outside of the arterial lumen, preventing blood flow into the slits 144, and halting the blood signal. If necessary, the actuator assembly 100 can be reinserted into the arterial lumen 32 to allow blood to flow back through flexible guide tube 120 and out the blood signal outlet 116, and retracted again to halt the blood signal to reconfirm correct positioning of the deployable coupler 140. If reinsertion occurs, blood can flow via the proximal slits 144P to facilitate the blood signal. When the position of the deployable coupler 140 is confirmed to be correct, the actuator assembly 100 can be pivoted to a more vertical orientation relative to the tissue to increase an angle A between the surface of the tissue and the actuator assembly 100, as seen in FIG. 15. This angle can vary, depending upon the patient, size of the arterial lumen, size of the deployable coupler 140, etc. and can be at least 30 degrees. In some embodiments, the angle A can be between 40 and 60 degrees. Pivoting in this manner can cause the deployed distal wing 148D to more firmly contact the inner wall of the arterial lumen 32. Once in position, the proximal handle 106 can be rotated in the second direction (e.g., counter-clockwise) to deploy the proximal wing 148P and capture tissue between the distal wing 148D and the proximal wing 148P, as shown in FIG. 16. Actuation of the proximal handle 106 in the second direction to a correct limit can cause a gap 106A to appear between the proximal handle 106 and the cylindrical body 104, indicating that the proximal handle 106 was correctly actuated to deploy the proximal and distal wings 148P, 148D of the deployable coupler 140. After the proximal wing 148P is deployed, a sandwich "push-pull" test can be performed by gently oscillating the actuator assembly 100 toward and away from the captured tissue. If deployment is performed correctly, it may not be possible to advance the deployed coupler into the arterial lumen 32 during the push-pull test. Further, while conducting the push-pull test, no blood signal should be visible, as the entry point of the blood flow path—the slits 144 of the deployable coupler 140—have come to define the proximal and distal wings 148P, 148D, and blood cannot enter the flexible guide tube 120. With proper positioning confirmed, the ejection lever 108 can be articulated by pulling the ejection lever 108 proximally toward the proximal handle 106 to cause the deployable coupler 140 to eject from the flexible guide tube 120. The proximal actuator 102 and the introducer sheath 150 can be removed from the surgical site, as shown in FIGS. 17 and 18.

With reference now to FIGS. 19-30, a closure assembly 20 for use with large bore closures is shown. The closure assembly 20 can be used in conjunction with larger punctures than the closure assembly 10, which may be necessary for certain surgical procedures. If a puncture is too large, occluding and/or coupling the puncture or surrounding tissue can be risky or even impossible. The closure assembly 20 can include a guidewire 30, an actuator assembly 200, an deployable coupler 240, an introducer sheath 250, a plug tool 260, and a contrast port 270. The actuator assembly 200 can include an actuator 202 and a guide tube 220. The actuator assembly 200 can further include a central lumen 203 running through the actuator 202 and the guide tube 220, as will be described in greater detail below. In general, many of the elements and features of the closure assembly 20 are similar to the closure assembly 10, and for brevity, like components will not be described again in detail.

Figure 20:
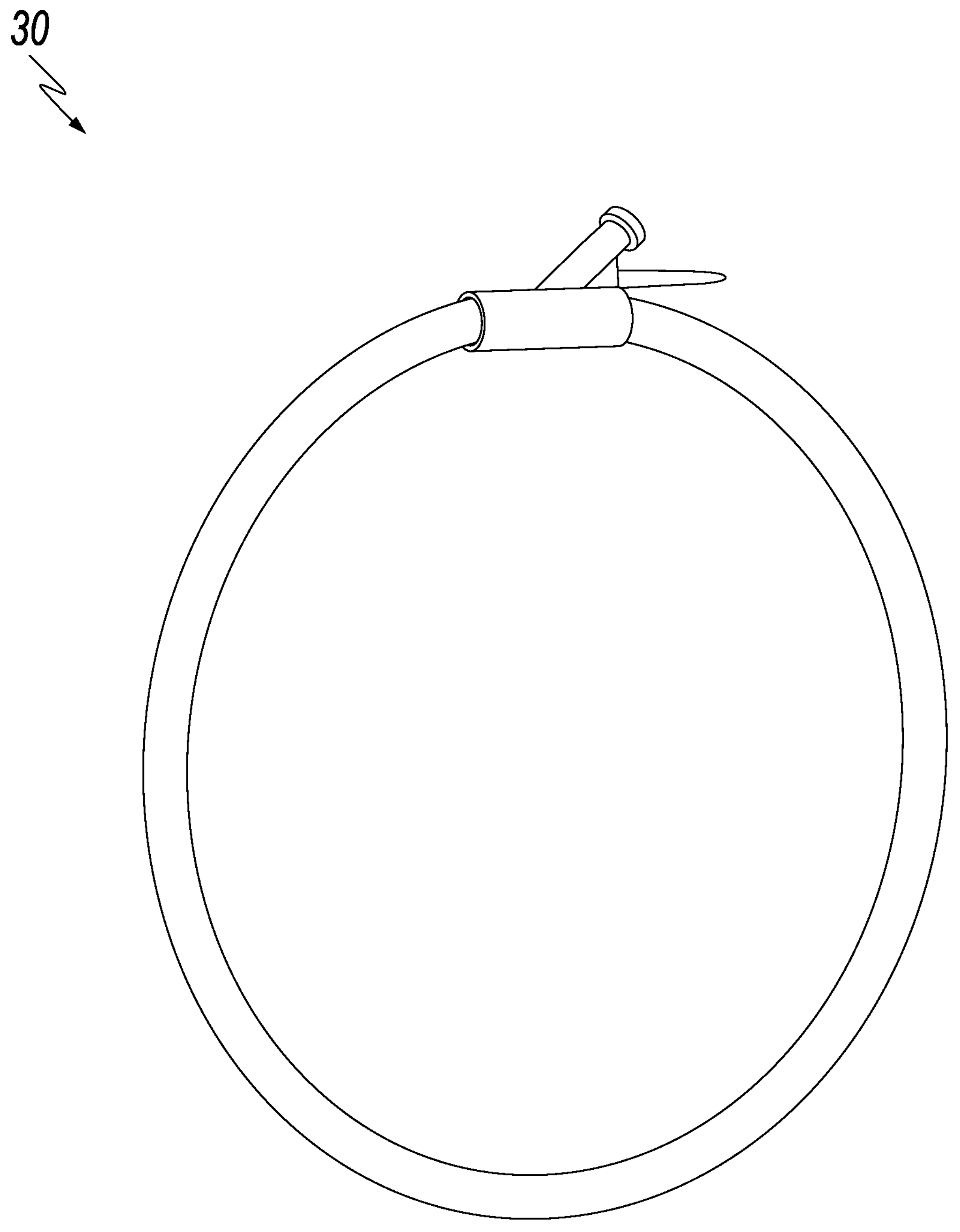
FIG. 20 is a perspective view of a guidewire usable with the closure assembly of FIG. 19.

FIG. 20 depicts the guidewire 30. The guidewire 30 can be any standard-type guidewire known to those in the art. The guidewire 30 can be pre-inserted into a tissue and/or a cavity to aid in guiding surgical tools to a surgical site or site of interest. While the guidewire 30 can vary in specifics, depending upon the remainder of the closure assembly 20, in some embodiments, the guidewire 30 can have a diameter between approximately 0.01 and 0.05 inches. For example, the guidewire can have a diameter of approximately 0.035 inches.

Figure 21:
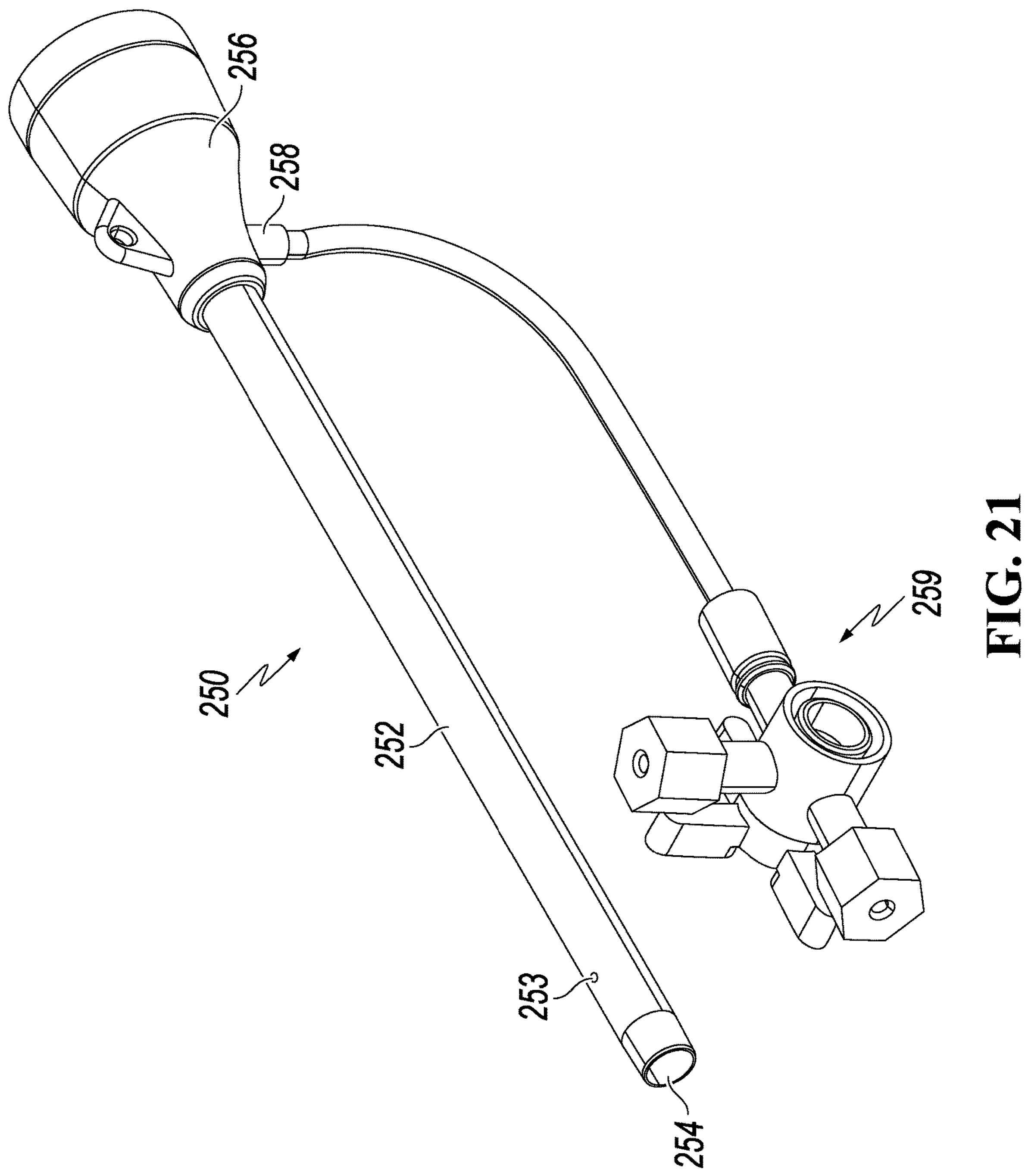
FIG. 21 is a perspective view of an introducer sheath of the closure assembly of FIG. 19.

FIG. 21 depicts the introducer sheath 250. The introducer sheath 250 can include an elongate shaft 252 attached to a hub 256 at a proximal end thereof. The elongate shaft 252 can define an inner lumen 254, and a distal end of the elongate shaft 252 can include one or more fluid holes 253 positioned on a sidewall thereof. The hub 256 can be flared in shape and can have a port 258 extending from one side that leads to a valve assembly 259 for use during a surgical procedure as a blood signal. The port 258 and valve assembly 259 can be configured to provide a connection point for coupling the introducer sheath 250 with the actuator 202. The introducer sheath 250 can come in various sizes, and each size introducer sheath 250 can be suited to close a range of puncture sizes.

Figure 22:
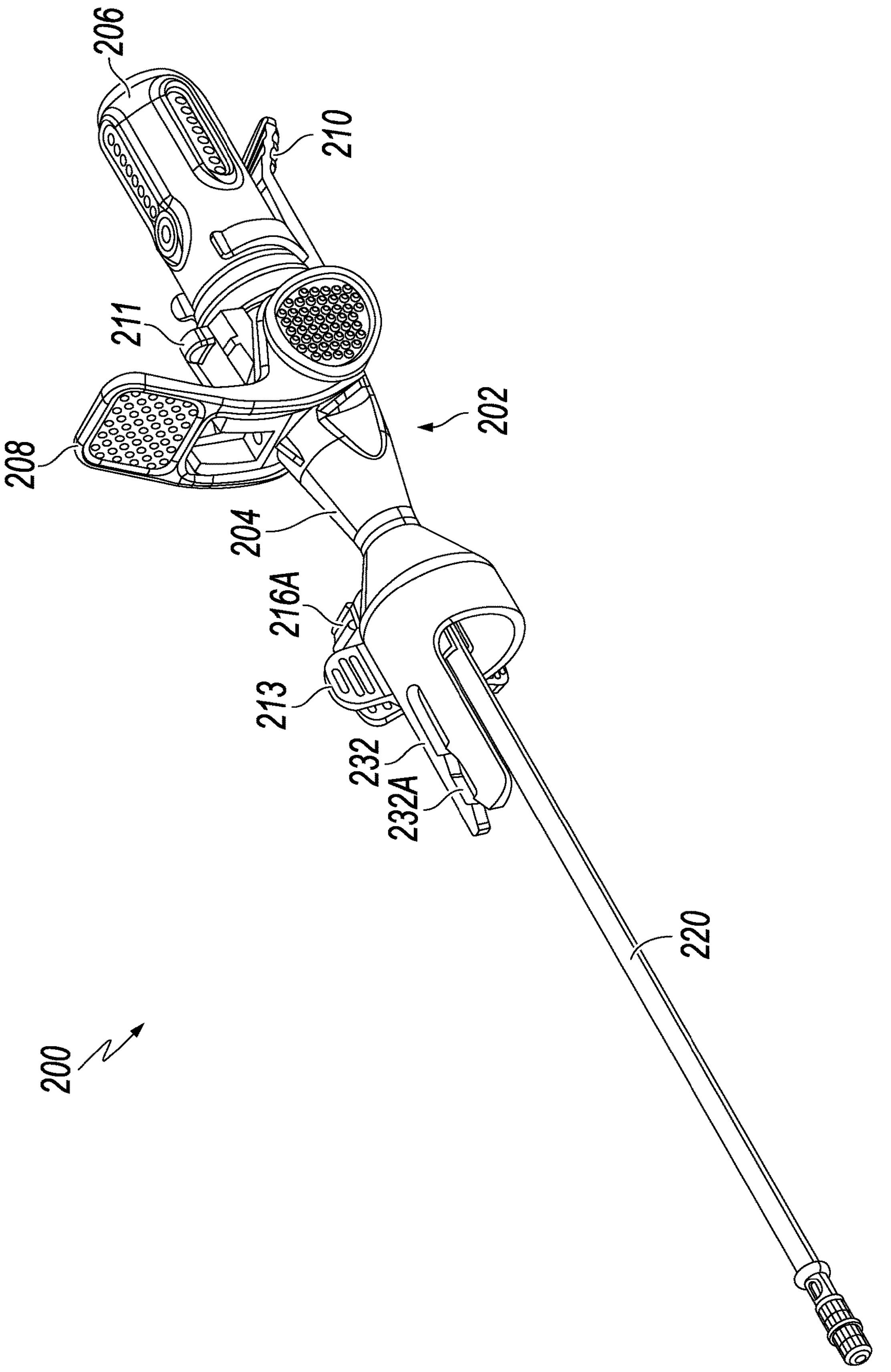
FIG. 22 is a perspective view of an actuator assembly of the closure assembly of FIG. 19.

FIG. 22 depicts the actuator assembly 200 in greater detail. The actuator assembly 200 can be similar to the actuator assembly 100, and it can include the actuator 202 having the guide tube 220 extending distally therefrom. The actuator 202 can generally include a body 204, a handle 206, and an ejection lever 208, like those described above with respect to the actuator 102. The actuator 202 can also include a removable locking tab 210 configured to prevent premature actuation of the handle 206, and a removable lever lock 211 configured to prevent premature actuation of the ejection lever 208. The actuator 202 can include a sheath retainer 232 extending proximate to the guide tube 220 configured to couple to the introducer sheath 250.

In some embodiments, the sheath retainer 232 can include a central track having a plurality of engagement zones (not shown) configured to engage the introducer sheath 250 at a plurality of distances, thereby allowing for the guide tube 220 to be inserted into the introducer sheath 250 at substantially discrete insertion depths to facilitate blood flow through a blood signal outlet 216. The actuator 202 can have a variable number of engagement zones, such as one, two, three, or more. The assembly 200 can also include a removable sheath stop 213 configured to prevent over-insertion of the guide tube 220 into the introducer sheath 250. The removable sheath stop 213 can be coupled to the actuator 202 near the sheath retainer 232, and it can block the more-proximal engagement zone(s) to prevent over-insertion of the guide tube 220 into the introducer sheath 250. More than one removable sheath stop 213 can be used if more than one more-proximal engagement zone is used. When additional depth is required, the removable sheath stop 213 can be decoupled from the actuator 202 to expose the more-proximal engagement zone(s). After coupling with the introducer sheath 250, the guide tube 220 can then be inserted further into the introducer sheath 250. The blood signal outlet 216 can be located on a side of the body 204. The blood signal outlet 216 can include a blood signal cap 216A to seal off the blood signal outlet 216.

Figure 23:
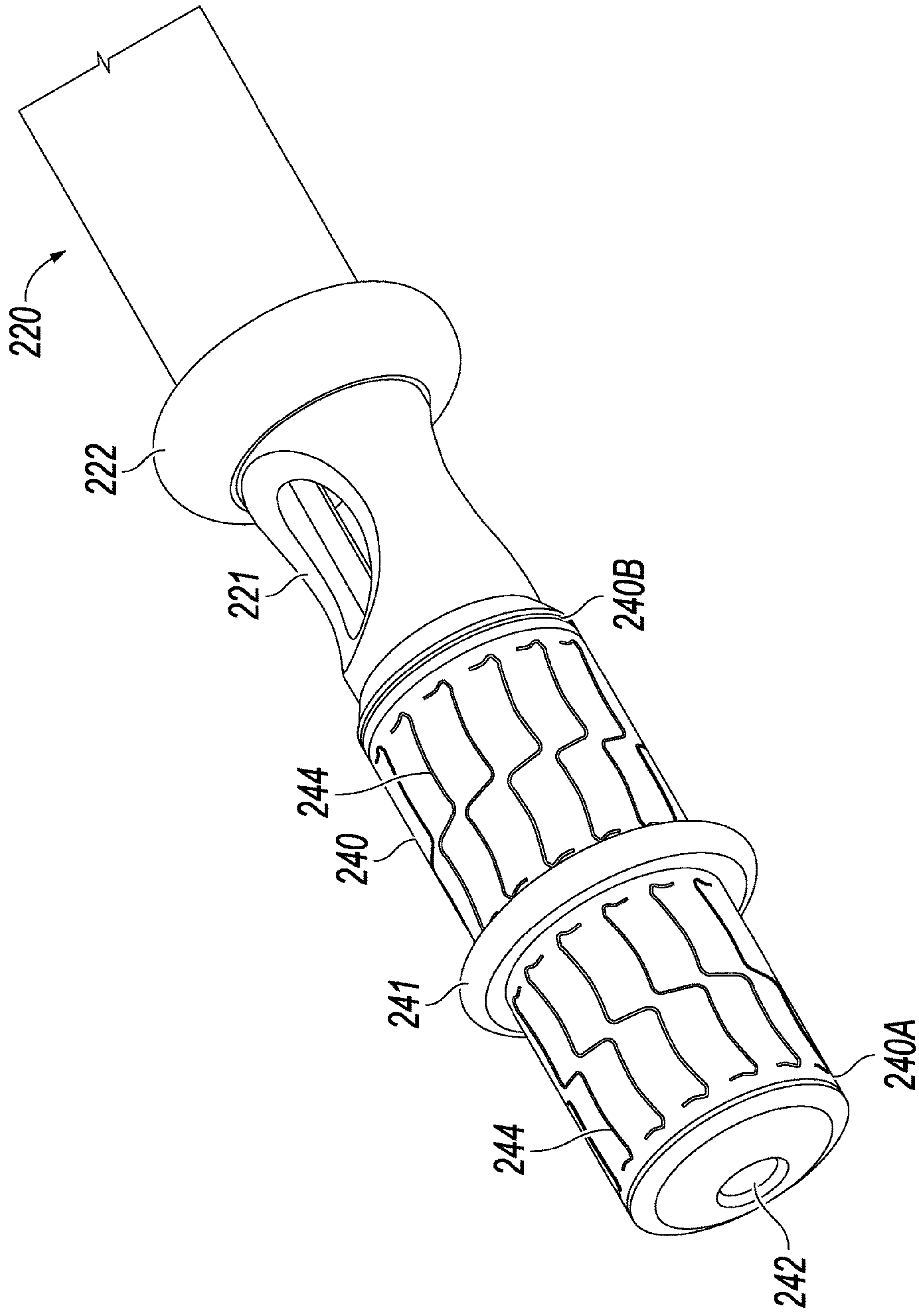
FIG. 23 is a perspective view of a distal tip of the actuator assembly of FIG. 22 including an affixed deployable coupler.
Figure 24:
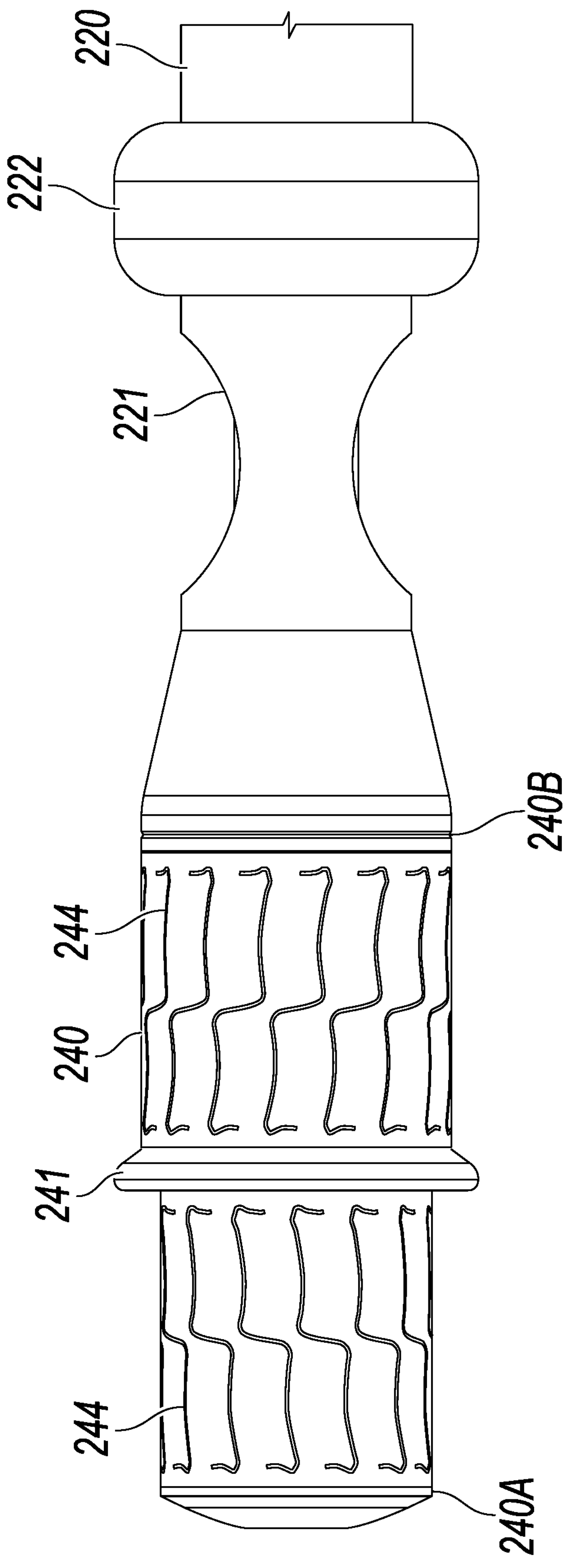
FIG. 24 is a side view of a distal tip of the actuator assembly of FIG. 22 having an affixed anastomotic coupler including a proximal end having a greater diameter than a distal end.
Figure 25:
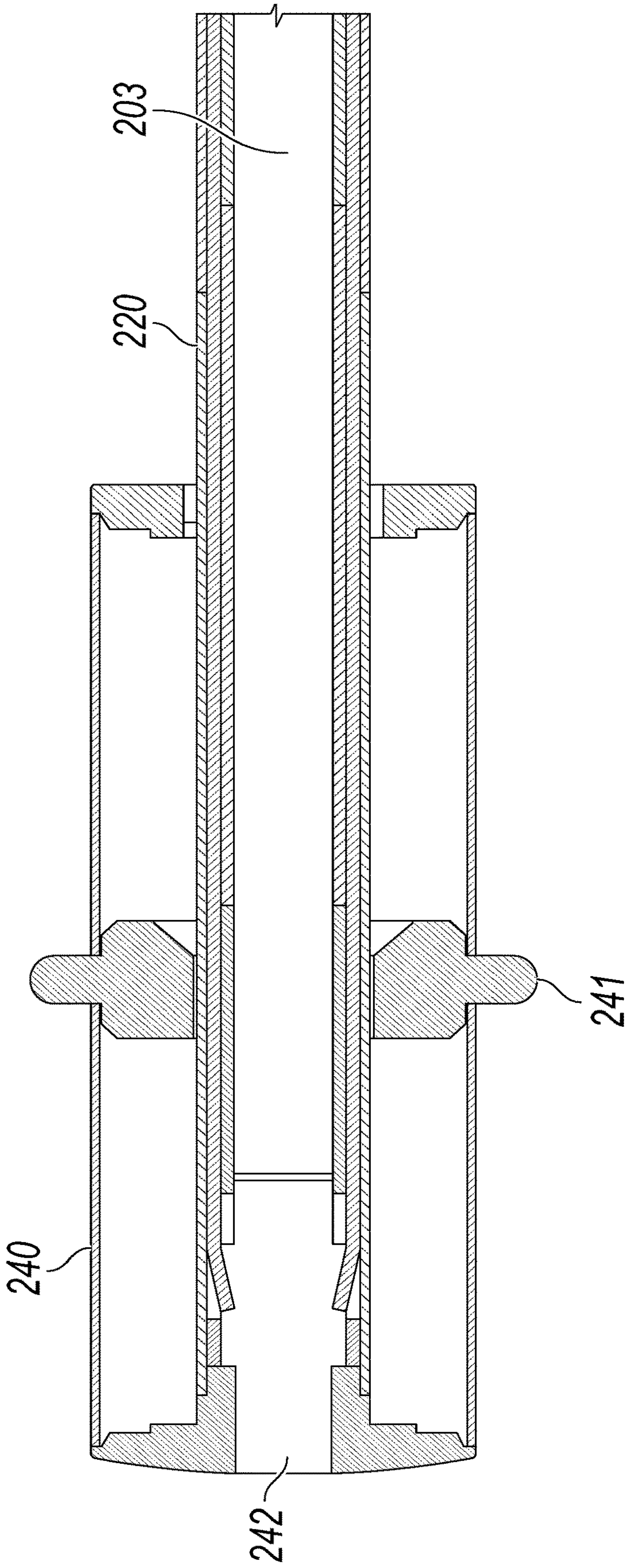
FIG. 25 is a cross-sectional view of the deployable coupler of FIG. 23.

The guide tube 220 can extend distally from the actuator 202. The guide tube 220 can be substantially tubular and can couple a large bore coupler 240 on an end thereof. FIGS. 23-25 illustrate a close-up view of the end of the guide tube 220 having a large bore coupler 240 affixed thereto. The guide tube 220 can include at least one blood inlet 221 located proximal to the affixed coupler 240, which can be in fluid communication with the blood signal outlet on the device 216A. Just proximal of the blood inlet 221 can be a seal 222 disposed circumferentially around the guide tube 220. When the guide tube 220 is inserted into the introducer sheath 250, the seal 222 can prevent the backflow of blood up the interior of the introducer sheath 250.

The coupler 240 can be generally cylindrical in form and can include a substantially tubular first end 240A and a substantially tubular second end 240B joined by a mid-region 241. The mid-region 241 can take the form of a press ring or similar structure. Together, the first end 240A, the second end 240B, and the mid-region 241 can define a central lumen 242 running through the center of the coupler 240 about a longitudinal axis thereof, which can be co-linear with the central lumen 203 of the actuator assembly 200. The first and second ends 240A, 240B can have the same or different diameters as shown, for example, in FIGS. 23 and 24. The mid-region 241 can have also have a same or different diameter, and in some embodiments, the diameter of the mid-region 241 can be greater than diameters of each of the first end 240A and second end 240B.

Figure 26:
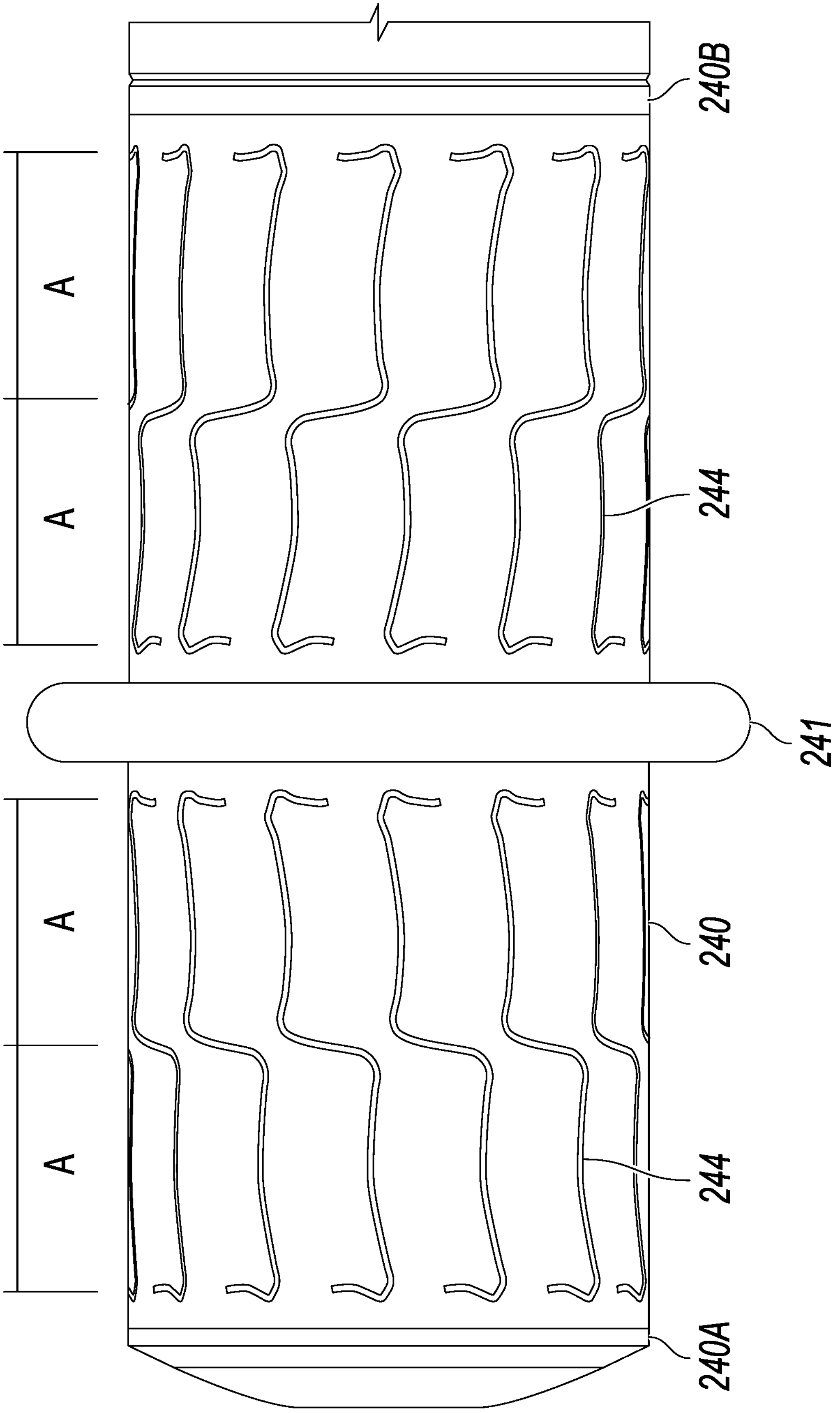
FIG. 26 is a side view of the deployable coupler of FIG. 23 in a delivery configuration having proximal and distal slits with slit halves having a distance ratio substantially equal to 1:1, according to some variations.
Figure 27:
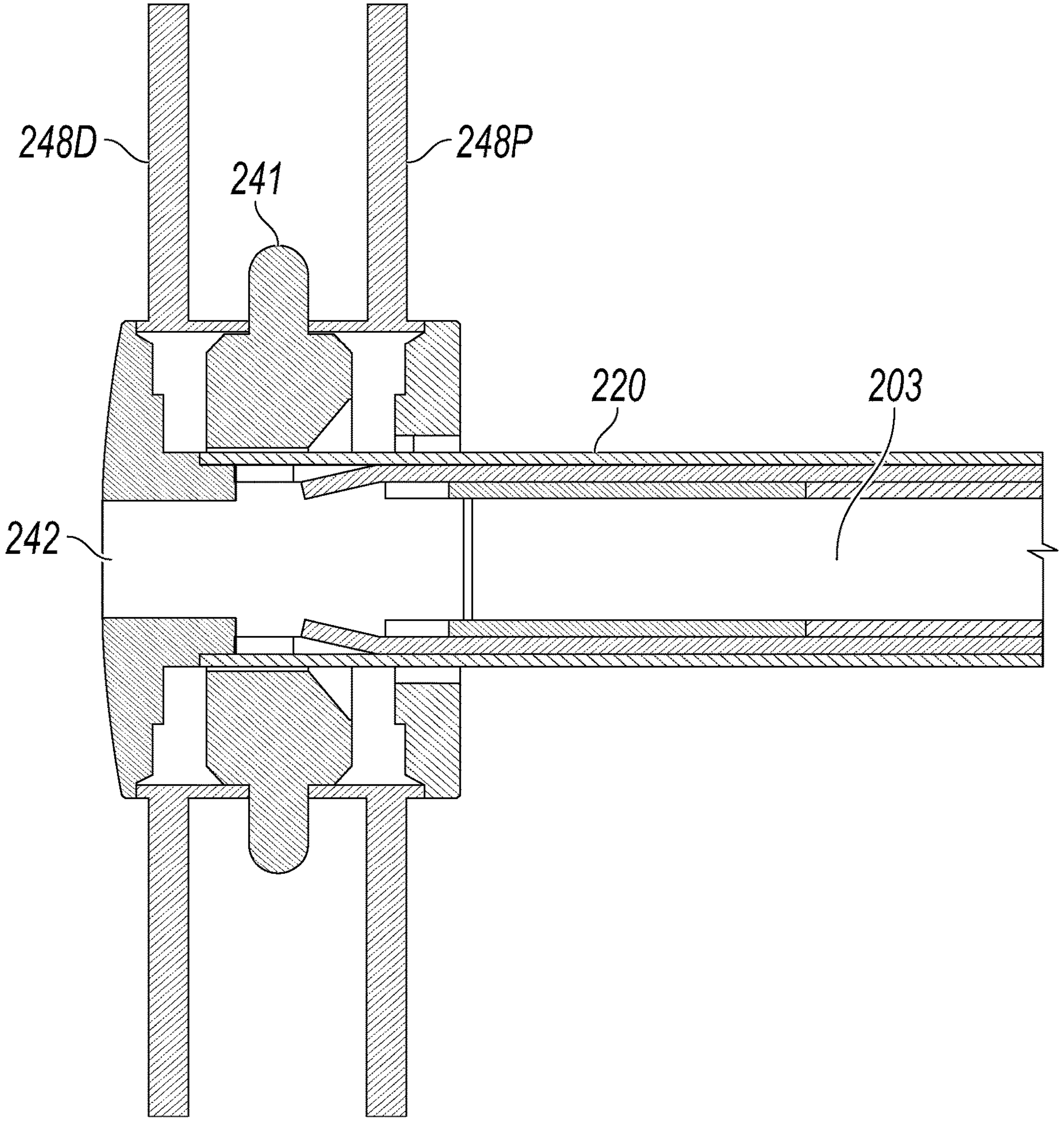
FIG. 27 is a cross-sectional view of the deployable coupler of FIG. 26 in a deployed configuration, affixed to the actuator assembly.
Figure 28:
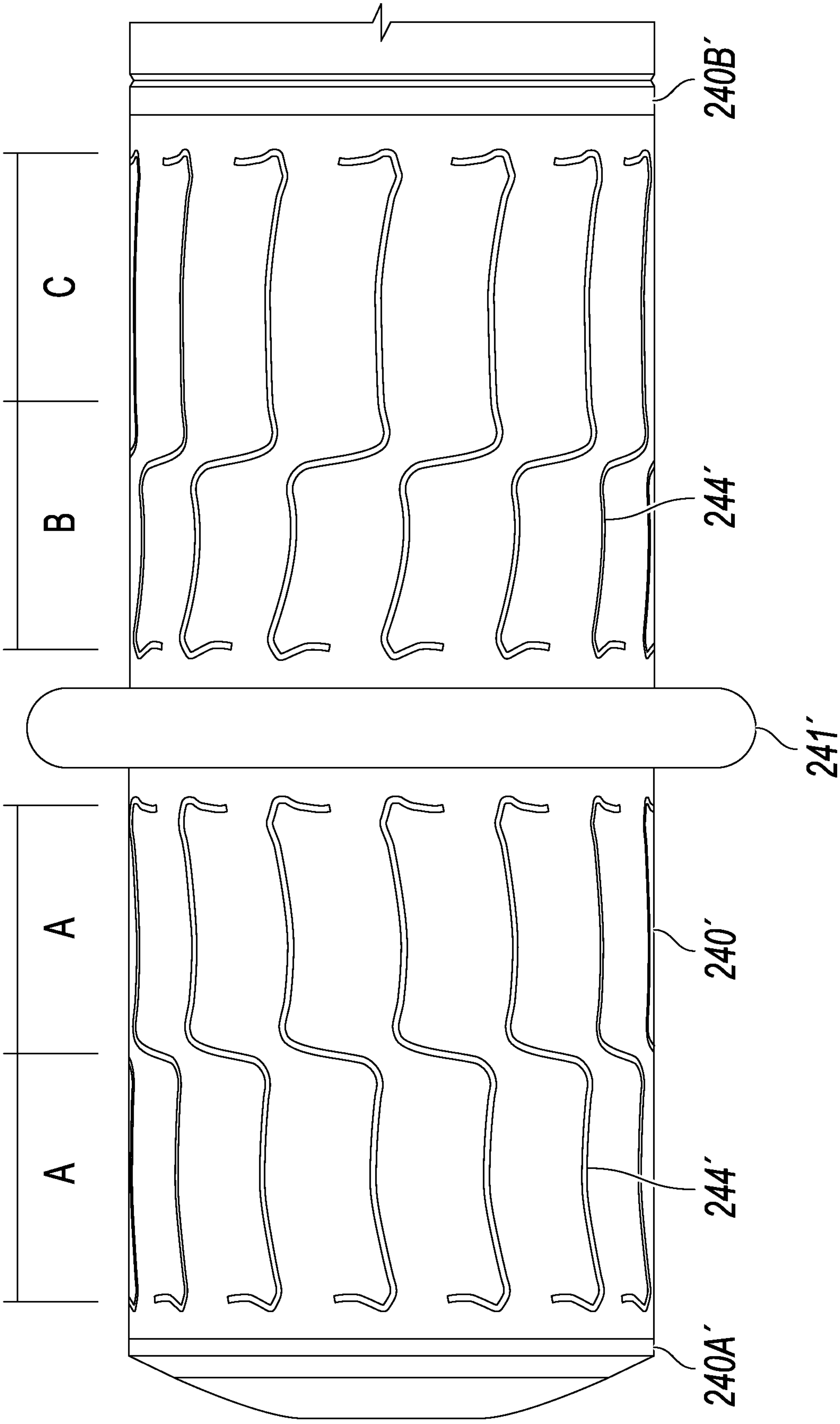
FIG. 28 is a side view of the deployable coupler of FIG. 23 in a delivery configuration having distal slits with slit halves having a distance ratio substantially equal to 1:1 and having proximal slits with slit halves having a distance ratio substantially less than 1:1, according to some variations.
Figure 29:
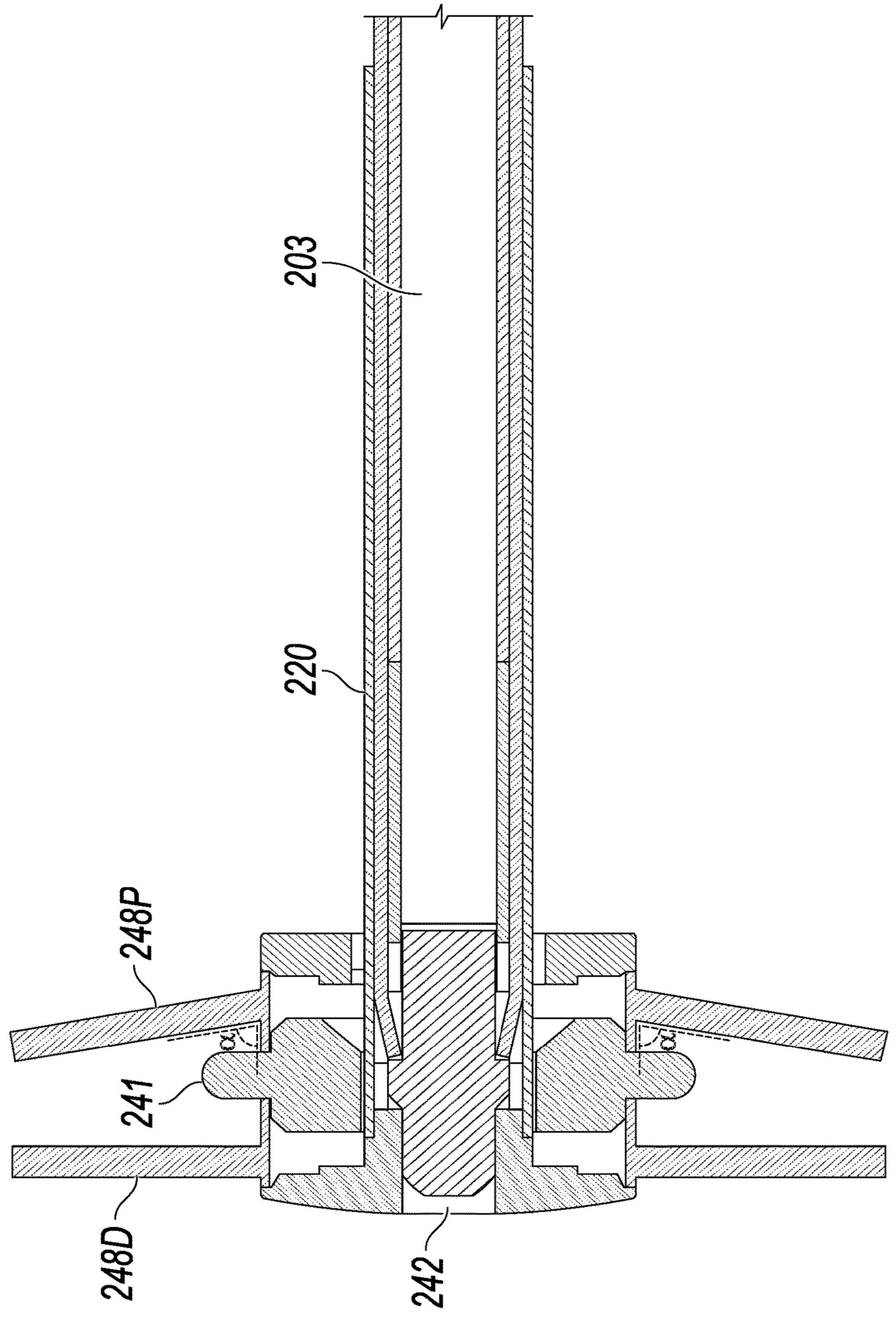
FIG. 29 is a cross-sectional view of the deployable coupler of FIG. 28 in a deployed configuration, affixed to the actuator assembly

Each of the first end 240A and the second end 240B can include a plurality of slits 244. The slits 244 can vary in shape, but as seen, for example, in FIGS. 26 and 28, the slits 244 can be substantially a mirror image of each other and can be substantially s-shaped or z-shaped or similar. Each of the slits 244 can be separated into two halves, and the ratio of the length these halves of each slit 244 can vary. For example, in some embodiments, the length ratio can be substantially 1:1, as seen in FIG. 26, for example, where the length of each half is denoted “A.” In other embodiments, the ratio can be substantially less than or greater than 1:1, as seen in FIG. 28, for example, where the length of one half is denoted “B” and the length of the other half is denoted “C,” and the ratio of B:C is substantially less than 1:1.

The coupler 240 can be transformable between a delivery configuration and a deployed configuration, similar to the deployable coupler 140, as explained above. In the delivery configuration, seen in FIGS. 26 and 28, the coupler 240 can be substantially linear in form, while in the deployed configuration, seen in FIGS. 27 and 29, the coupler 240 can have deployed proximal and distal wings 248P, 248D flaring radially outward from the coupler 240. The shape of the slits 244 can inform the shape of the wings 248P, 248D when deployed in the deployed confirmation. Moreover, the length ratio of the halves of each slit 244 can inform a deployment angle of the wings 248P, 248D relative to a longitudinal axis of the coupler 240. For example, if the length ratio is substantially equal to 1:1, such as in FIG. 26, the proximal wing 248P and/or the distal wing 248D can deploy at an angle substantially equal to 90 degrees relative to the longitudinal axis. This deployment can be seen in FIG. 27. If the length ratio is substantially greater or less than 1:1, such as in FIG. 28, the proximal wing 248P and/or the distal wing 248D can deploy at an angle substantially skew to the longitudinal axis. This deployment can be seen in FIG. 29, where the proximal wing 248P has deployed at a generally acute angle $\alpha$. In other embodiments, each of the wings 248P, 248D can deploy at obtuse angles, acute angles, right angles, or a combination thereof. Moreover, the deployment angle, e.g., angle $\alpha$, can vary between the wings 248P, 248D.

Figure 30:
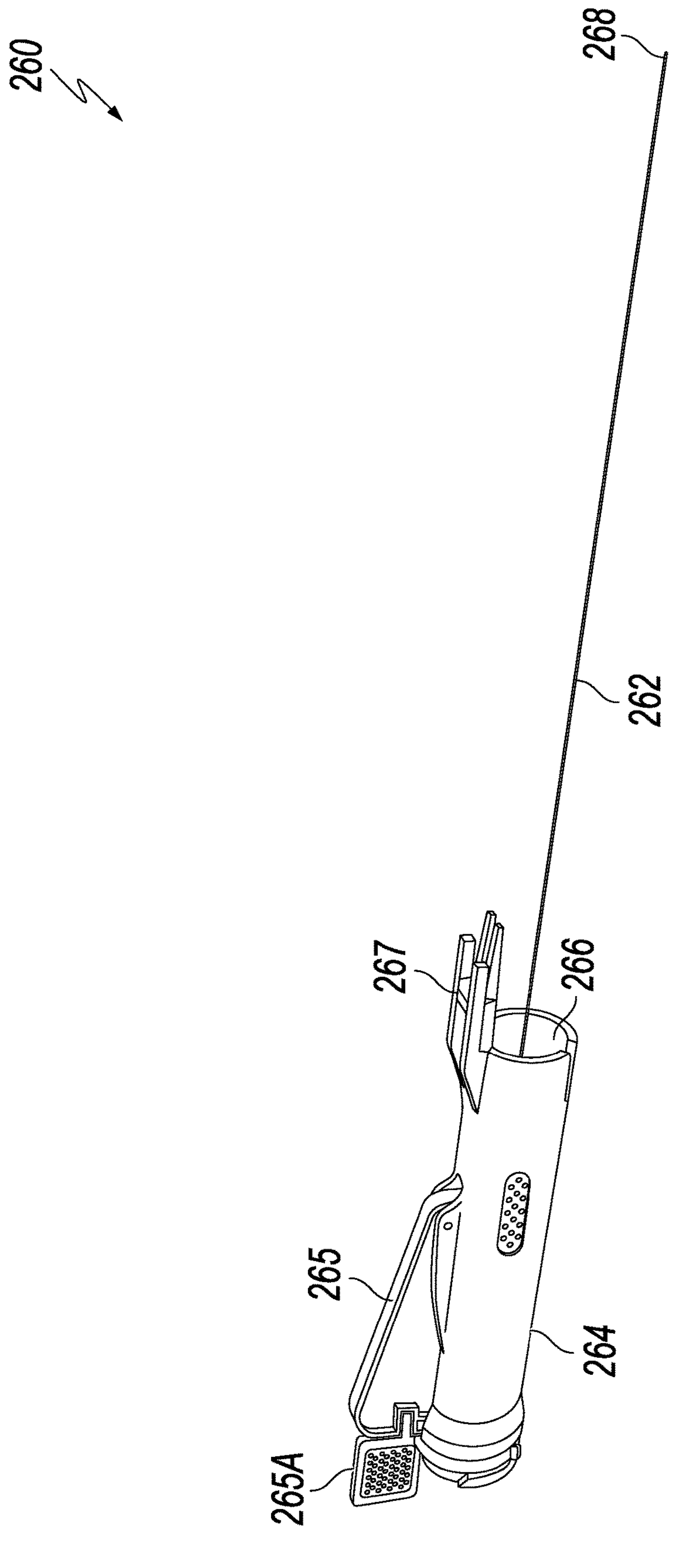
FIG. 30 is a perspective view of a plug tool usable with the closure assembly of FIG. 19.
Figure 31:
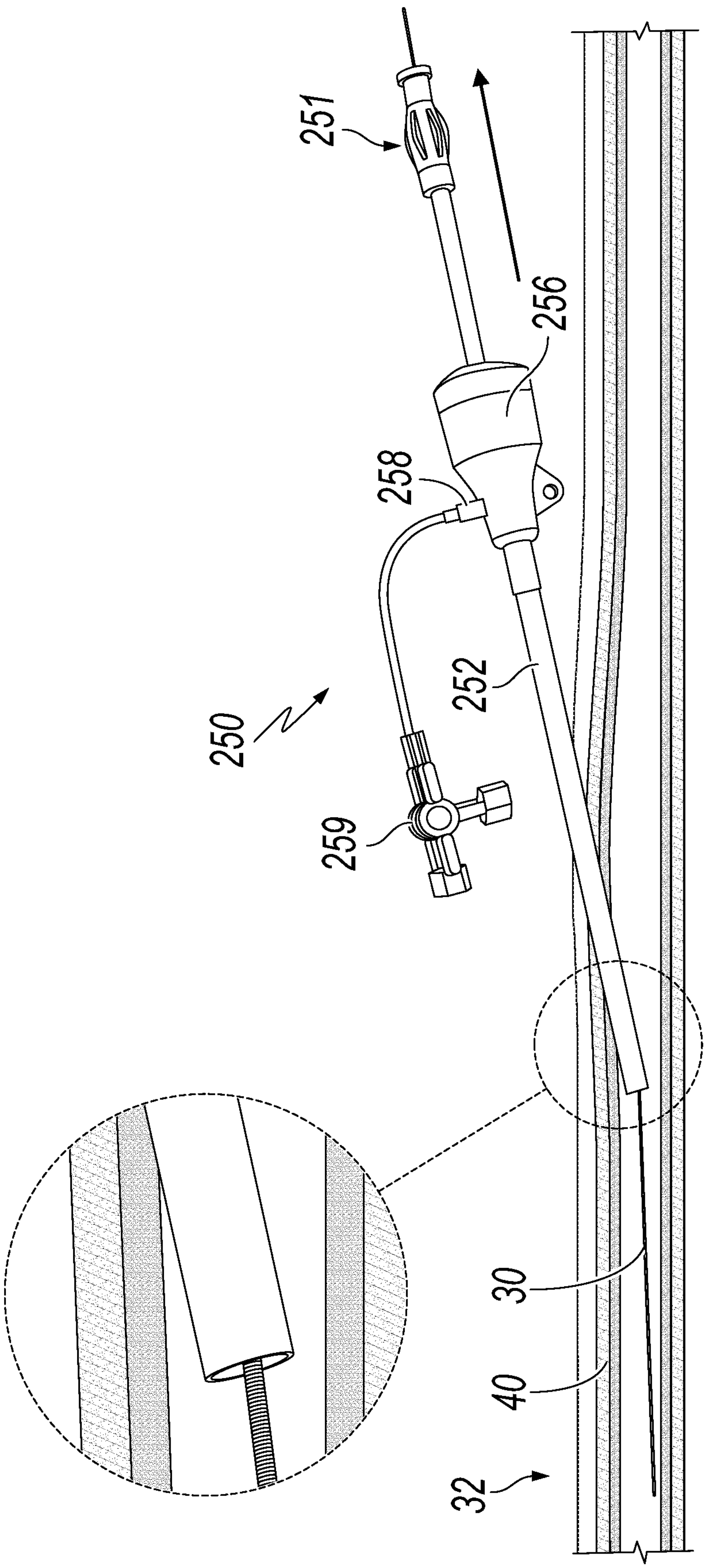
FIG. 31 is a perspective view of the introducer sheath of FIG. 19 inserted into an arterial lumen over the guidewire of FIG. 20.
Figure 32:
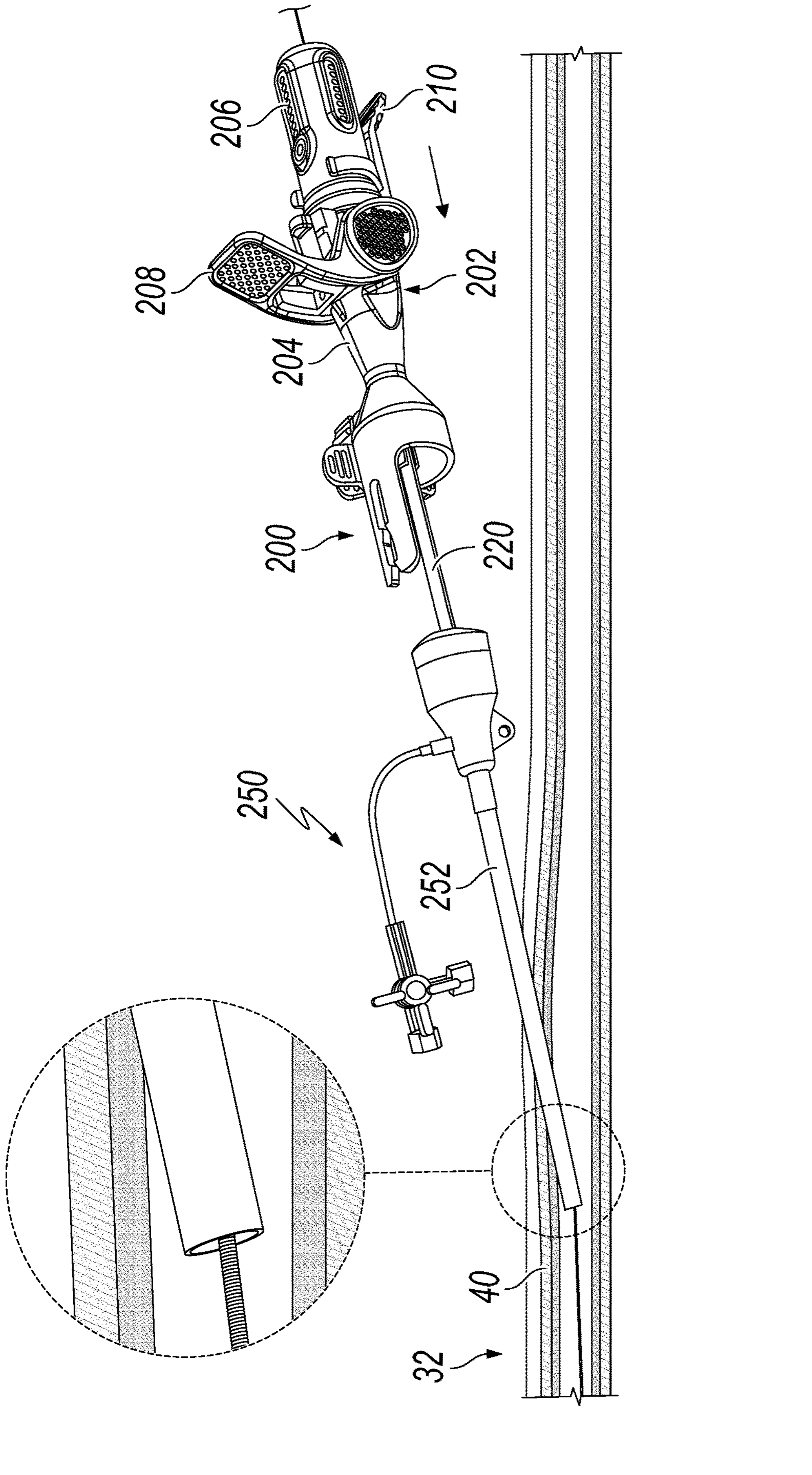
FIG. 32 is a perspective view of the actuator assembly of FIG. 19 being inserted into the introducer sheath and into the arterial lumen.

FIG. 30 depicts the plug tool 260 in greater detail. The plug tool 260 can be used to plug the central lumen 242 of the coupler 240 in order to prevent or occlude fluid flow therethrough. While the plug tool 260 may not be needed in surgical procedures where occlusion or prevention of fluid flow is desired, the plug tool can provide additional versatility for the treatment of various ailments. The illustrated plug tool 260 includes a substantially cylindrical plug tool handle 264 having a plug shaft 262 extending distally therefrom. The plug tool handle 264 can include a distal crevice 266 from which the plug shaft 262 extends, and the distal crevice 266 can be sized to removably receive the handle 206 of the actuator 202. An ejectable plug 268 can be removably affixed to a distal end of the plug shaft 262. The handle 264 can also include a lever 265 extending from a side thereof. Upon actuation, the lever 265 can be configured to eject the ejectable plug 268 from the distal end of the plug shaft 262. To prevent premature ejection and also to retain the lever in its pre-deployment position, a plug lock 265A can be coupled to a proximal end of the handle 264 and can interfere with actuation of the lever 265 until an intended time during a surgical procedure. A set of prongs 267 can extend from the distal end of the handle 264 outside of the distal crevice 266. The prongs 267 can be shaped and configured to couple with the removable lever lock 211 on the actuator 202 when the plug tool 260 is affixed to the actuator 202, thereby securing the plug tool 260 to the actuator 202.

During a surgical procedure, as introduced above, the plug tool 260 can be coupled to the actuator 202 and used to plug the central lumen 242 of the coupler 240 in order to prevent or occlude fluid flow therethrough. After the guidewire 30 has been removed from the central lumen 203 of the actuator assembly 200, the plug tool 260 can be extended, plug 268 first, into the central lumen 203. The plug tool 260 can be inserted until the handle 206 of the actuator assembly 200 is secured within the crevice 266 of the plug tool 260 and until the prongs 267 couple with the removable lever lock 211. At this depth, the ejectable plug 268 can be disposed centrally within the central lumen 242 of the coupler 240. During a removal process, the plug tool 260 can be decoupled from the actuator 202. Decoupling the plug tool 260 from the actuator 202 can leave the prongs 267 coupled to the removable lever lock 211 such that removal of the plug tool 260 also removes the removable lever lock 211 in one stroke. An exemplary surgical procedure using the plug tool 260 will be described in more detail below.

FIGS. 31-48 illustrate an exemplary procedure using the actuator assembly 200 involving the deployment of the coupler 240 within an arterial lumen 32 of a patient to couple tissue. The coupler 240 can be used to join more or less tissue in other parts of a patient, therefore the procedures depicted herein are not intended to limit the overall versatility of the devices described herein. Individual steps of the procedure, or the entire procedure itself, can be adjusted to suit the needs of a patient and/or the surgeon.

The guidewire 30 can be inserted into an arterial lumen 32, proximate to a surgical site. The introducer sheath 250 can be inserted over the guidewire 30 and into the arterial lumen 32. During insertion, the introducer sheath 250 can have a dilator 251 inserted therethrough to plug the central lumen of the introducer sheath 250 and prevent the backflow of blood. Removal of the dilator 251 can allow blood to flow up the introducer sheath 250 through the blood inlet 253 and through the inner lumen 254 and out the valve assembly 259. The valve assembly 259 can be closed as needed. The tip of the elongate shaft 252 of the actuator assembly 200, having a coupler 240 affixed to a distal end thereof, can be inserted into the introducer sheath 250. The actuator assembly 200 can be advanced until the actuator assembly 200 connects with the delivery sheath 250 and the deployable coupler 240 is within the arterial lumen.

A position of the coupler 240 within the arterial lumen can be determined with an external imaging system, such as ultrasound. The press ring 241 can be positioned as close to the puncture site as possible, with a proximal portion of the coupler 240 located at least partially outside of the external lumen. Proper positioning of the coupler 240 can be determined as needed.

In some embodiments as explained above, the actuator assembly can include one or more engagement zones for use with a blood signal outlet 216. The actuator assembly 200 can be inserted until the introducer sheath 250 engages with the sheath retainer 232 and is positioned within the first of the engagement zones In this position, the coupler 240 can remain concealed by the introducer sheath 250. Once properly positioned, blood can flow out of the blood outlet 216 on the actuator 202, in addition to flowing out the introducer sheath 250, so long as the valve assembly 259 is opened. The entire assembly, introducer sheath 250 and actuator assembly 200 together, can be pulled back until the blood signal disappears. The disappearance of the blood signal can be used to confirm proper positioning of the assembly within tissue.

Figure 33:
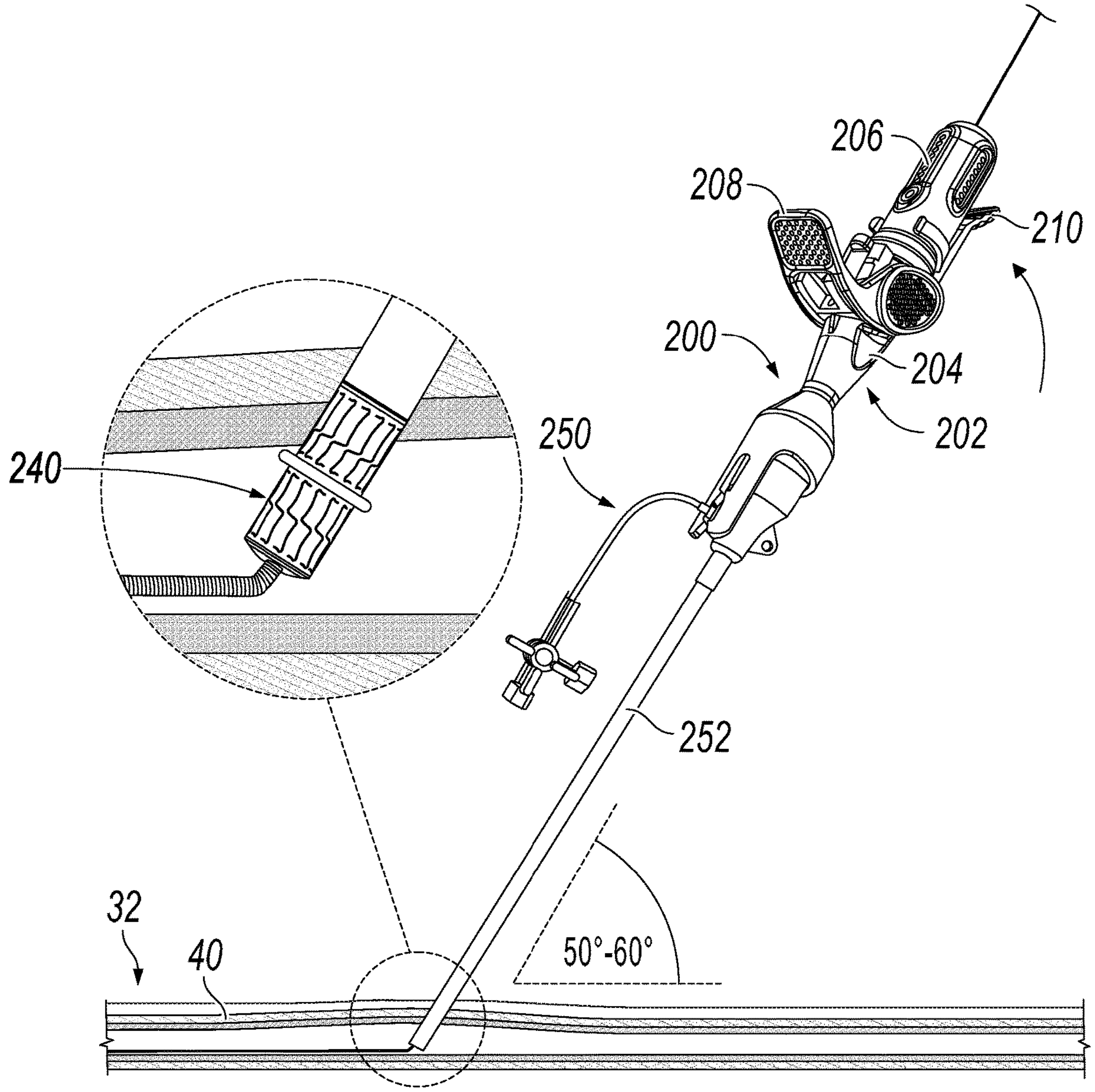
FIG. 33 is a perspective view of the actuator assembly and introducer assembly of FIG. 19 being raised to a deployment position.
Figure 34:
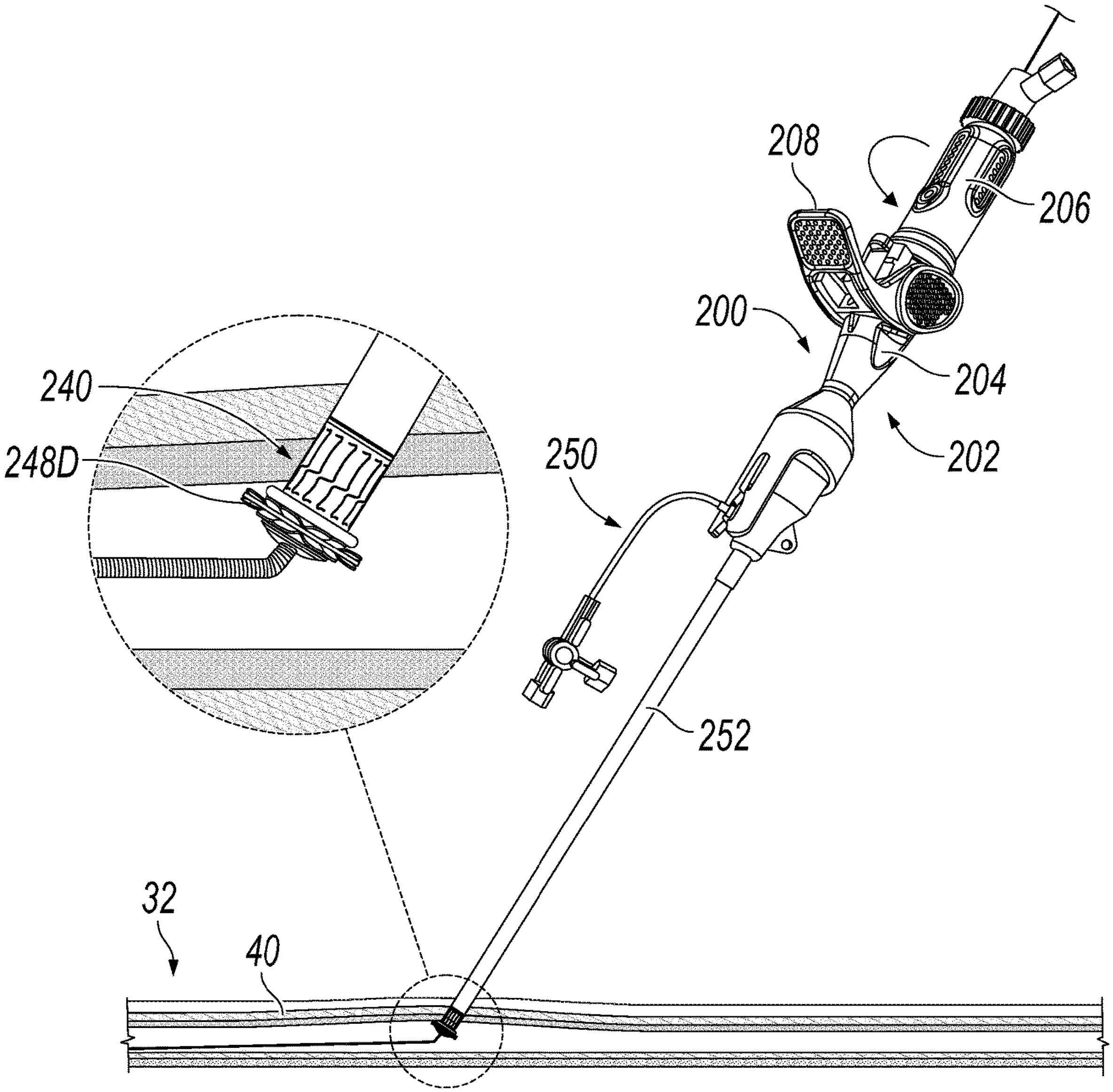
FIG. 34 is a perspective view of a proximal portion of the actuator assembly of FIG. 19 following transformation of the distal wing to the deployed configuration.
Figure 35:
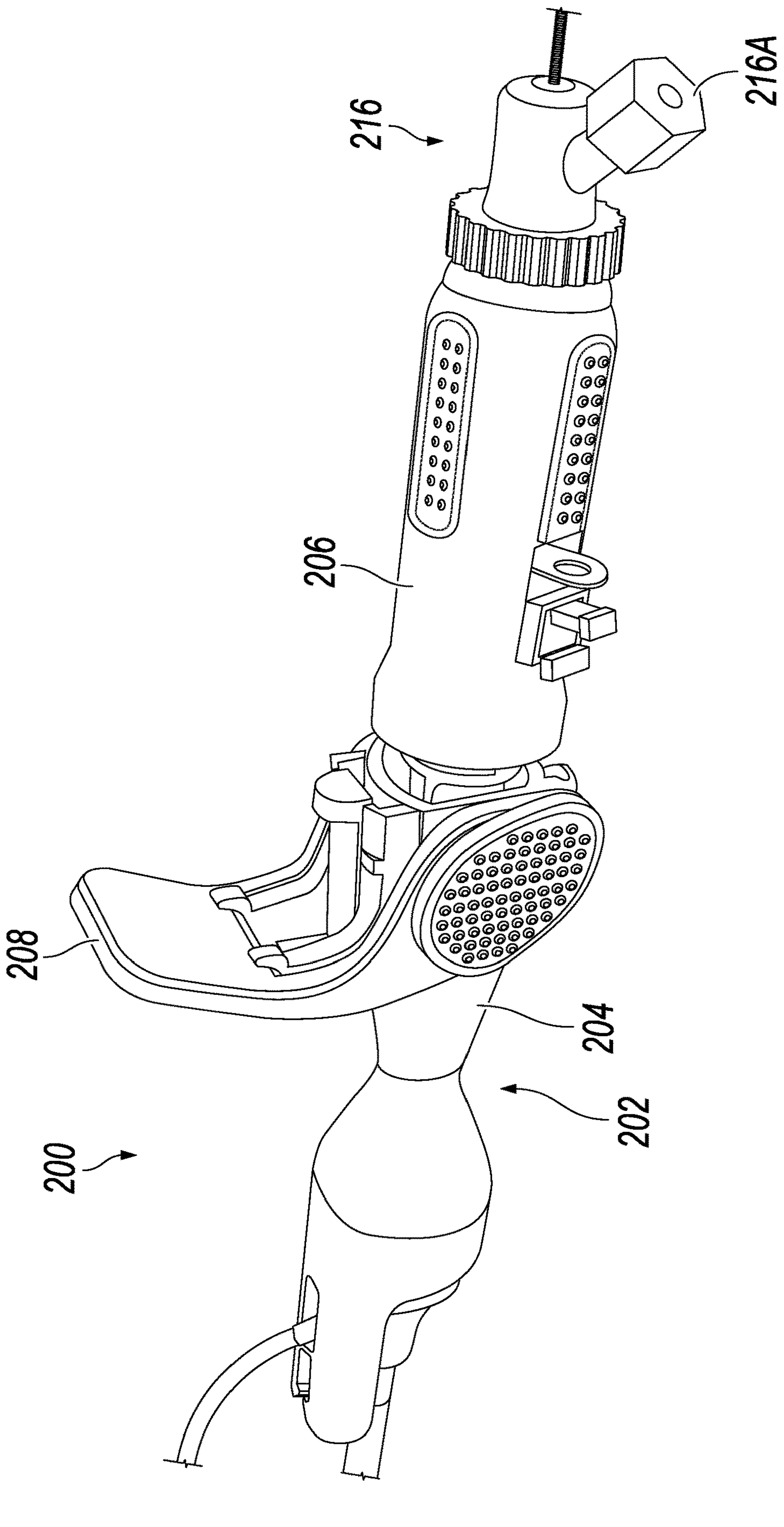
FIG. 35 is a rear perspective view of the actuator assembly of FIG. 19 and a newly-created gap following transformation of the distal wing to the deployed configuration.
Figure 36:
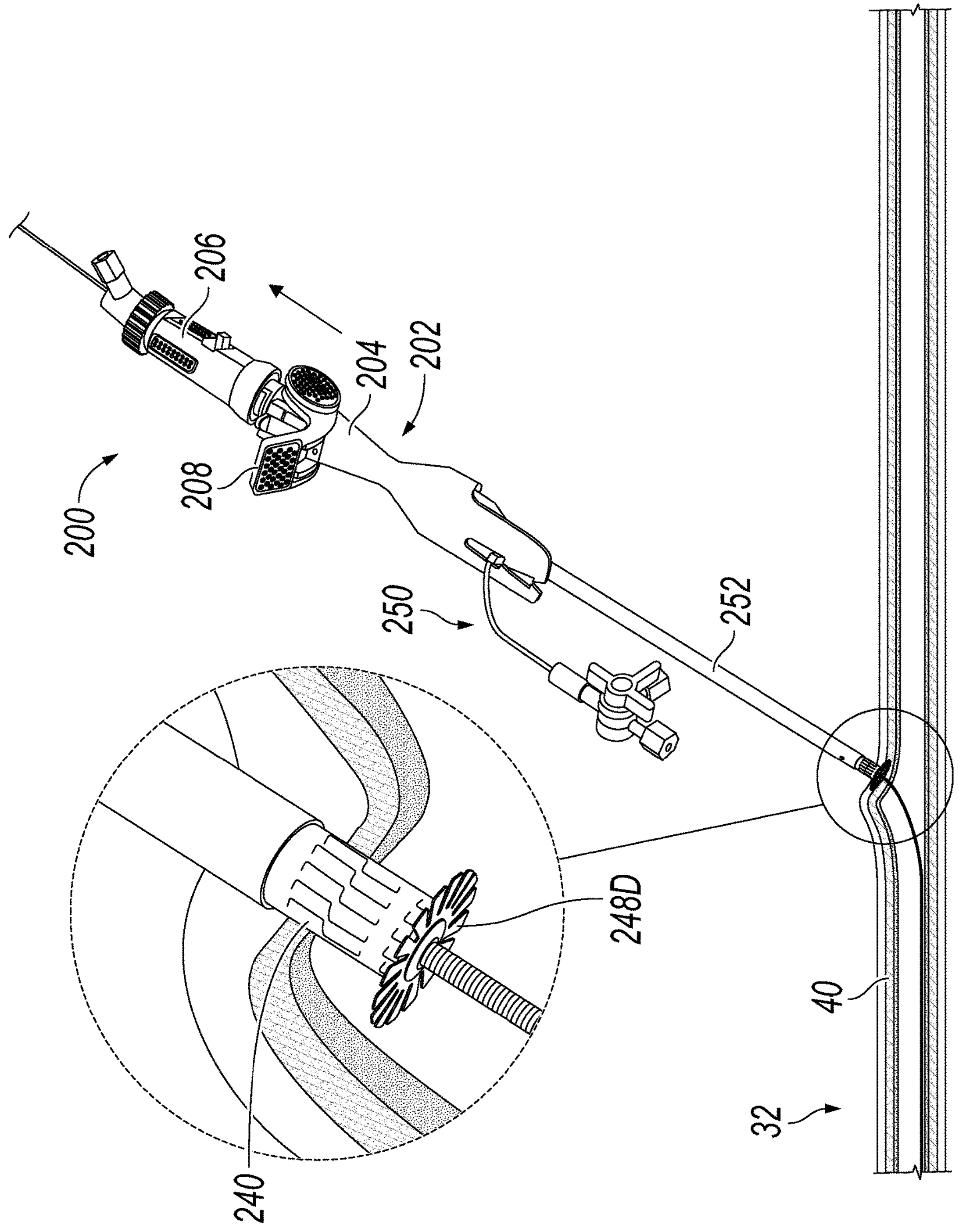
FIG. 36 is a perspective view of the actuator assembly of FIG. 19 with the distal wing being tensioned against an inner wall of the arterial lumen.

Once in position, the assembly 200 can be pivoted upward and away from a surface of the patient's tissue until an angle B between the introducer sheath 250 and the surface is at least degrees. In some embodiments, the angle B can be between approximately 50 and 60 degrees, as seen in FIG. 33, for example.

Figure 37:
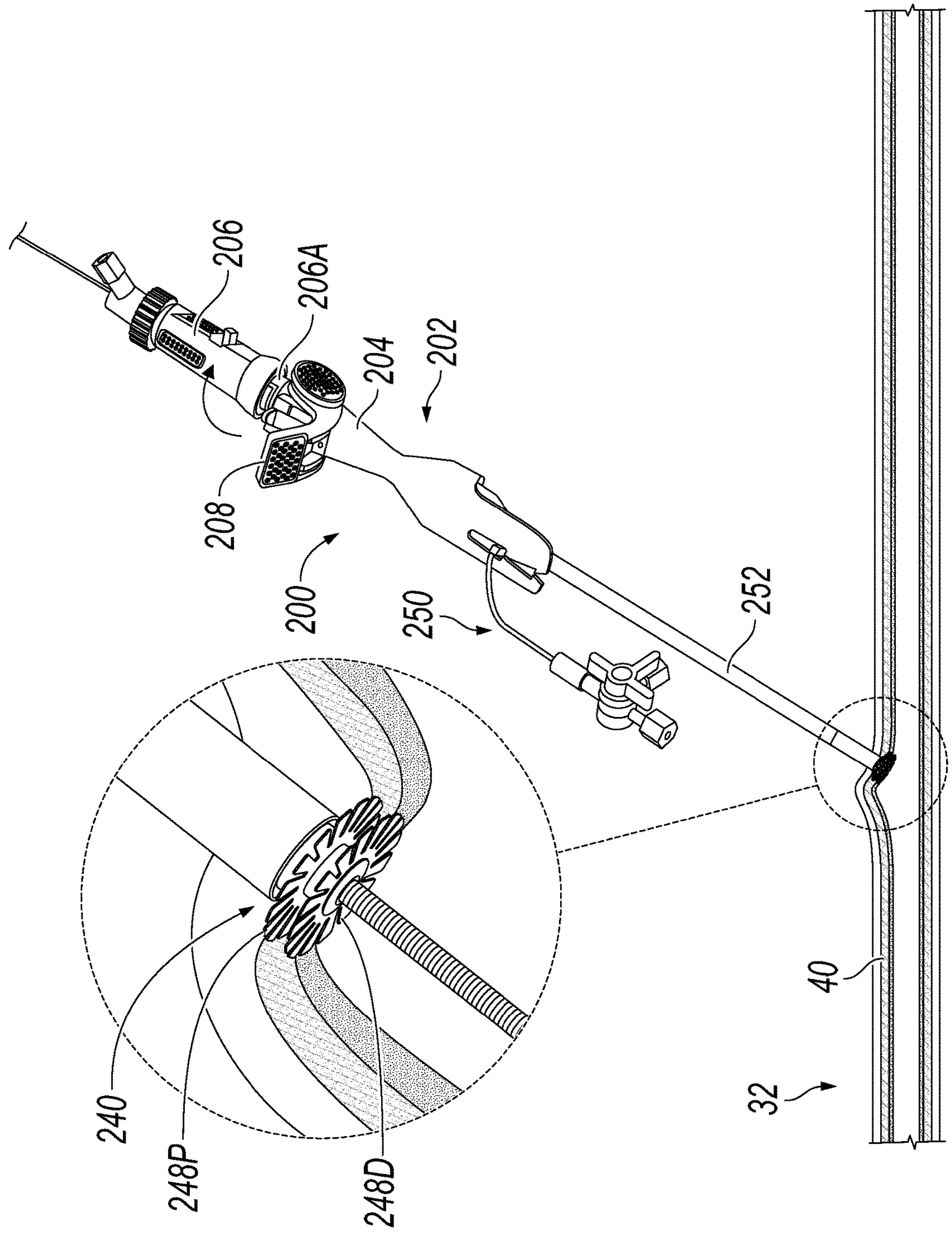
FIG. 37 is a perspective view of the actuator assembly of FIG. 19 with a proximal wing being transformed to a deployed configuration.
Figure 38:
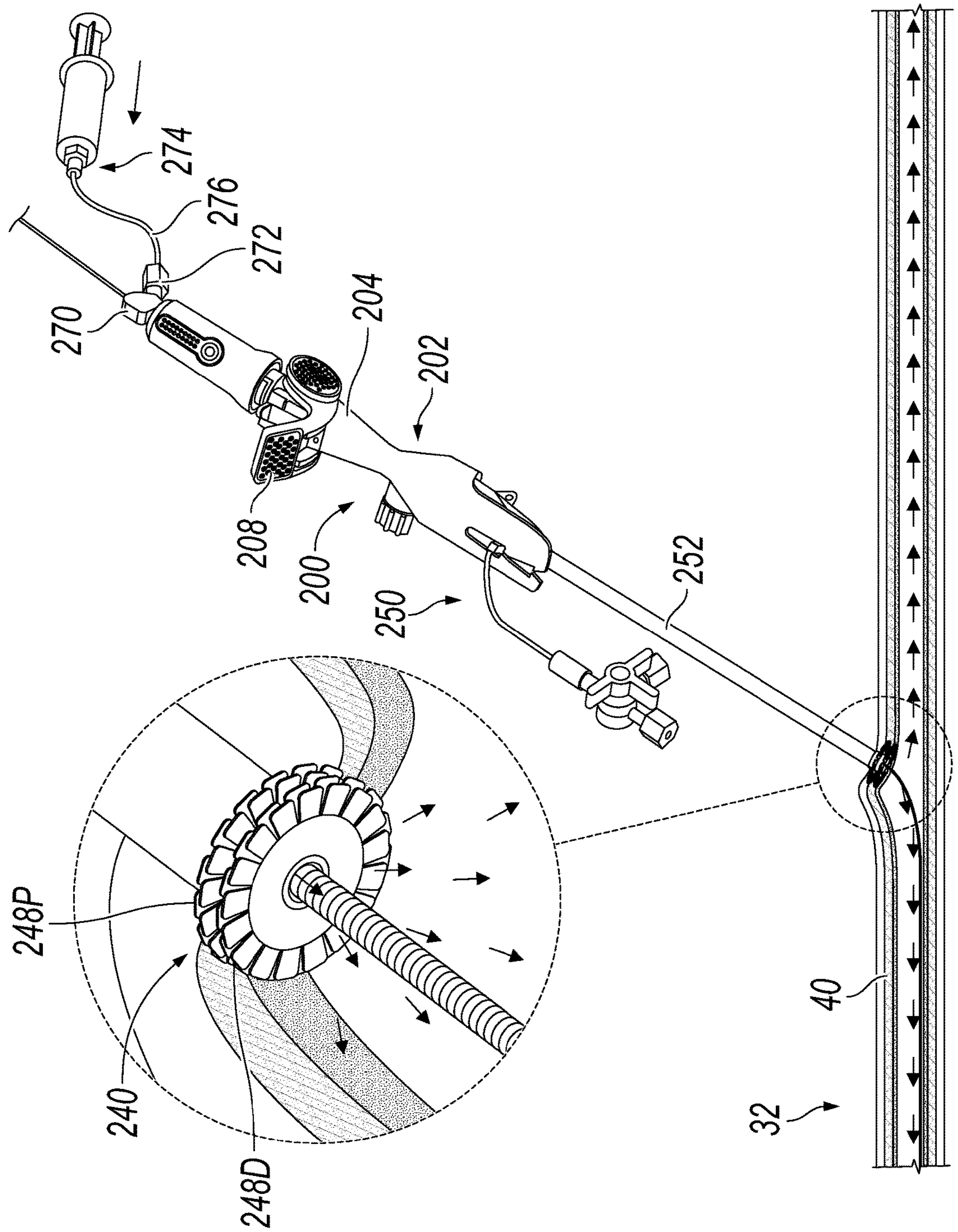
FIG. 38 is a perspective view of a contrast agent being injected through the actuator assembly of FIG. 19 following transformation of the proximal wing to the deployed configuration.

If included, while in the elevated position, the removable sheath stop 213 can be removed from the actuator assembly 200, and the introducer sheath 250 can be and locked within the second engagement zone 232A in the central track, thereby exposing the coupler 240 from a distal end of the introducer assembly 250. While maintaining the elevated angle, the locking tab 210 can be removed and the handle 206 of the actuator 202 can be rotated in a first direction (e.g., clockwise) to deploy the distal wing 248D of the coupler 240 within the arterial lumen 32. Deployment of the distal wing 248D can be observed under fluoroscopy, ultrasound, angiography and/or other imaging techniques. Successful deployment of the distal wing 248D can result in the handle 206 advancing proximally to create a gap 206A between the handle 206 and the body 204 of the actuator 202. Once the distal wing 248D is deployed, the assembly can be withdrawn until resistance is felt, indicating that the distal wing 248D has contacted an inner surface of the arterial lumen 32. While maintaining this resistance, the handle 206 can be actuated in a second direction (e.g., counter-clockwise) opposite the first direction to deploy the proximal wing 248P and "sandwich" tissue 40 between the distal wing 248D and proximal wing 248P, as seen in FIG. 37. Deployment of the proximal wing 248P can be observed under fluoroscopy or under ultrasound. After deployment of the proximal wing 248P, the gap 206A between the handle 206 and the body 204 of the actuator 202 can increase, providing further confirmation of successful deployment.

The contrast port 270, can be connected to the actuator assembly 200 in advance of the procedure, can be advanced over the guidewire 30. The contrast port 270 can generally include a linking arm 272 with a valve system extending therefrom. The linking arm 272 can be configured to removably couple to the handle 206 of the actuator assembly 200, such as via a luer lock, threading, a snap fit, a friction fit, etc. The valve system 274 can include a flexible tubing 276 connected to the linking arm 272 at one end and connected to a valve 274 at the other. The contrast port 270 can include a flow path (not shown) therethrough that can be in fluid communication with the central lumen 203 of the actuator assembly 200. During a surgical procedure, contrast fluid or other fluid can be injected into the valve 274 and then flow through the tubing 276, the linking arm 272 and the central lumens 203, 242. The injected contrast fluid can be used to check for leaks or improper coupling, etc. The linking arm 272 can be coupled and decoupled to the handle 206 as needed during a surgical procedure.

Contrast fluid can be injected through the contrast port 270 to confirm that the arterial lumen 32 is in proper condition prior to plugging the central lumen 242 of the coupler 240 and while the guidewire is still in place. If the contrast fluid indicates an issue, such as damage to the arterial lumen 32, improper coupler 240 positioning, etc., the coupler 240 can be returned to the delivery configuration, if necessary, or additional measures can be taken to correct the indicated issue. The process can then proceed from any point thus far, following correction.

Figure 39:
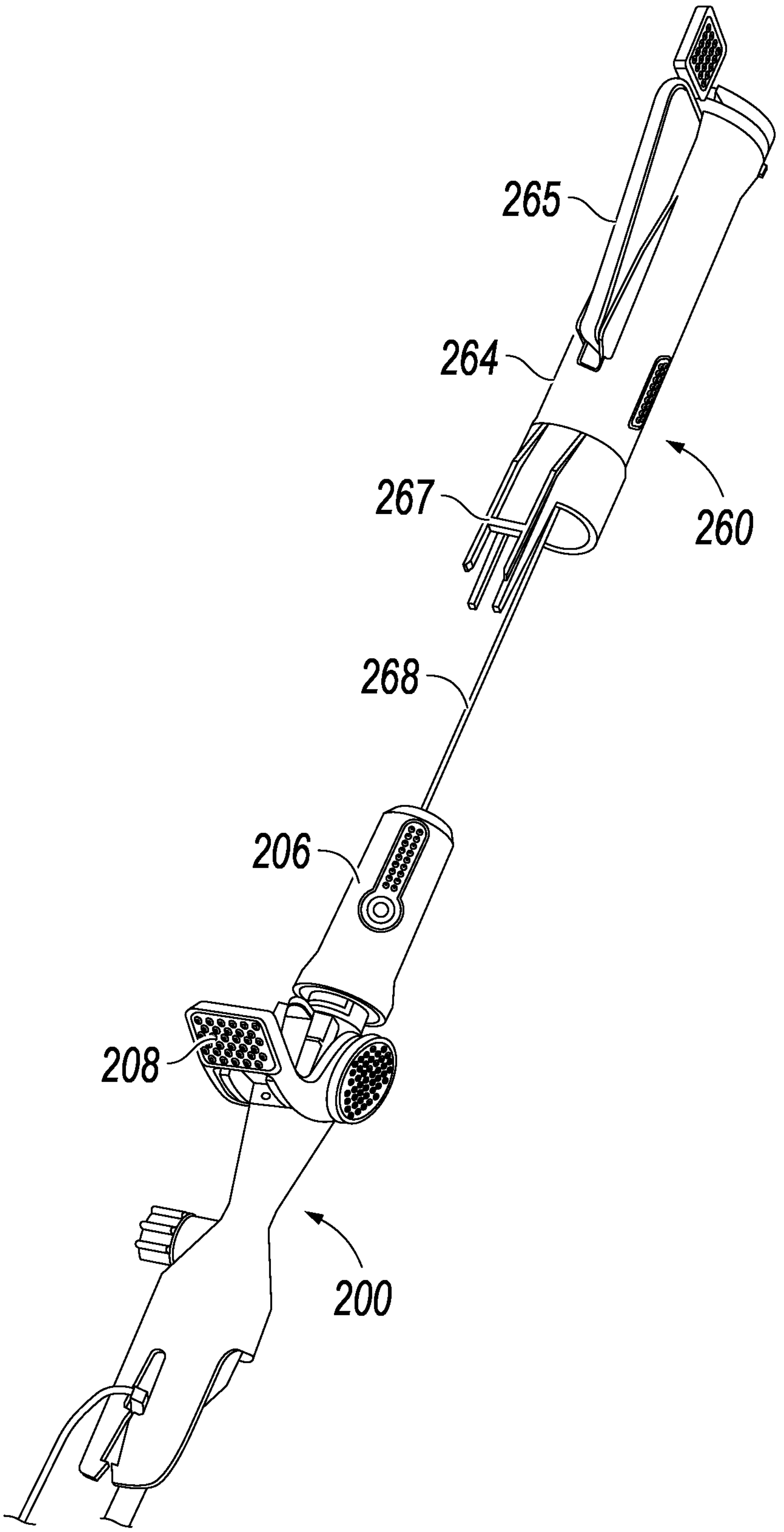
FIG. 39 is a partial perspective view of the plug tool of FIG. 30 being inserted into the actuator assembly of FIG. 19.
Figure 40:
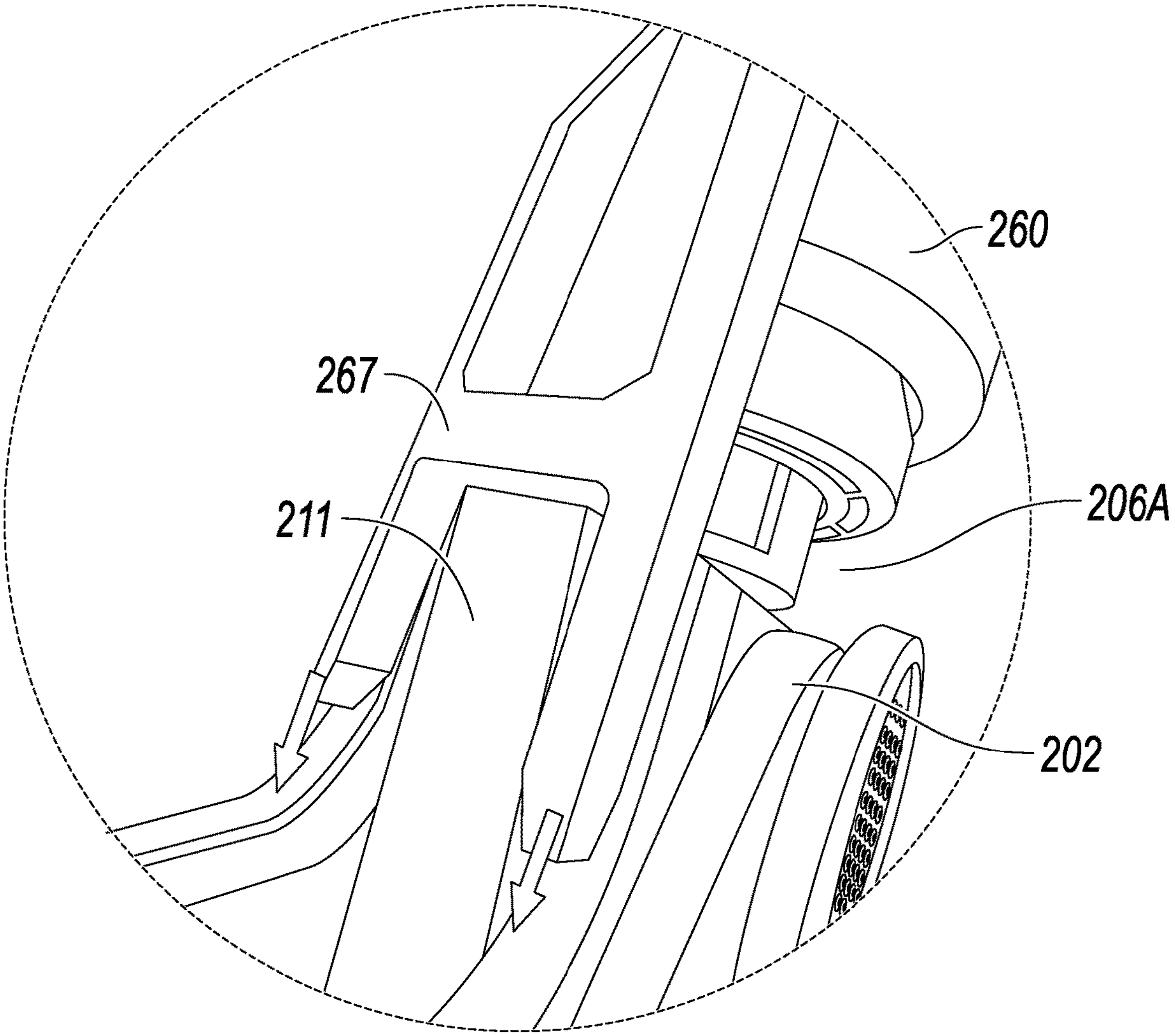
FIG. 40 is a partial perspective view of the prongs of the plug tool coupling with the removable lever lock of the actuator assembly as the plug tool is inserted into the actuator assembly, as shown in FIG. 39.
Figure 41:
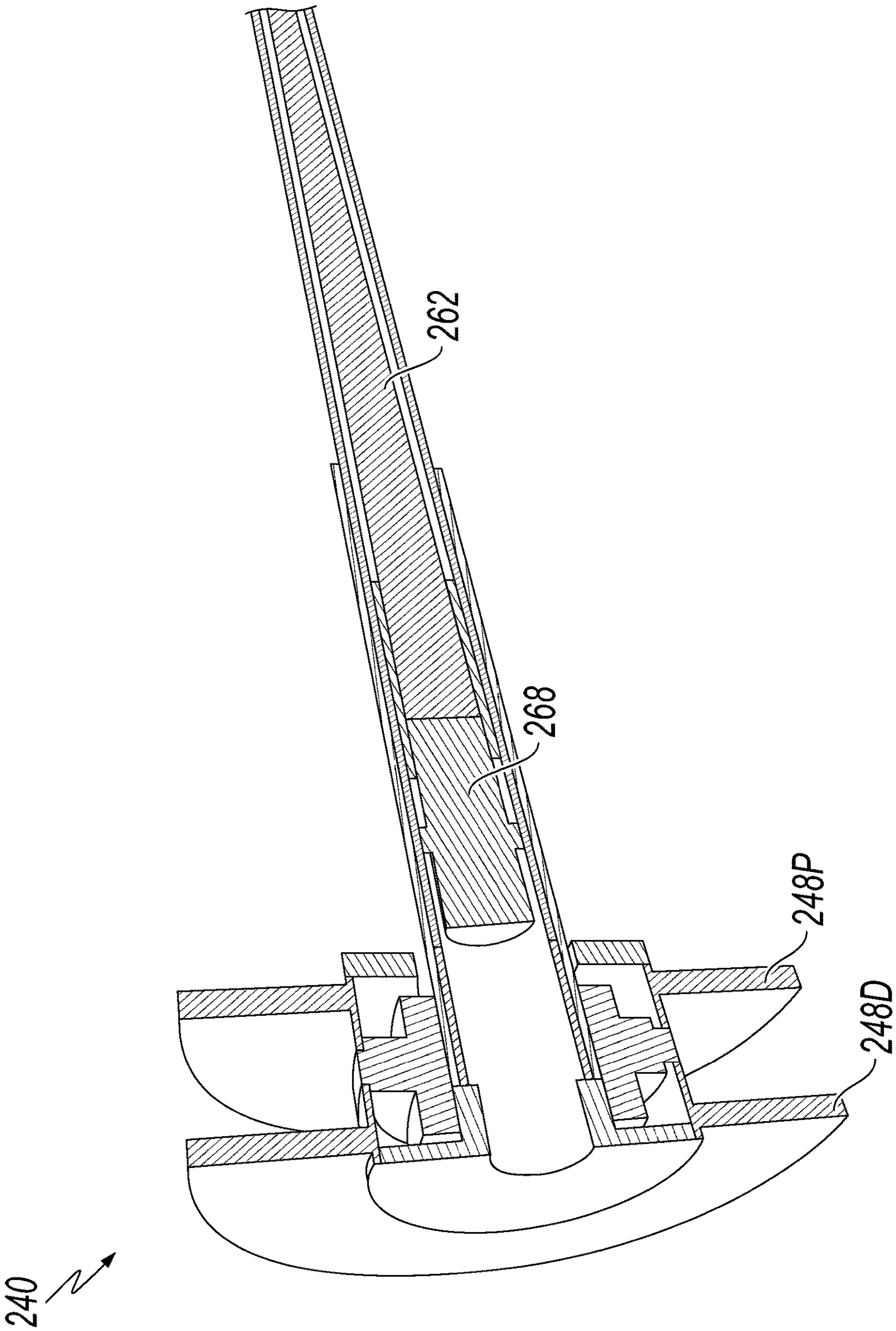
FIG. 41 is a partial cross-sectional view of the plug tool of FIG. 30, including an ejectable plug, being inserted into the central lumen of the deployed deployable coupler.
Figure 42:
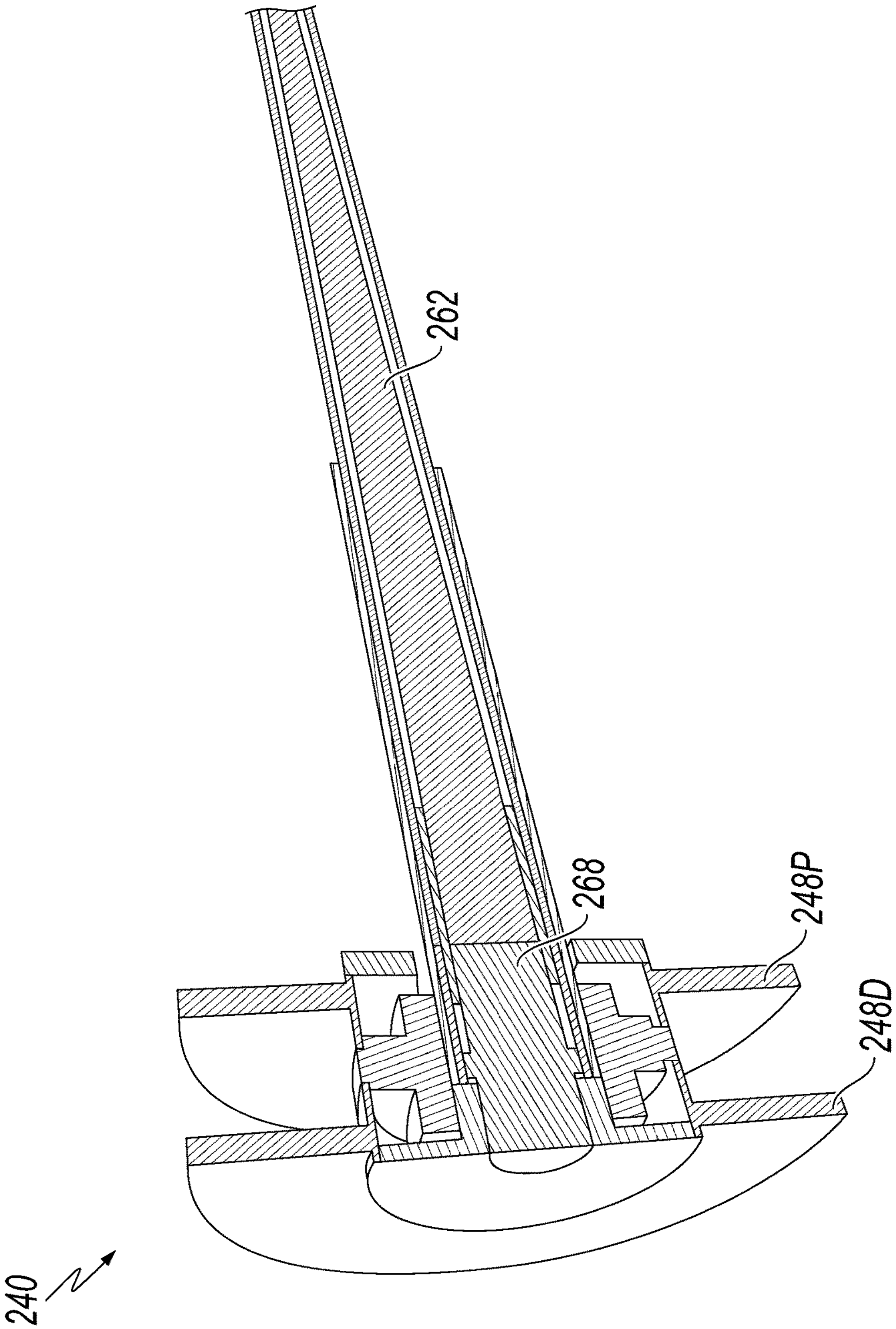
FIG. 42 is a partial cross-sectional view of the deployed deployable coupler of FIG. 41 with the ejectable plug fully inserted into the central lumen of the deployed deployable coupler.
Figure 43:
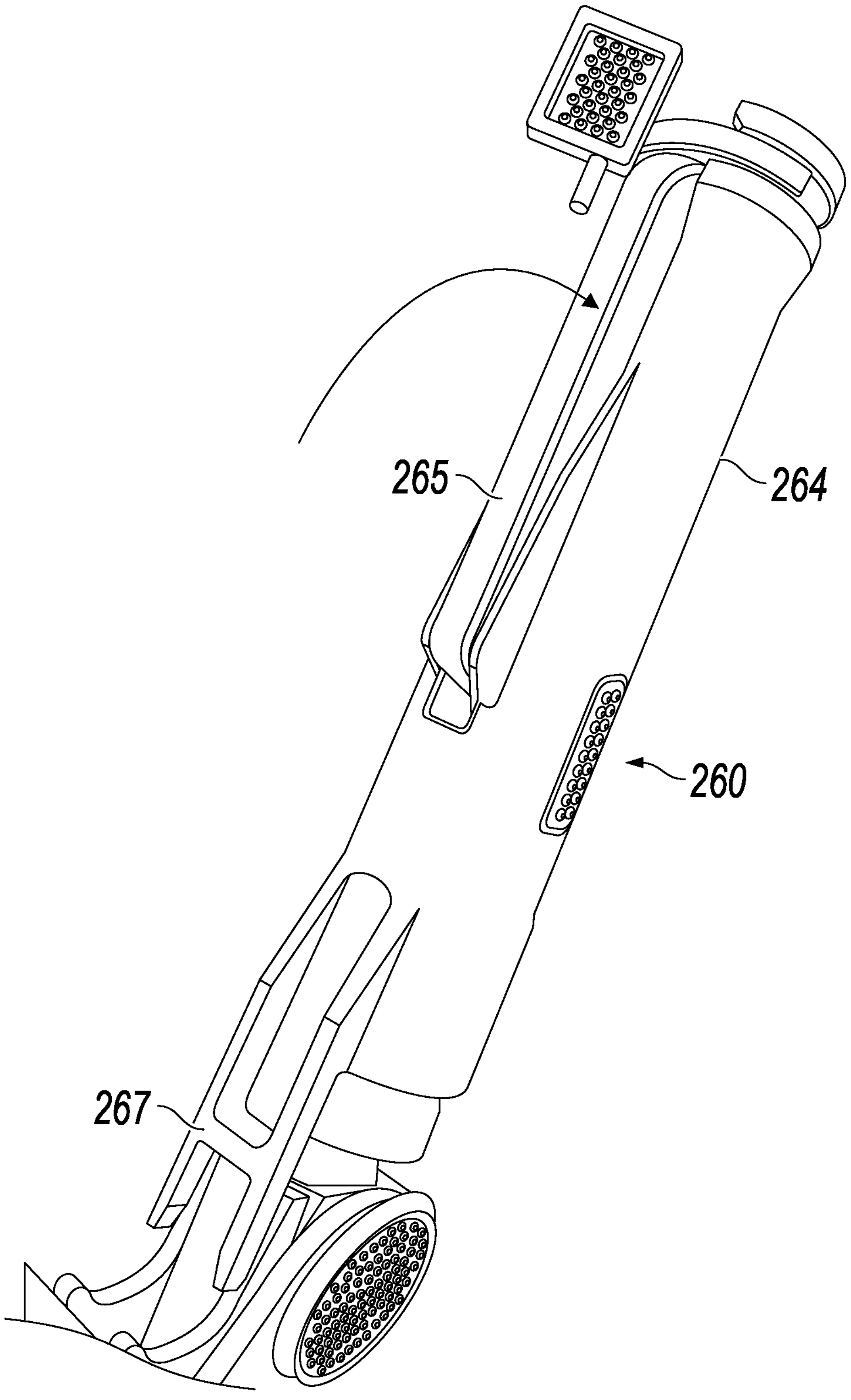
FIG. 43 is a partial perspective view of the plug tool of FIG. 30 with a plug lock moved to an unlocked position and a plug lever being actuated.
Figure 44:
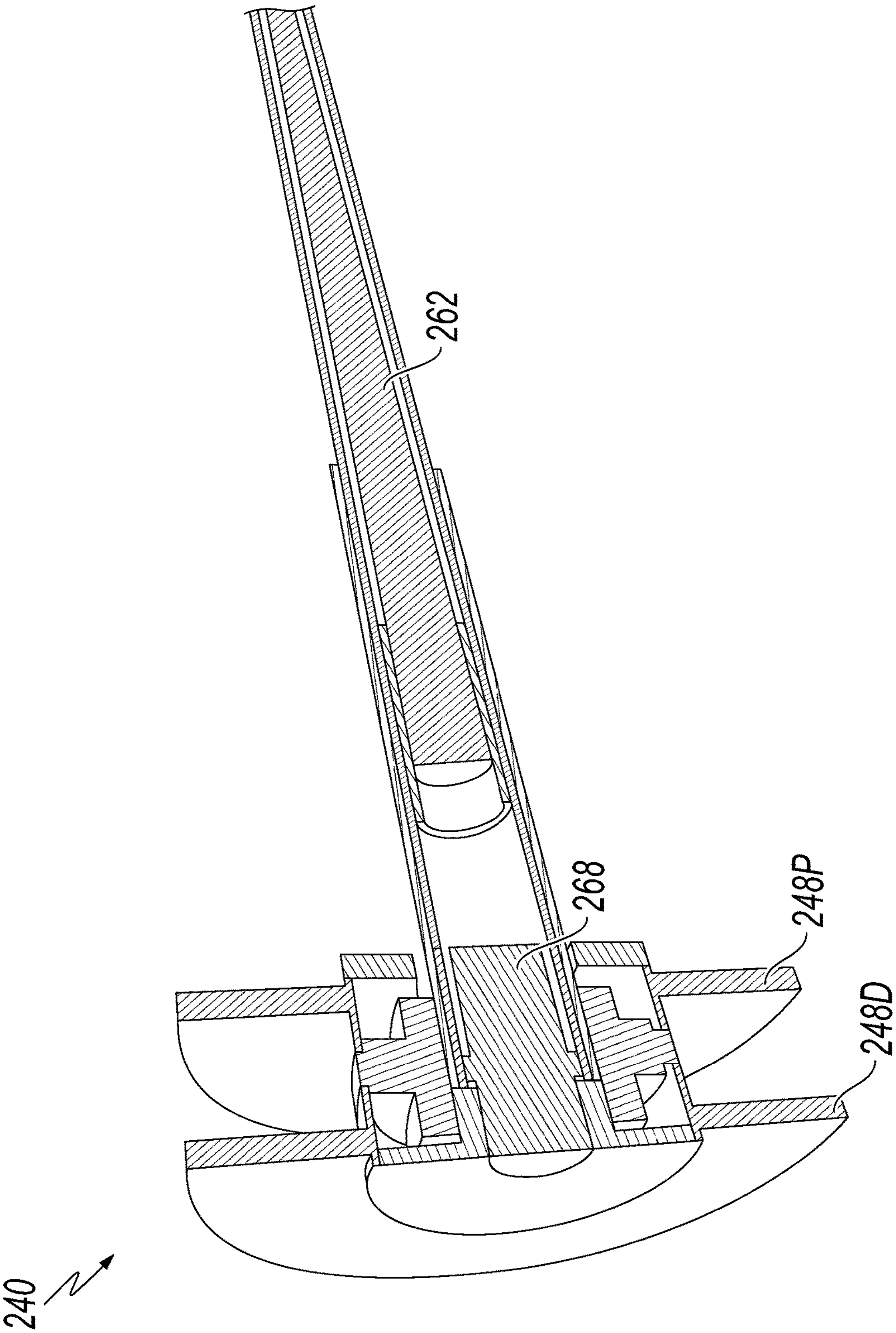
FIG. 44 is a partial cross-sectional view of the ejectable plug and deployable coupler of FIG. 42 with the ejectable plug ejected from the plug tool.
Figure 45:
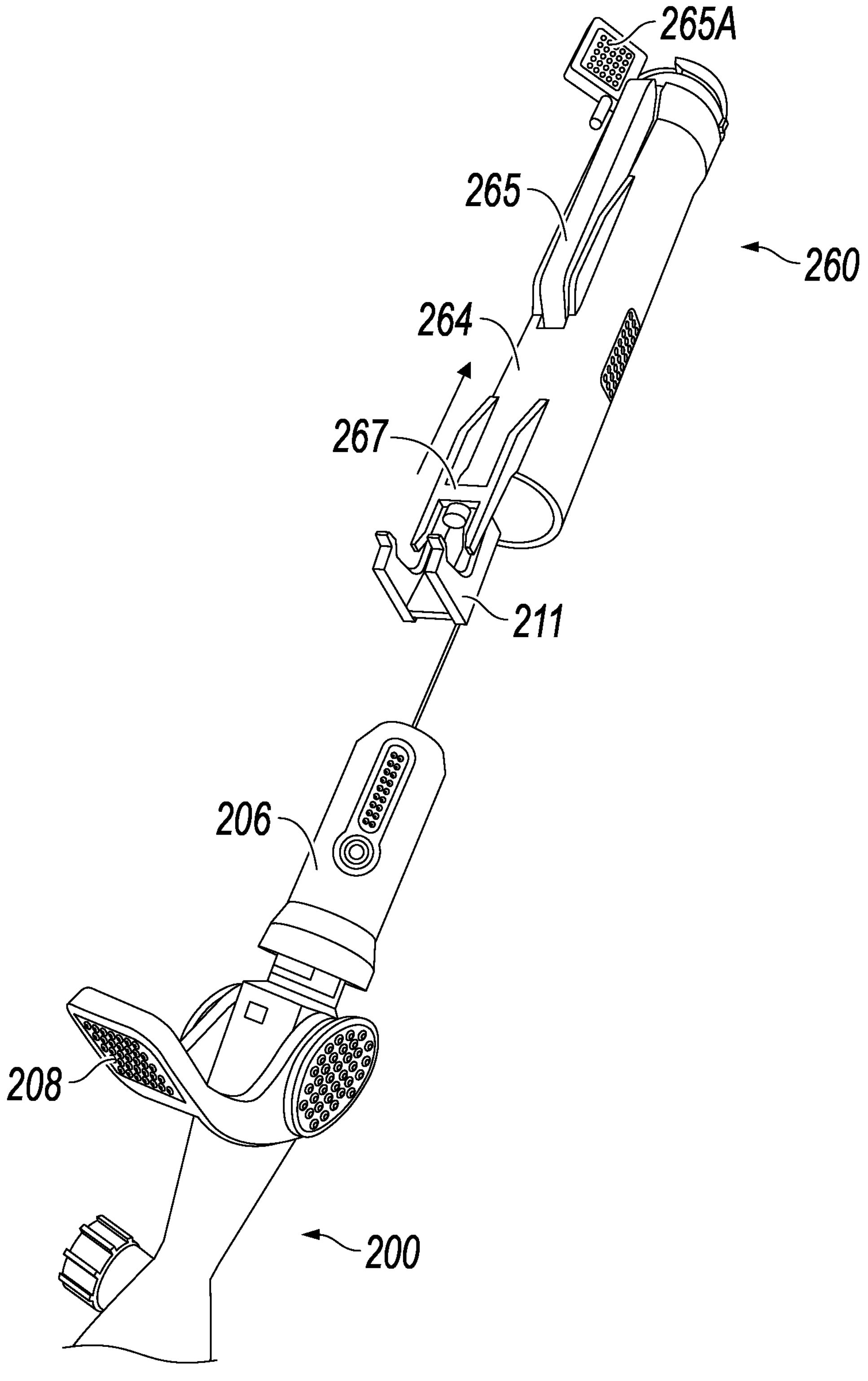
FIG. 45 is a perspective view of the plug tool of FIG. 30 being removed from the actuator assembly following ejection of the plug, the lever lock being removed with the plug tool while secured to the prongs of the plug tool.
Figure 46:
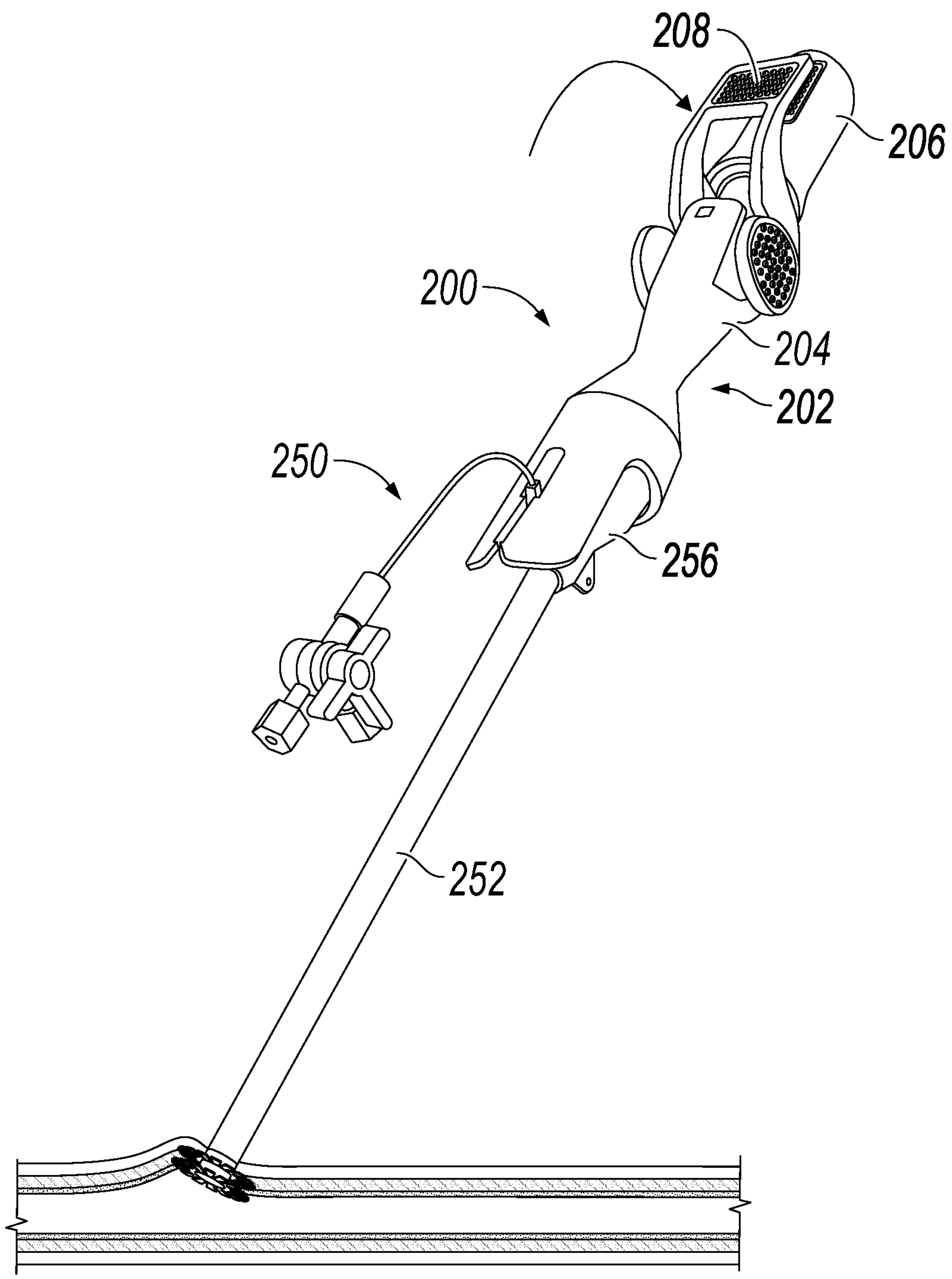
FIG. 46 is a perspective view of the closure assembly of FIG. 19 with the ejection lever actuated.
Figure 47:
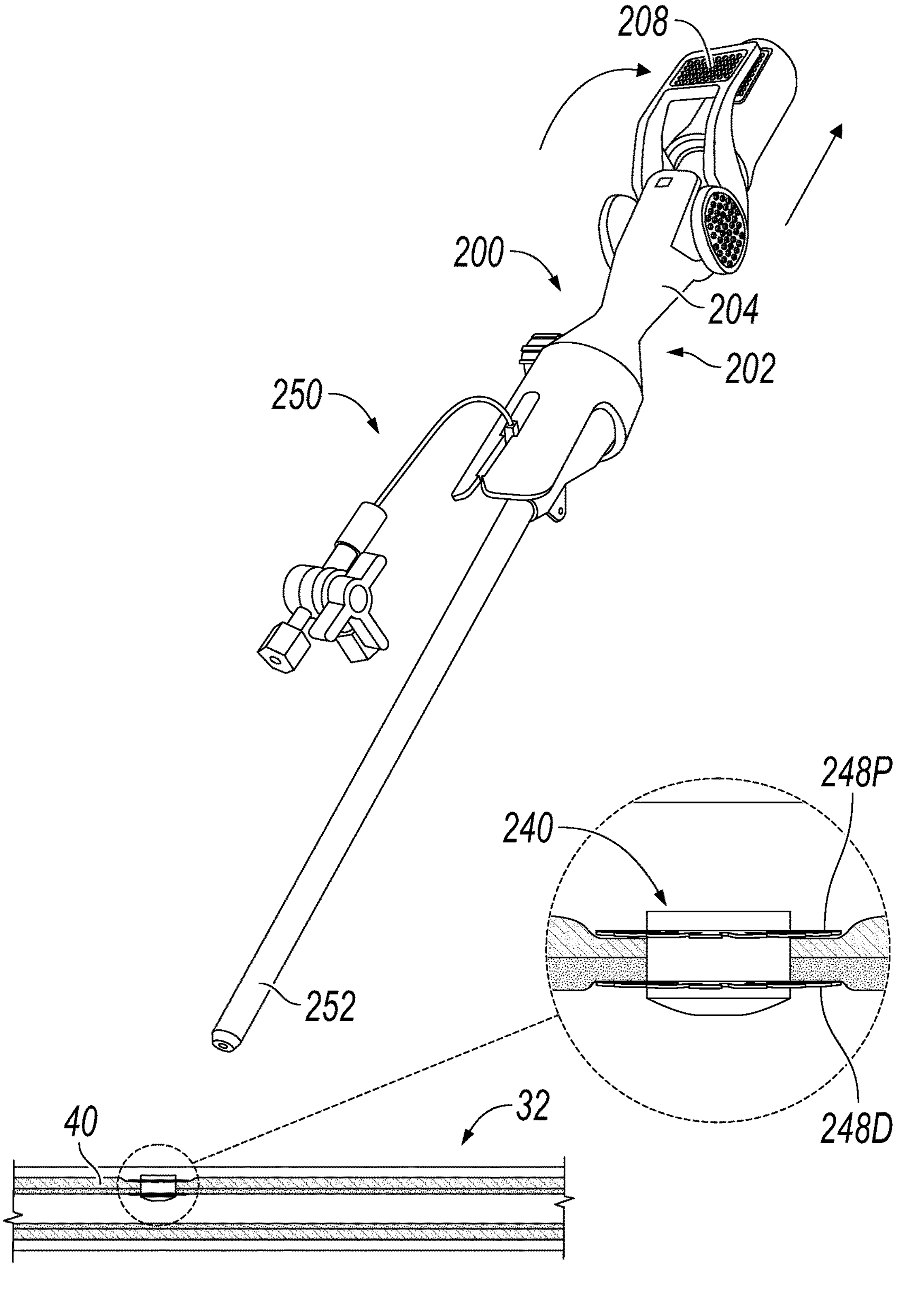
FIG. 47 is a perspective view of the closure assembly of FIG. 19 being removed from a surgical site following the deployment of the deployable coupler.

In embodiments relying upon the use of the contrast port 270, following injection of contrast and confirmation of position, or if the contrast port 270 is not used, the procedure can proceed. The guidewire 30 and the contrast port 270 can be removed from the actuator assembly 200, and the plug tool 260 can advance the ejectable plug 268 into the proximal end of the actuator 202. The plug tool 260 can be advanced so that the handle 206 of the actuator 202 is fully received by the distal crevice 266 of the plug tool 260 and the prongs 267 couple with the removable lever lock 211, as seen in FIGS. 39-40. This full insertion can also position the ejectable plug 268 securely within the central lumen 242 of the coupler 240, as seen in FIGS. 41-42. Once the plug tool 260—and the ejectable plug 268, in turn—are properly positioned, the plug lock 265A can be rotated about the distal end of the plug tool 260 to decouple with the lever 265, and the lever 265 can be actuated to eject the ejectable plug 268 from the plug shaft 262, as seen in FIGS. 43-44. Once the ejectable plug 268 is ejected, the plug tool 260 can be removed from the actuator 202 by sliding the plug tool 260 in a proximal direction. Removal of the plug tool 260 may not decouple the prongs 267 from the removable lever lock 211, such that removal of the plug tool 260 also removes the removable lever lock 211 from its position affixed to the lever 265, as seen in FIG. 45. With the plug tool 260 removed, the ejection lever 208 can be actuated to decouple the coupler 240 from the elongate shaft 252, thereby deploying the coupler 240, as seen in FIGS. 46-47. Separation of the coupler 240 from the elongate shaft 252 can be observed under fluoroscopy, if desired. The introducer sheath 250 and the actuator 202 can be removed from the patient.

Figure 48:
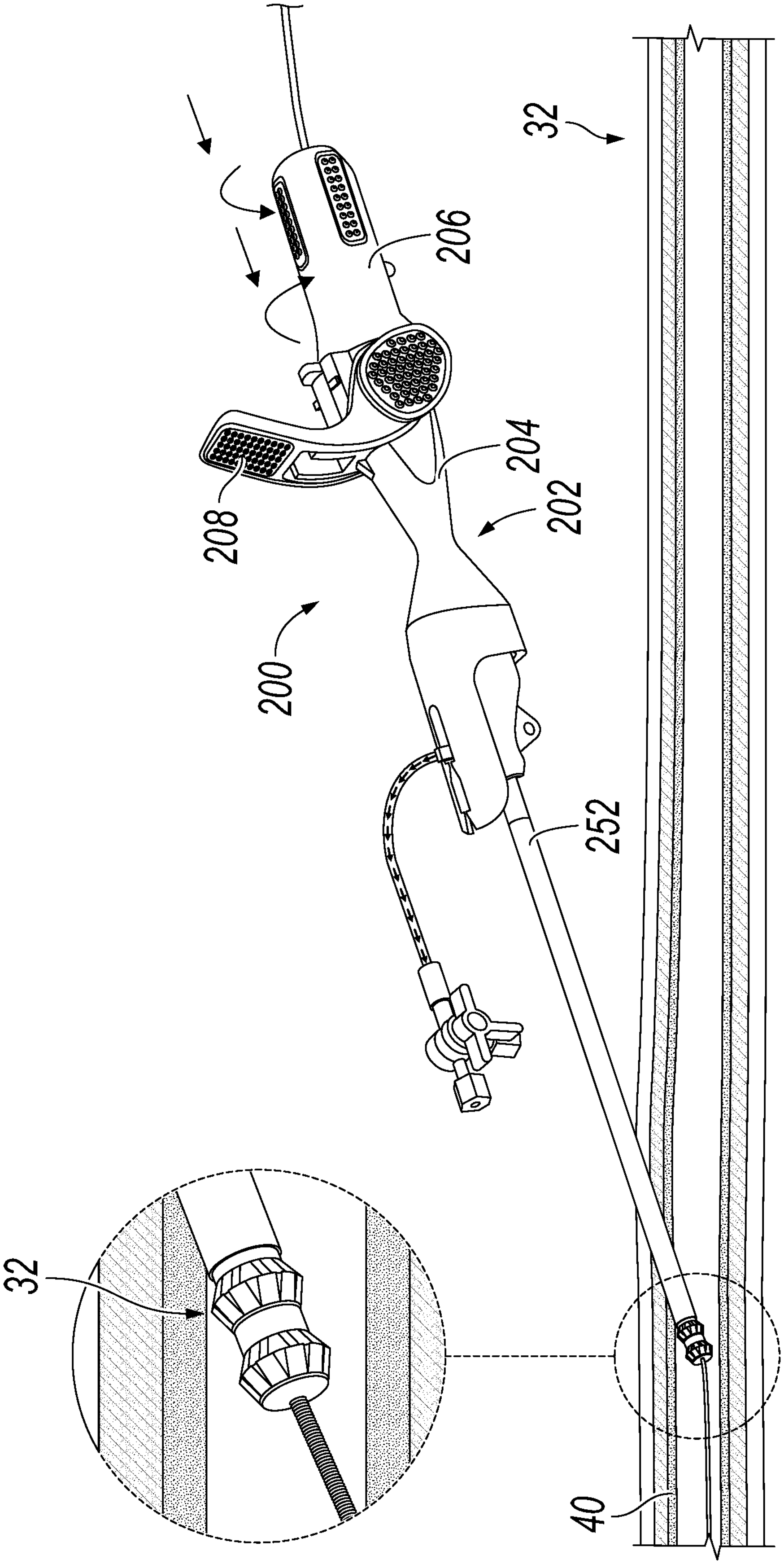
FIG. 48 is a perspective view of the closure assembly of FIG. 19 showing improper deployment of the proximal and distal wings of the deployable coupler being returned to a partial-delivery configuration following premature deployment of the proximal and distal wings within the arterial lumen.
Figure 49:
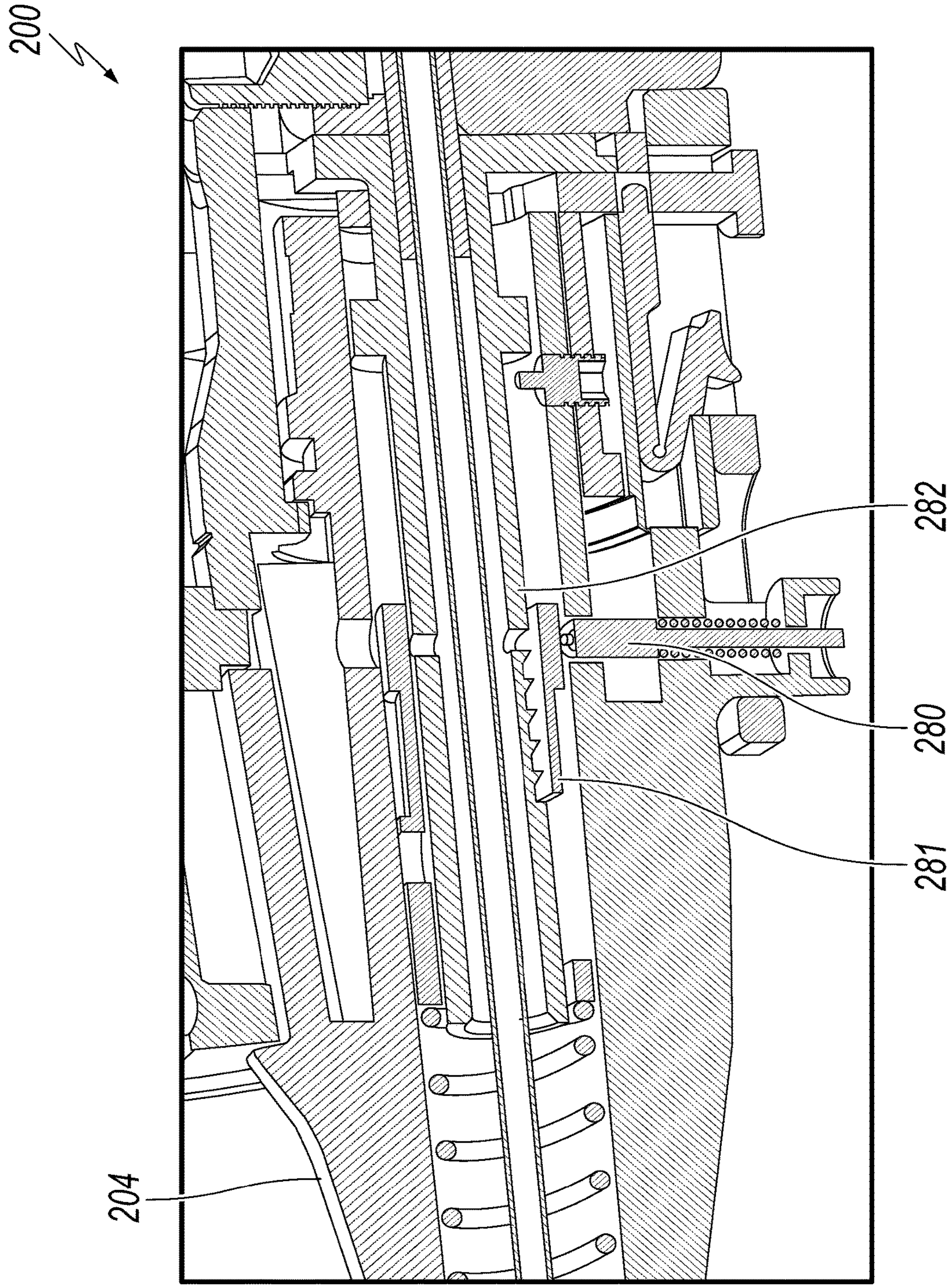
FIG. 49 is partial cross-sectional view of the closure assembly of FIG. 19 during a pre-deployment position of a deployment procedure.
Figure 50:
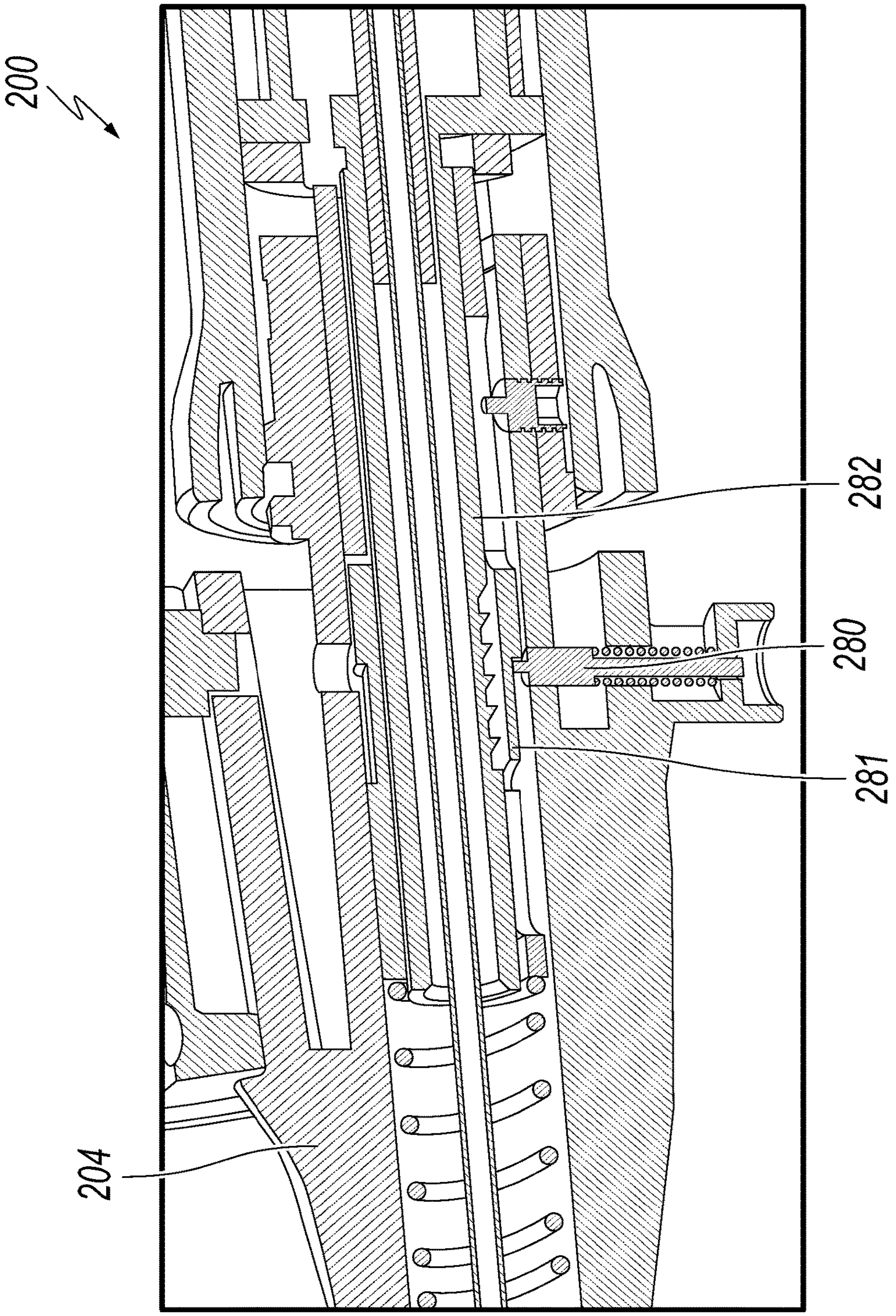
FIG. 50 is a partial cross-sectional view of the closure assembly of FIG. 19 during a first wing deployment step in the deployment procedure of FIG. 49.
Figure 51:
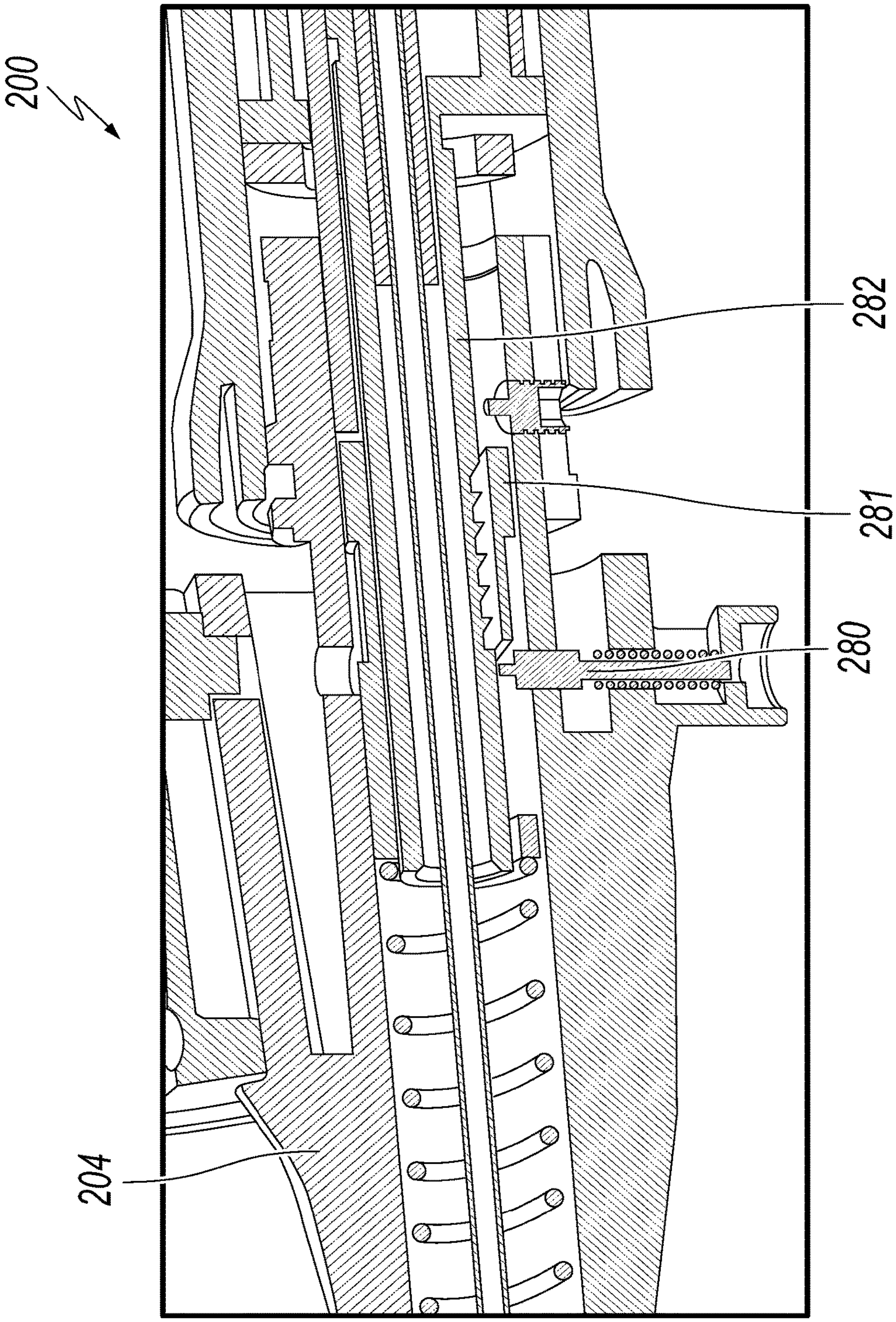
FIG. 51 is a partial cross-sectional view of the closure assembly of FIG. 19 during a second wing deployment step in the deployment procedure of FIG. 49.

During surgical procedures, the coupler 240 can be incorrectly deployed entirely within an arterial lumen 32, also known as "total intra-arterial deployment." If this deployment occurs, the coupler 240 can be collapsed to a substantially pre-deployment state and then removed from the patient, leaving the guidewire 30 in place. FIGS. 48-55 depict a collapse procedure taking place in such an event and provide an internal view of a mechanism used to deploy and collapse the coupler 240, which can simultaneously lock out future deployments of the coupler 240. FIG. 49 depicts an internal view of the actuator assembly 200 in a pre-deployment position. In this position, the locking tab 210 is in place. FIG. 50 depicts the actuator assembly 200 following deployment of the first of either the proximal or distal wing 248P, 248D (depending upon which wing is deployed first for the procedure), and the gap 206A can be clearly seen. In this position, a guide pin 280 locks into position on the actuator cylinder 281 of an actuator 282, preventing the handle 206 from moving forward. FIG. 51 depicts the actuator assembly 200 following the deployment of the second of either the proximal or distal wing 248P, 248D and the gap 206A can be seen having grown in size as compared to FIG. 50. In this position, the guide pin 280 is again locked into position directly in front of the actuator cylinder 281 of the actuator 282, preventing the handle 206 from moving forward. At this point, if the coupler 240 is deployed correctly, the procedure can continue as desired. If the coupler 240 must be collapsed, for example, as a result of incorrect deployment, the collapse procedure can proceed.

Figure 52:
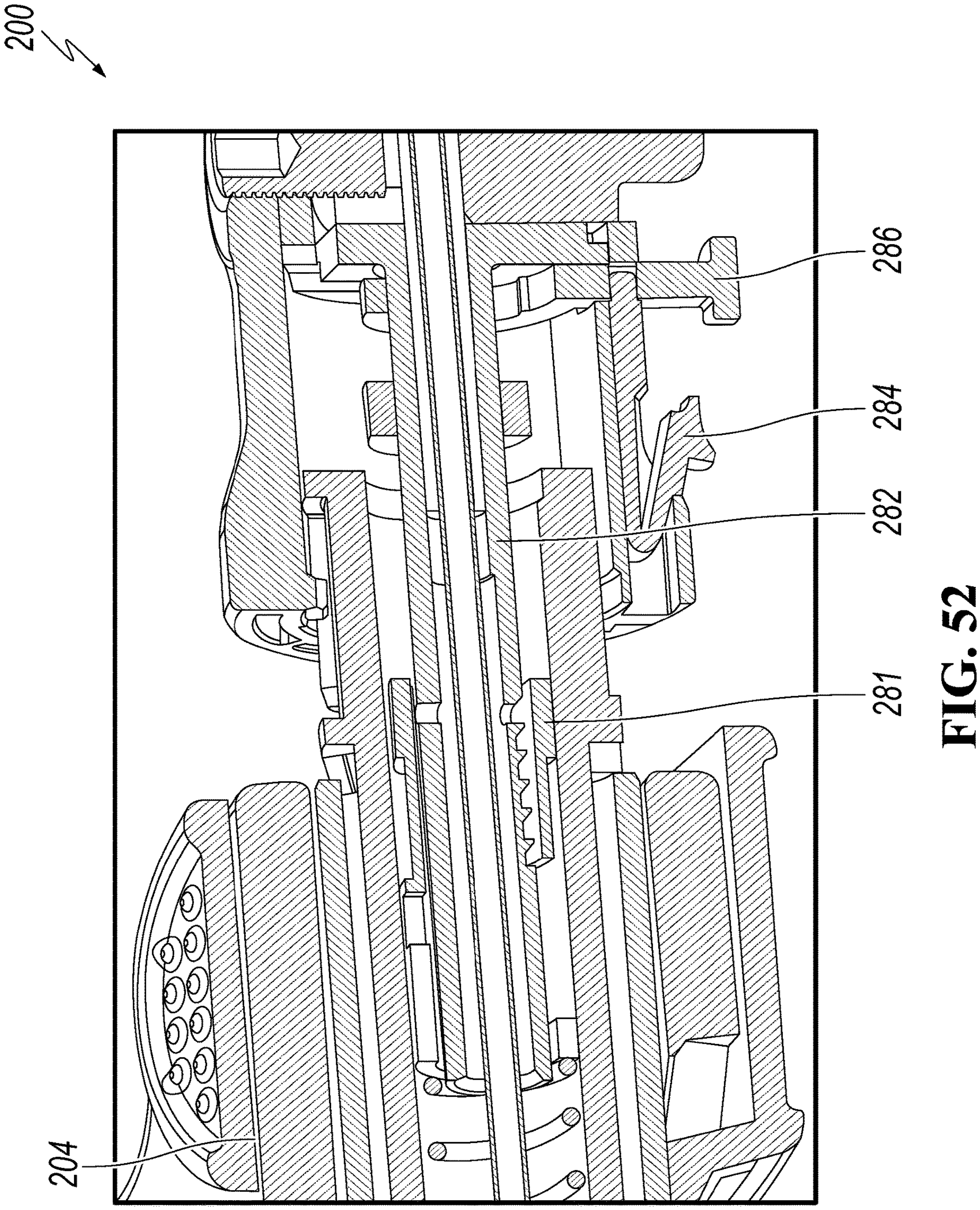
FIG. 52 is a partial cross-sectional view of the closure assembly of FIG. 19 during a first phase of an initiation of a spring release tension mechanism in the deployment procedure of FIG. 49.
Figure 53:
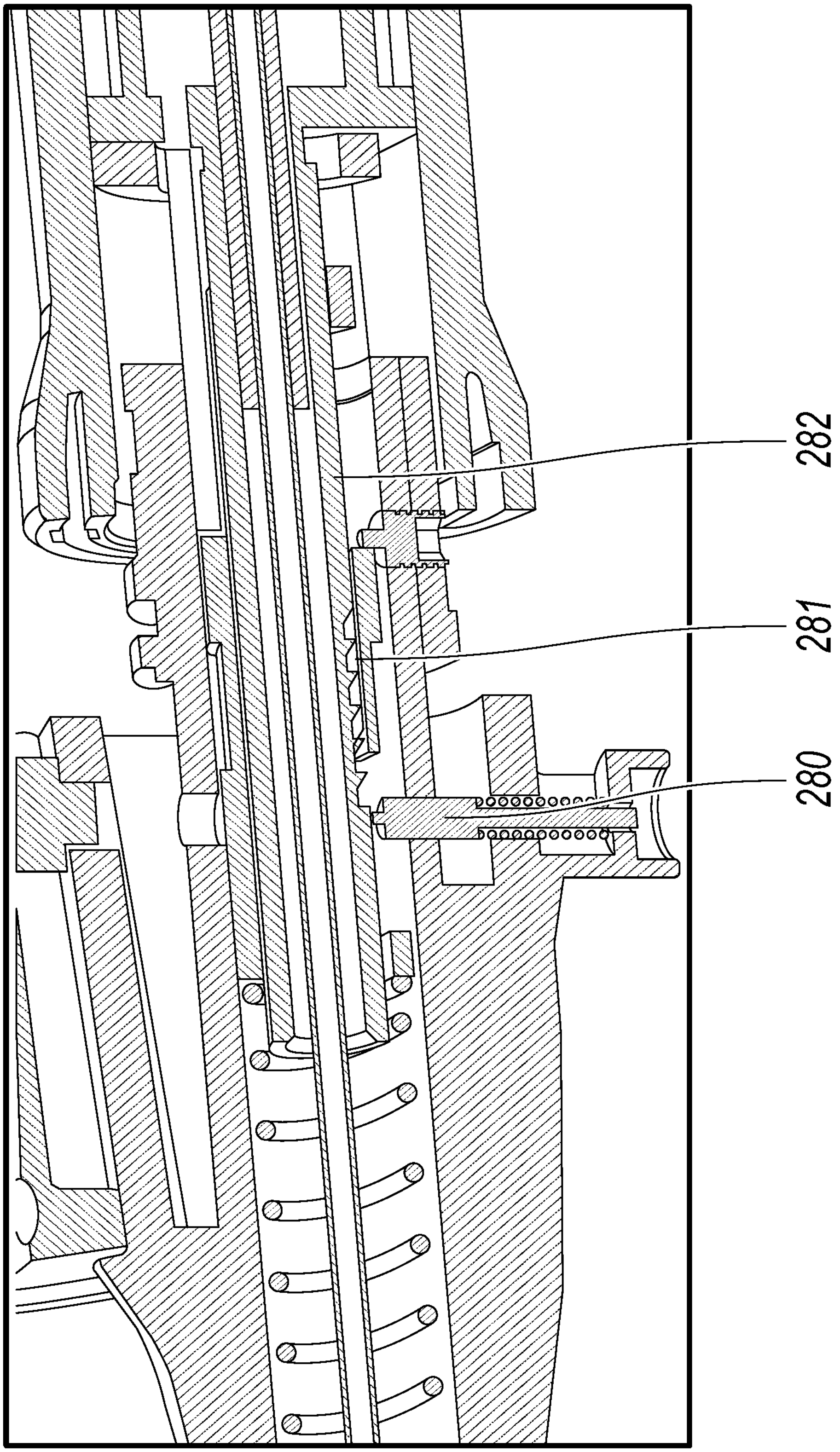
FIG. 53 is a partial cross-sectional view of the closure assembly of FIG. 19 during a second phase of the initiation of the spring release tension mechanism of FIG. 52.
Figure 54:
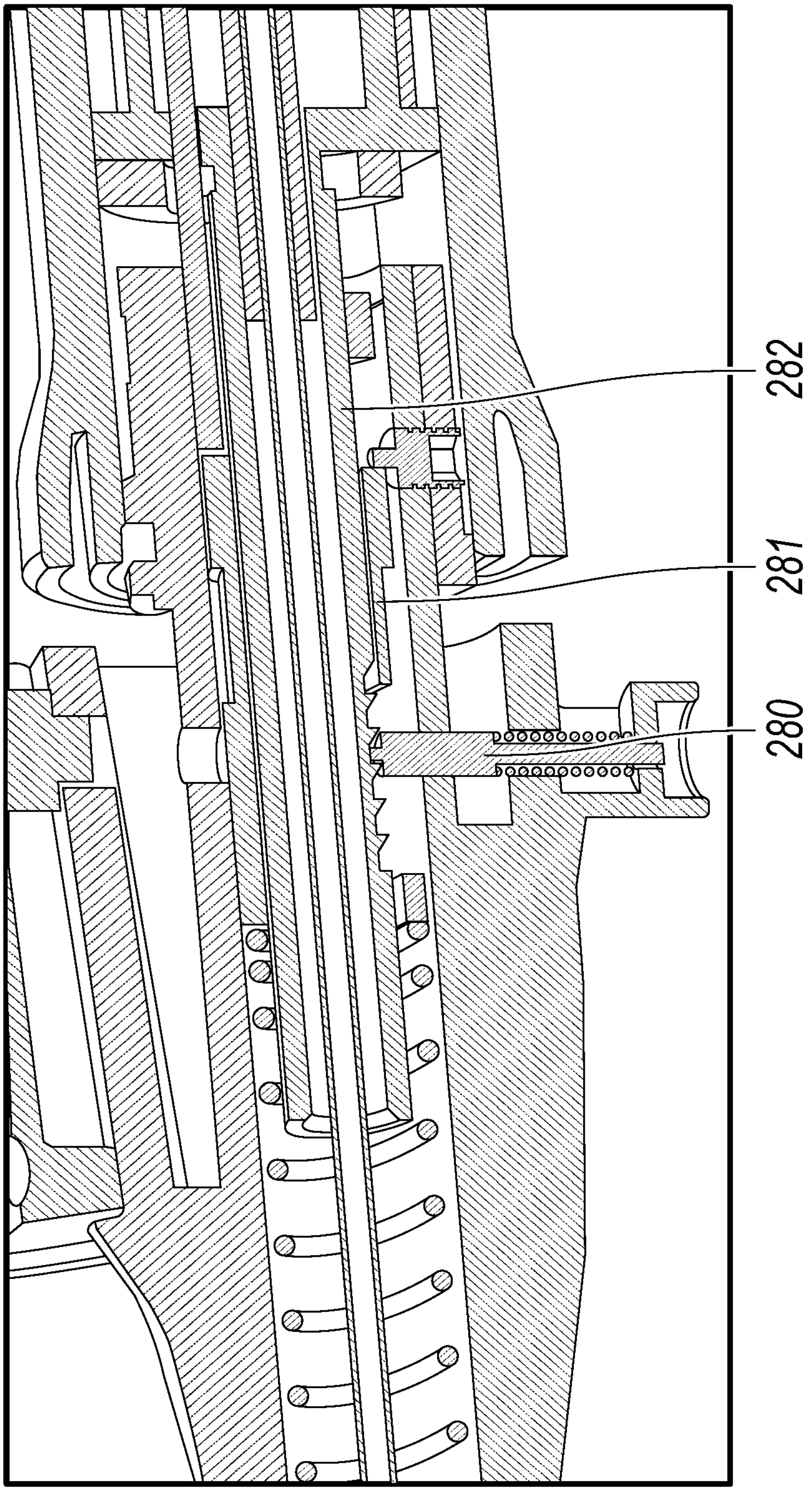
FIG. 54 is a partial cross-sectional view of the closure assembly of FIG. 19 during a first phase of a reset step in the deployment procedure of FIG. 49.
Figure 55:
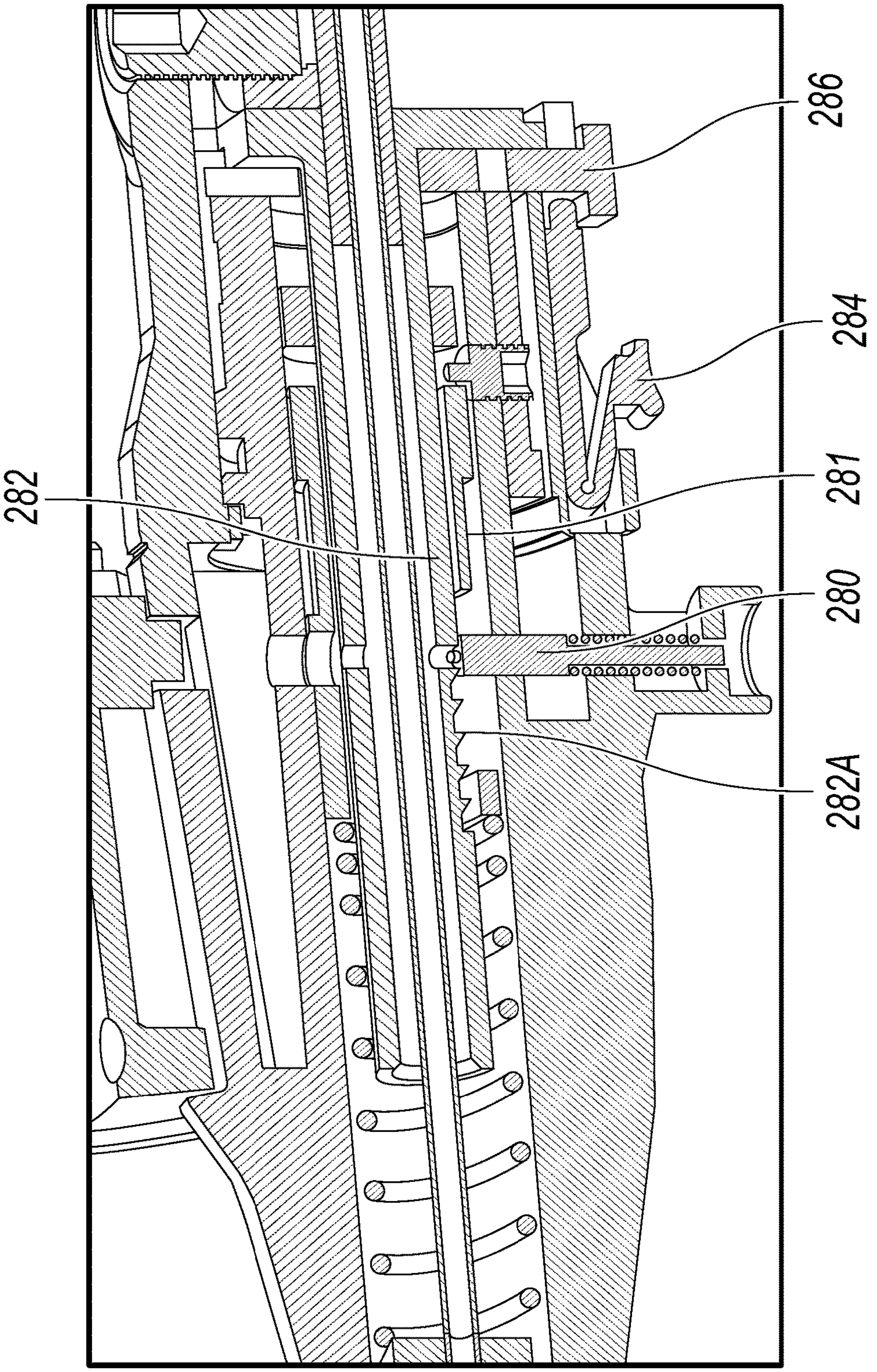
FIG. 55 is a partial cross-sectional view of the closure assembly of FIG. 19 during a second phase of the reset step of FIG. 54.

To collapse the coupler 240, as shown in FIGS. 52 and 53, a spring release plate 284 can be depressed and slid distally enable access to an actuator cylinder plate 286. The actuator cylinder plate 286 can be depressed and the actuator cylinder 282 can be unrestricted from moving distally. The handle 206 can be pushed distally and rotated in a first direction (e.g., clockwise) and then a second direction (e.g. counter-clockwise) to collapse both the proximal and distal wings 248P, 248D at the same time. The handle 206 can then be pushed distally again and rotated in a second direction (e.g., counter-clockwise) to commence/continue the collapse the other of the proximal and distal wings 248P, 248D. The proximal and distal wings 248P, 248D can be collapsed to a substantially shallow oval shape, as shown in FIG. 48, and the introducer sheath 250 and actuator assembly 200 can be removed, leaving the guidewire 30 in position. The act of collapsing the coupler 240 to the substantially pre-deployment state can cause the guide pin 280 within the actuator assembly 200 to be activated to interact with ratchets 282A located on the actuator 282 and exposed as a result of the actuator cylinder 282 remaining in a proximal position, as shown in FIG. 55. This interaction prevents redeployment of the coupler 240 following the failed initial deployment. A new actuator assembly 200 can be inserted into the patient, beginning with the first step of the procedure and proceeding from there.

Both the deployable coupler 140 and the coupler 240 are described being used in exemplary procedures to couple a portion of an arterial lumen 32. These couplers 140, 240, as well as the various embodiments described herein, can be used in a number of procedures to achieve various desired outcomes.

FIGS. 56-72 illustrate a medical procedure for promoting weight loss and/or for the treatment of Type-2 diabetes using one or more of coupler 340, according to an embodiment. The medical procedure involves a cholecystoileostomy plus or minus an entero-entero anastomosis, and it may be performed laparoscopically or percutaneously through the liver. Although reference is made to coupler 340, the described procedures may be performed with any combination of assemblies and devices described herein, including deployable coupler 140 and coupler 240. Coupler 340 can operate similarly to deployable coupler 140 and 240, and it can be used with an associated actuator assembly 300, which can operate similarly to actuator assembly 100 and actuator assembly 200.

Figure 56:
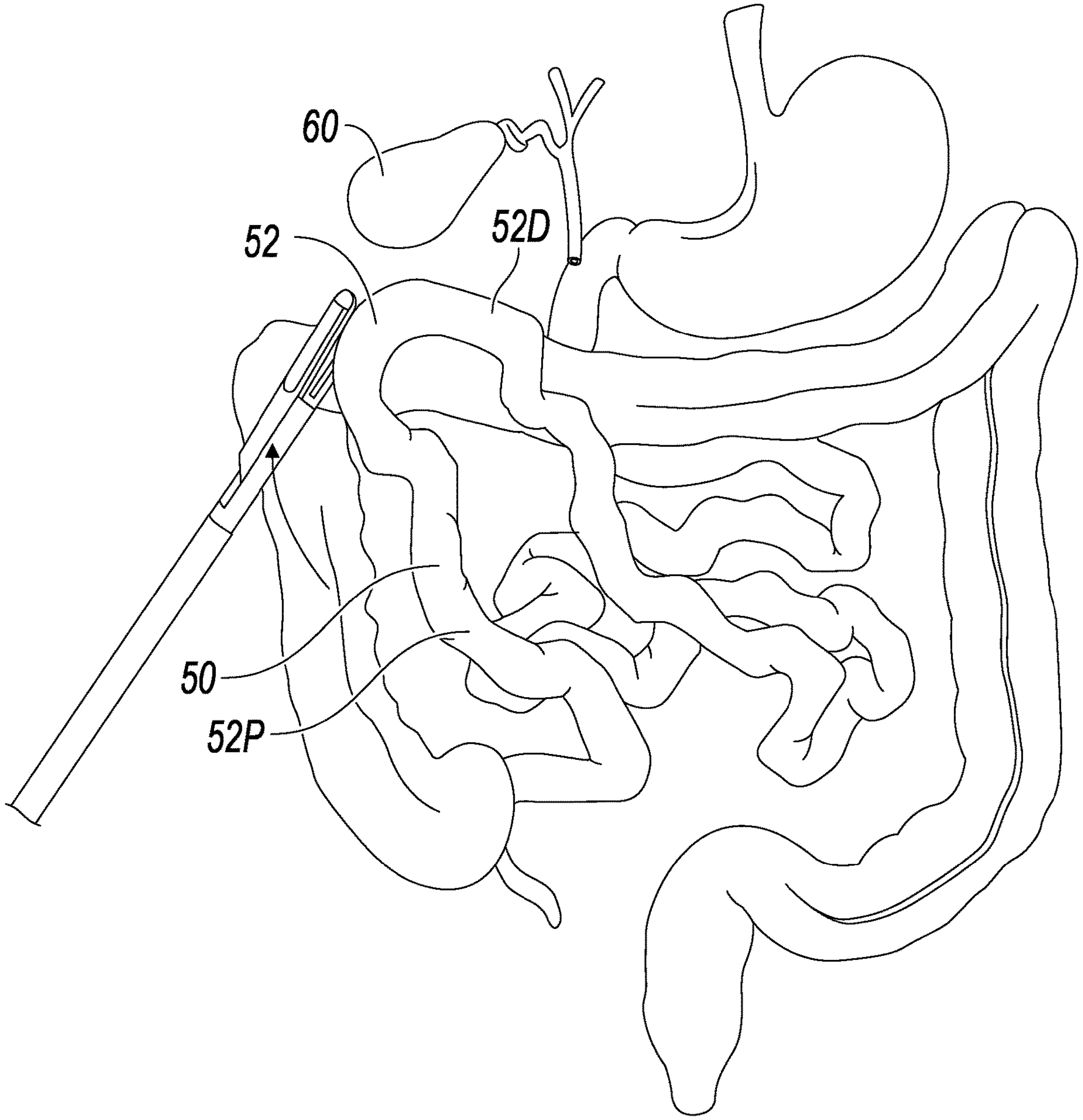
FIG. 56 is a partial front view of a digestion system of a patient in which an ileum is moved to be adjacent a gall bladder as part of a surgical procedure.
Figure 57:
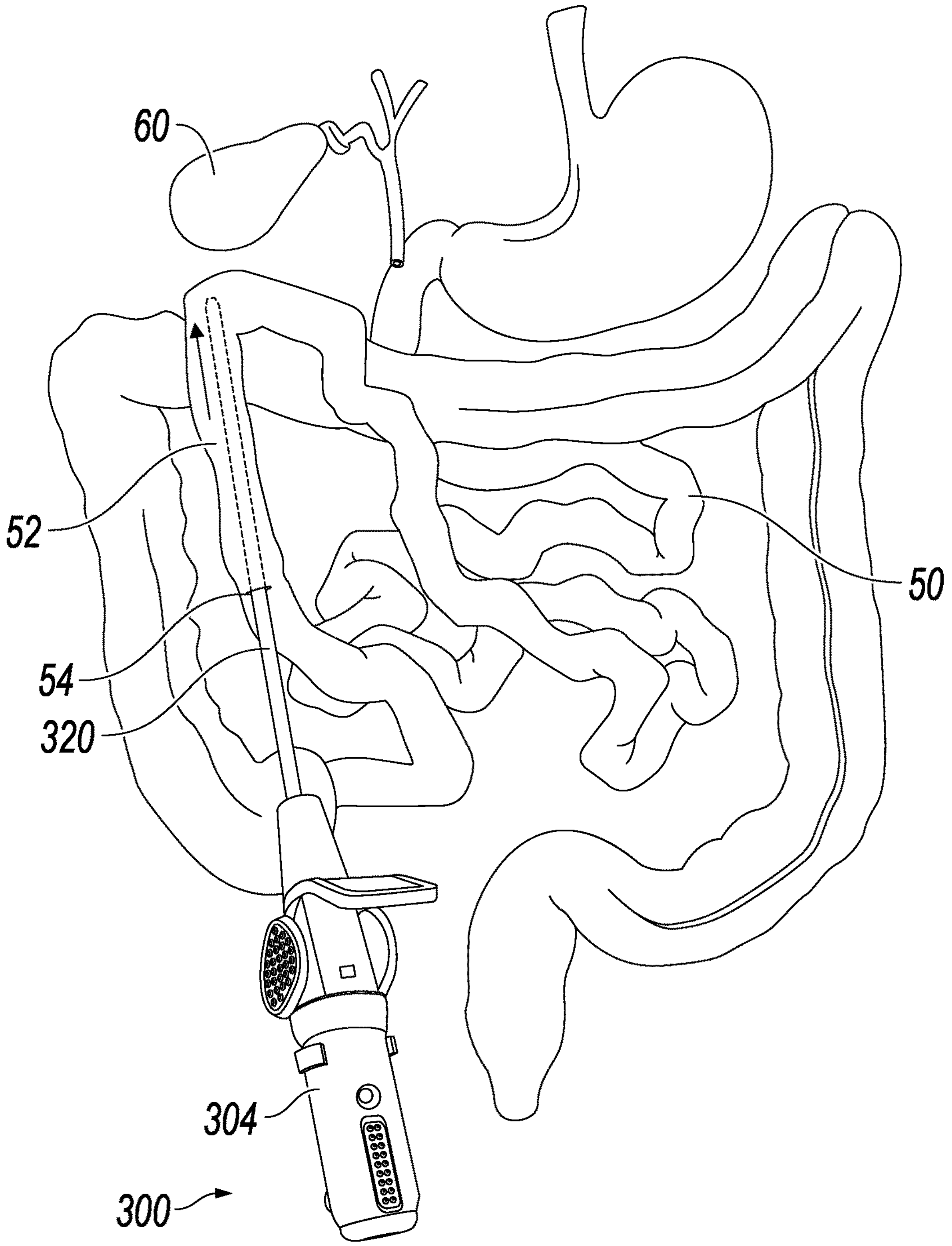
FIG. 57 is a partial front view of the digestion system of FIG. 56 with an anastomotic coupler being inserted through an incision into the ileum and toward the gall bladder.
Figure 58:
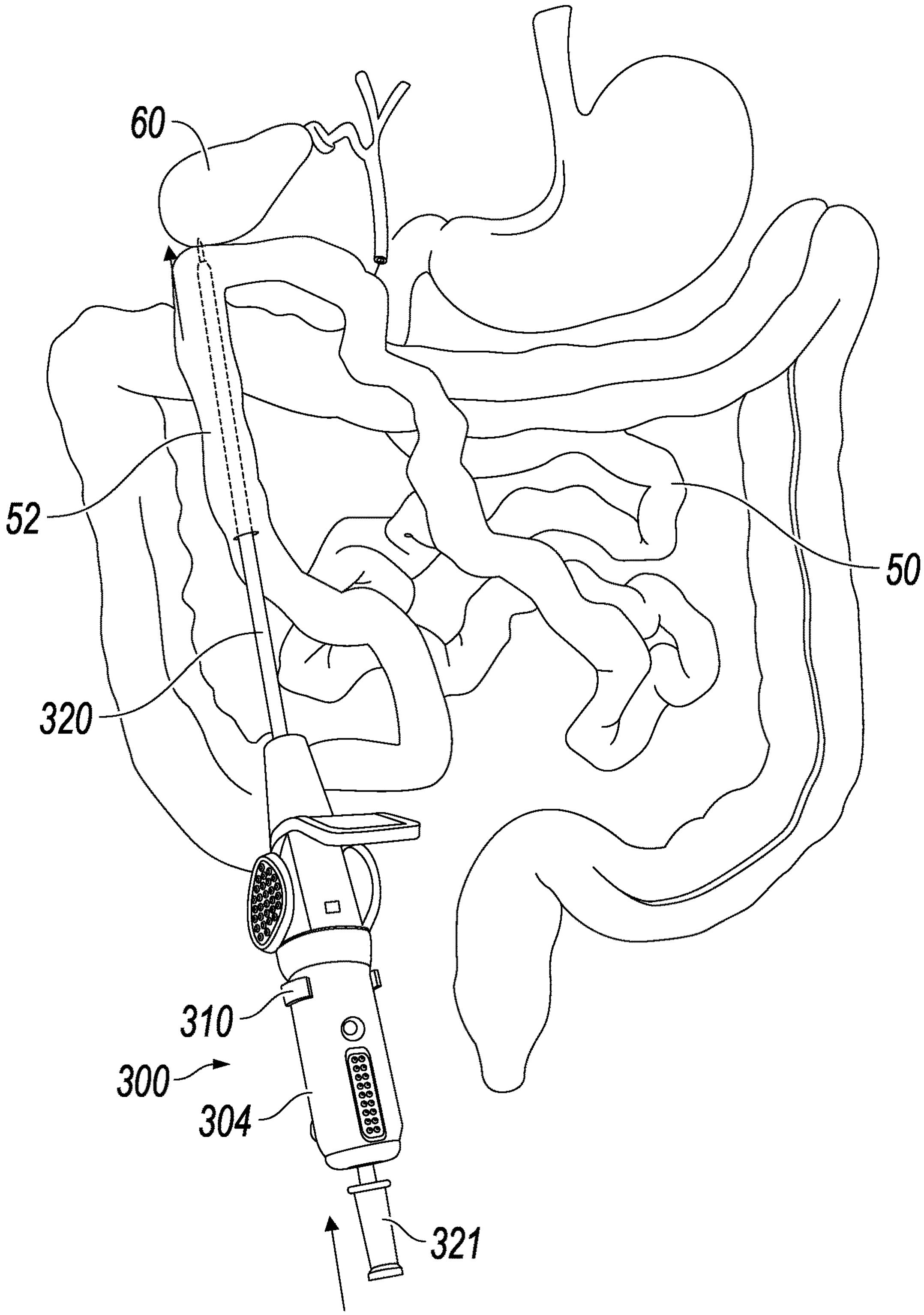
FIG. 58 is a partial front view of the digestion system of FIG. 56 in which a distal end of the anastomotic coupler is positioned within the ileum and adjacent the gall bladder, while a penetrator is inserted through the anastomotic coupler to incise the ileum and the gall bladder.
Figure 59:
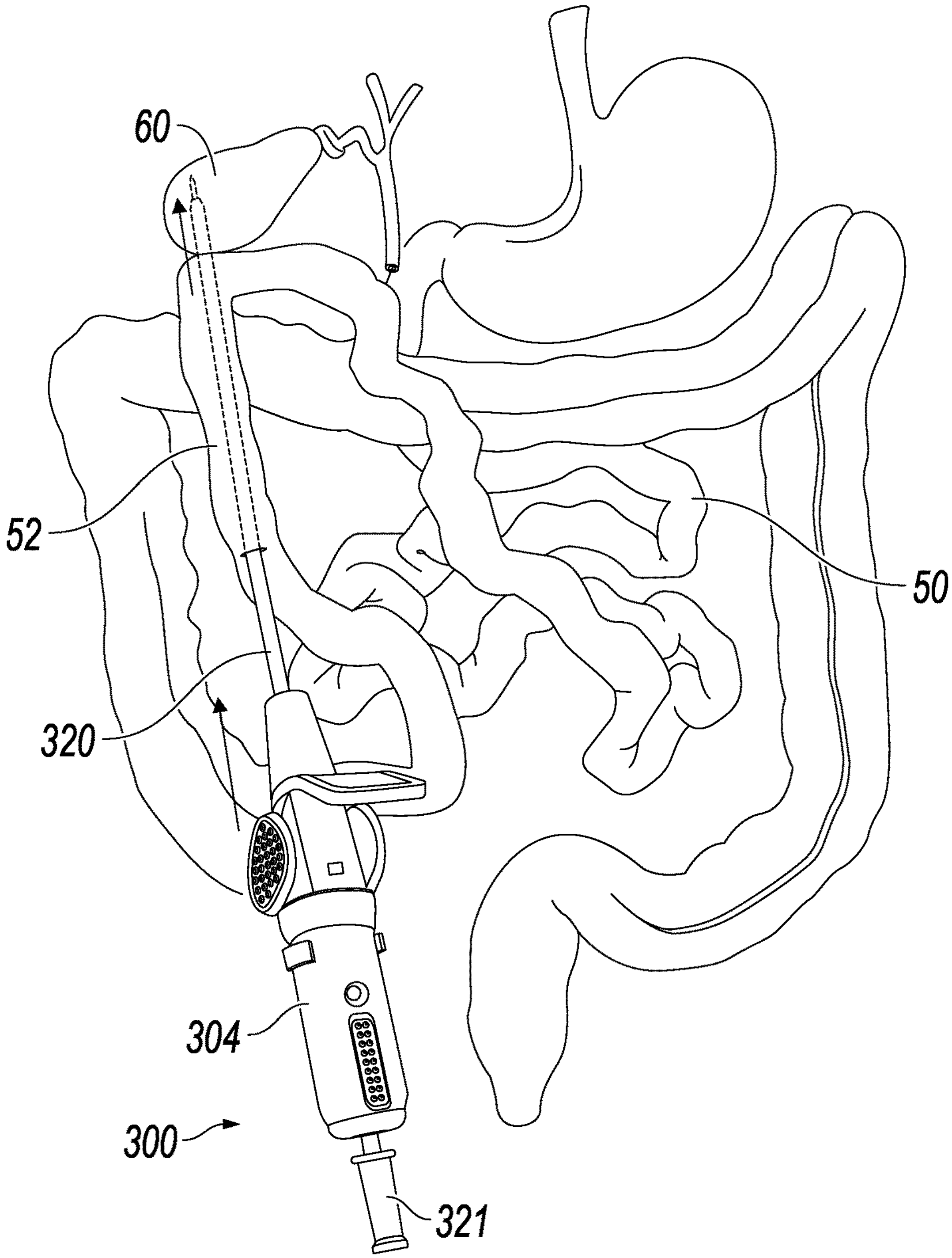
FIG. 59 is a partial front view of the digestion system of FIG. 56 in which the anastomotic coupler is inserted into the gall bladder from the ileum and through the incision created by the penetrator.

To begin the procedure, one or more incisions can be made in a patient to provide access to the patient's small intestine 50 and gall bladder 60. A surgeon can then grab a section of the patient's ileum 52 and bring it to an antecolic or retrocolic position, proximate the gall bladder as seen in FIG. 56. This orientation can then define a distal ileal loop 52D located distal of the ileal region proximate the gall bladder 60, and a proximal ileal loop 52P located proximal of the ileal region proximate the gall bladder 60. Separately, an incision 54 can be made in the ileum 52 distally of the portion grabbed by the surgeon, such as in the form of an antemesenteric enterotomy, and as shown in FIG. 57, an anastomotic coupler 340 fixed to a distal end of a flexible guide tube 320 can be inserted through the incision 54 toward the gall bladder 60. Once inserted, a distal tip 320D of the guide tube 320, distal of the anastomotic coupler 340, can be advanced until it is positioned against the wall of both the ileum 52 and the gall bladder 60.

Once in position, a penetrator 321 (e.g., a cutting needle, a radiofrequency probe, or an equivalent known in the art) can be inserted through the actuator assembly 300 all the way to the distal tip 320D, emerging from a central lumen 322 thereof, to penetrate both the ileum 52 and the gall bladder 60. This penetration can be seen in FIG. 60. After the penetrator 321 penetrates the gall bladder 60, the anastomotic coupler 340 can be advanced into the gall bladder 60. In some embodiments, an introducer sheath (e.g., via introducer sheath 250, not shown) can be inserted into the ileum and then into the gallbladder. Through the introducer sheath, a self-expanding anastomotic coupler (not shown) can be advanced into the gallbladder. The introducer sheath can be retracted and a distal wing of the self-expanding anastomotic coupler can be deployed. The introducer sheath and self-expanding anastomotic coupler can then be further retracted and a proximal wing of the self-expanding anastomotic coupler can be deployed within the ileum.

Figure 60:
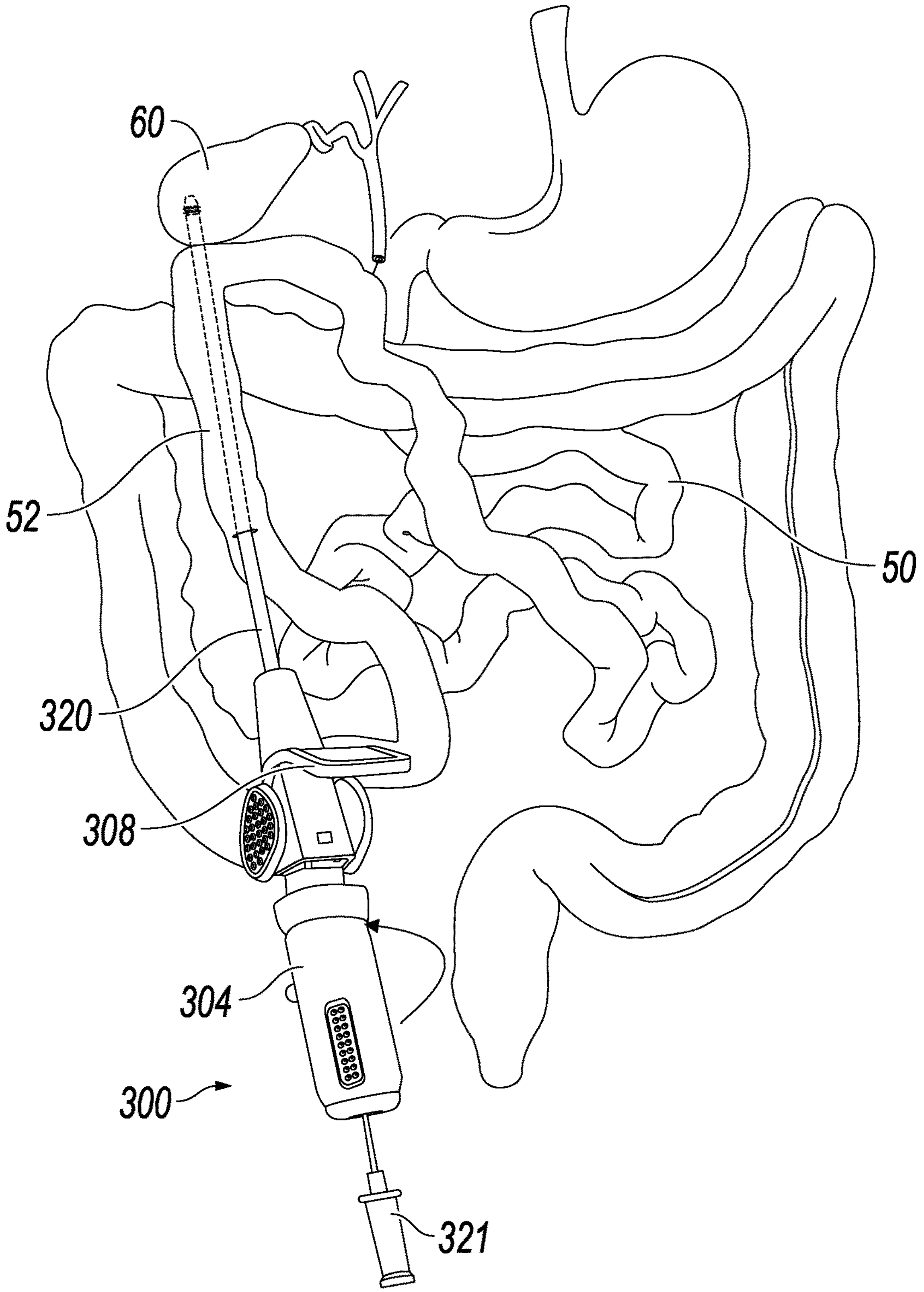
FIG. 60 is a partial front view of the digestion system of FIG. 56 in which a distal wing of an anastomotic coupler coupled to the actuator assembly is transformed into a deployed configuration within the gall bladder.
Figure 61:
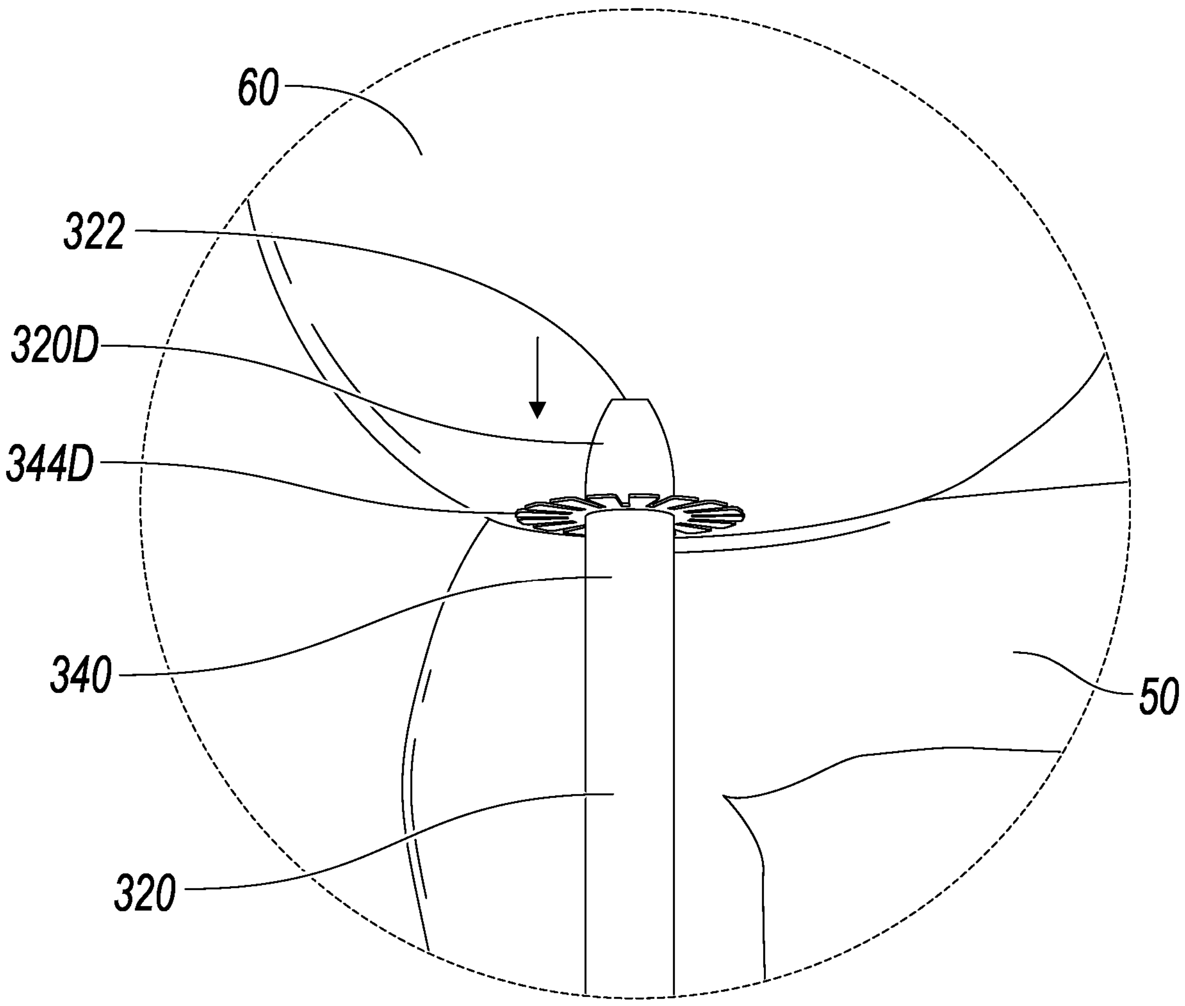
FIG. 61 is a partial front view of the gall bladder and ileum of FIG. 56 showing the closure assembly being retracted to cause the distal wing to contact an inner wall of the gall bladder.
Figure 62:
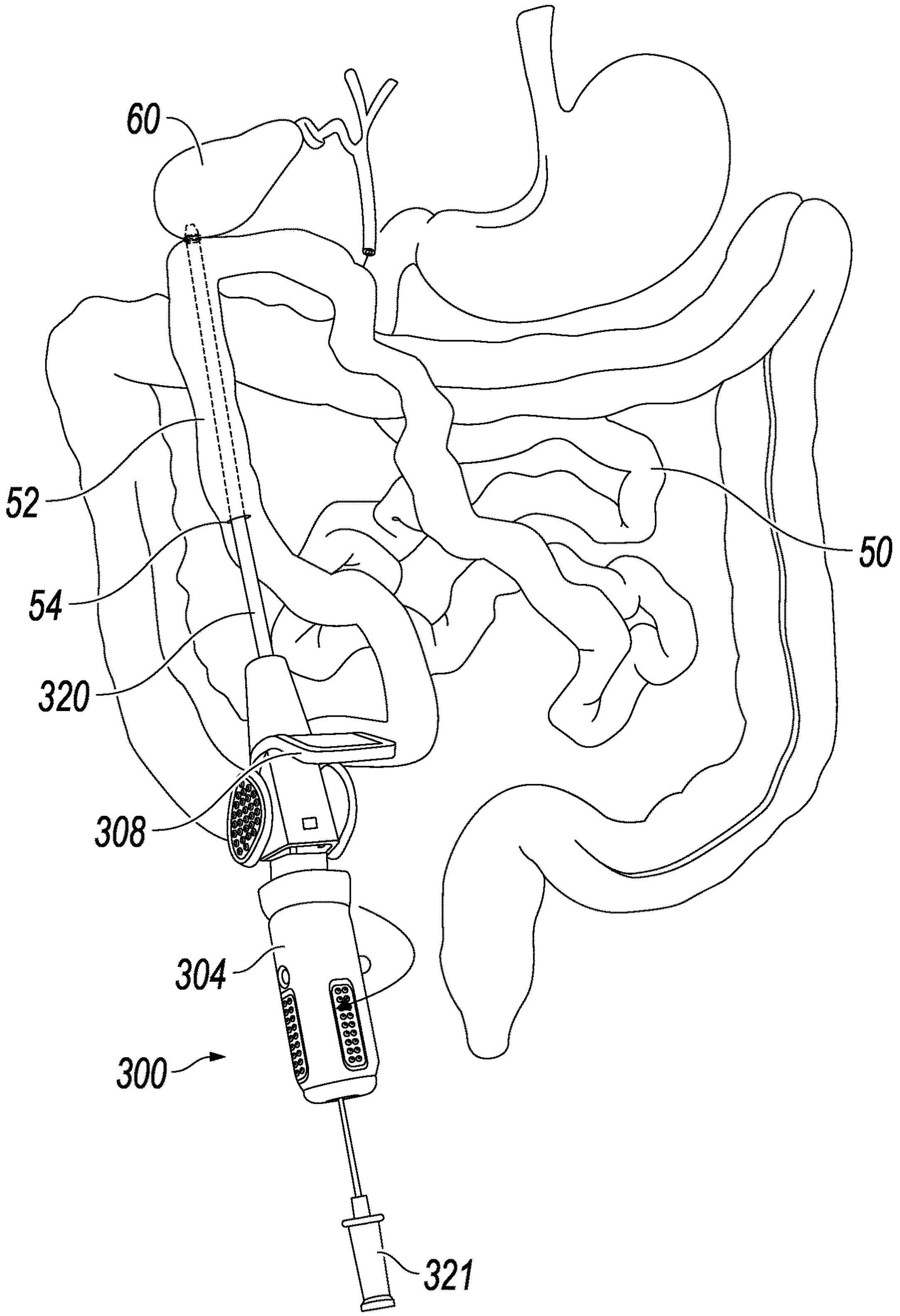
FIG. 62 is a partial front view of the digestion system of FIG. 56 in which a proximal wing of the anastomotic coupler is transformed into a deployed configuration within the ileum.
Figure 63:
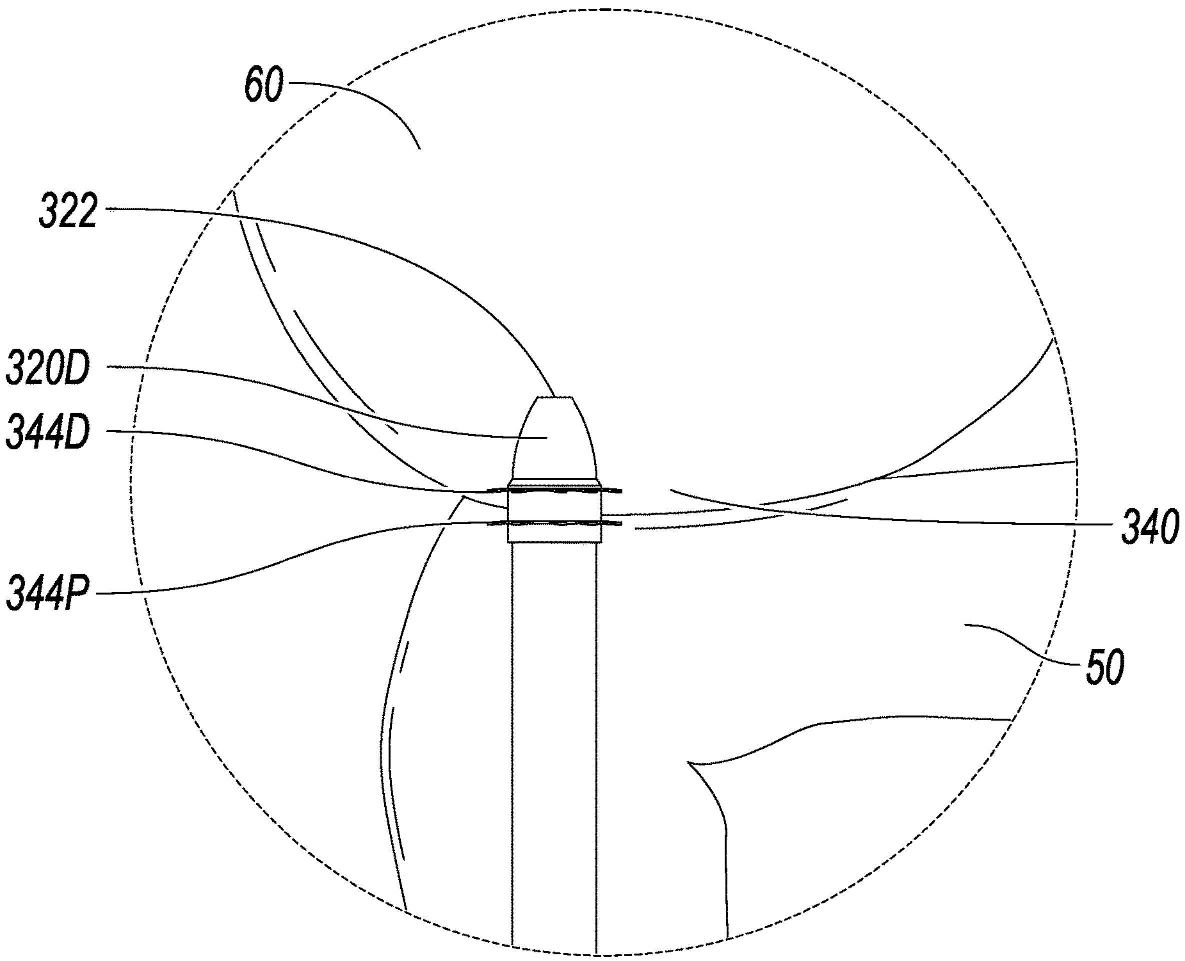
FIG. 63 is a partial front view of the gall bladder and ileum of FIG. 63 showing the walls of the gall bladder and the ileum being captured between the proximal and distal wings of the anastomotic coupler.
Figure 64:
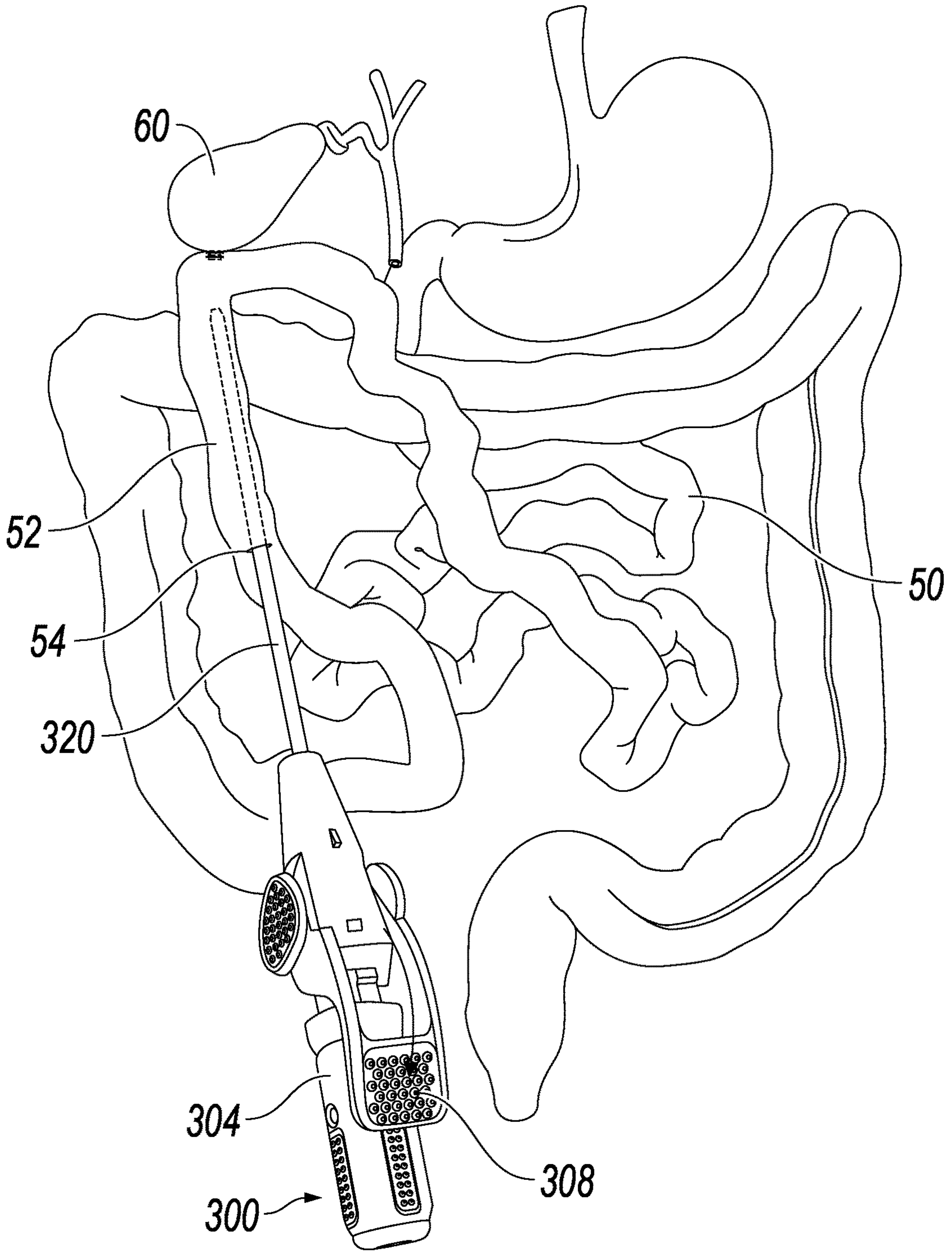
FIG. 64 is a partial front view of the digestion system of FIG. 56 in which the anastomotic coupler is deployed and an actuator assembly of the closure assembly is being retracted from the ileum.
Figure 65:
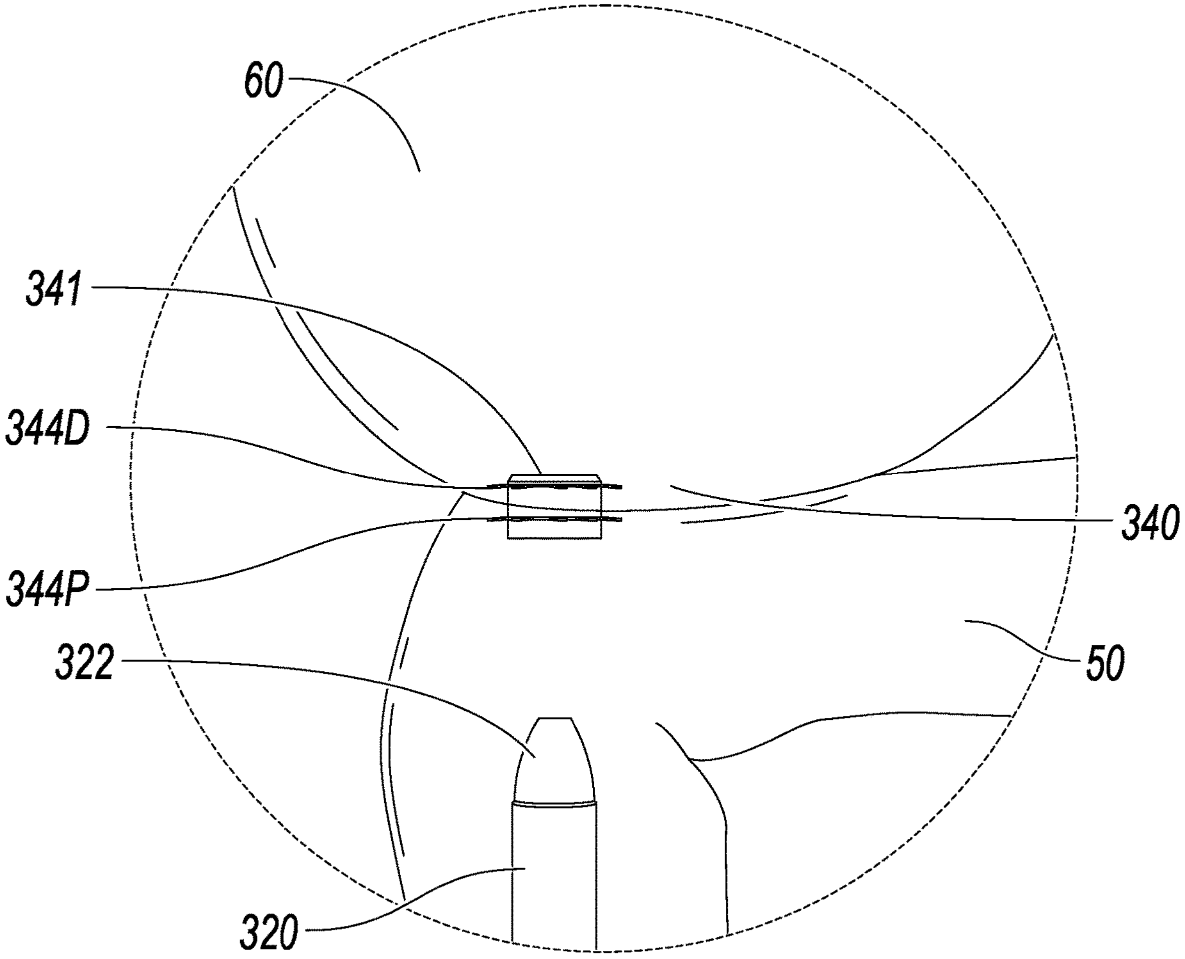
FIG. 65 is a partial front view of gall bladder and the ileum of FIG. 56 in which the anastomotic coupler is deployed and separate from the actuator assembly.

Following successful penetration and advancement of the coupler 340 into the gall bladder 60, the penetrator 321 can be partially retracted from the gall bladder 60 in preparation for deployment of the anastomotic coupler 340. A locking tab 310, which prevents premature deployment of the anastomotic coupler 340, can be removed from the actuator assembly 300. With the locking tab 310 removed, a handle 304 on the actuator assembly 300 can be actuated, such as, for example, with a clockwise turn to deploy a distal wing 344D of the coupler 340 within the gall bladder 60, as seen in FIGS. 60-61. Once the distal wing 344D is deployed, the actuator assembly 300 can be pulled proximally so that the distal wing 344D contacts an interior of the gall bladder 60, seen in FIG. 61. From there, a proximal wing 344P of the anastomotic coupler 340 can be deployed through actuation of the handle 304, such as, for example, with a counter-clockwise turn, as seen in FIGS. 62-63, thereby joining the gall bladder 60 and the ileum 52 together. In some embodiments, deployment of the proximal and distal wings 344P, 344D can be reversed, such that the proximal wings 344P are first deployed in the ileum and the distal wings 344D are next deployed in the gallbladder.

Following deployment of the proximal wing 344P, the penetrator 321 can be fully removed from the actuator assembly 300. Then, a dye, such as methylene blue or similar, can be injected through the same lumen 322 through which the penetrator 321 was inserted in order to check for leakage of the anastomosis. If a leak is detected, either one or both of the proximal and distal wings 344P, 344D of the anastomotic coupler 340 can be re-actuated to partially return to a pre-deployment state, and the anastomotic coupler 340 can be re-deployed in a more suitable position. If necessary, the actuator assembly 300 can be removed prior to redeployment, in order to address any additional challenges causing an improper joinder of the ileum and gall bladder 60.

If the joinder is a success, an ejection lever 308 located on the actuator assembly 300 can be actuated in order to eject the anastomotic coupler 340 from the actuator assembly 300. The anastomotic coupler 340 has a central lumen 341, which can cause the gall bladder 60 to be in fluid communication with the ileum 50.

Figure 66:
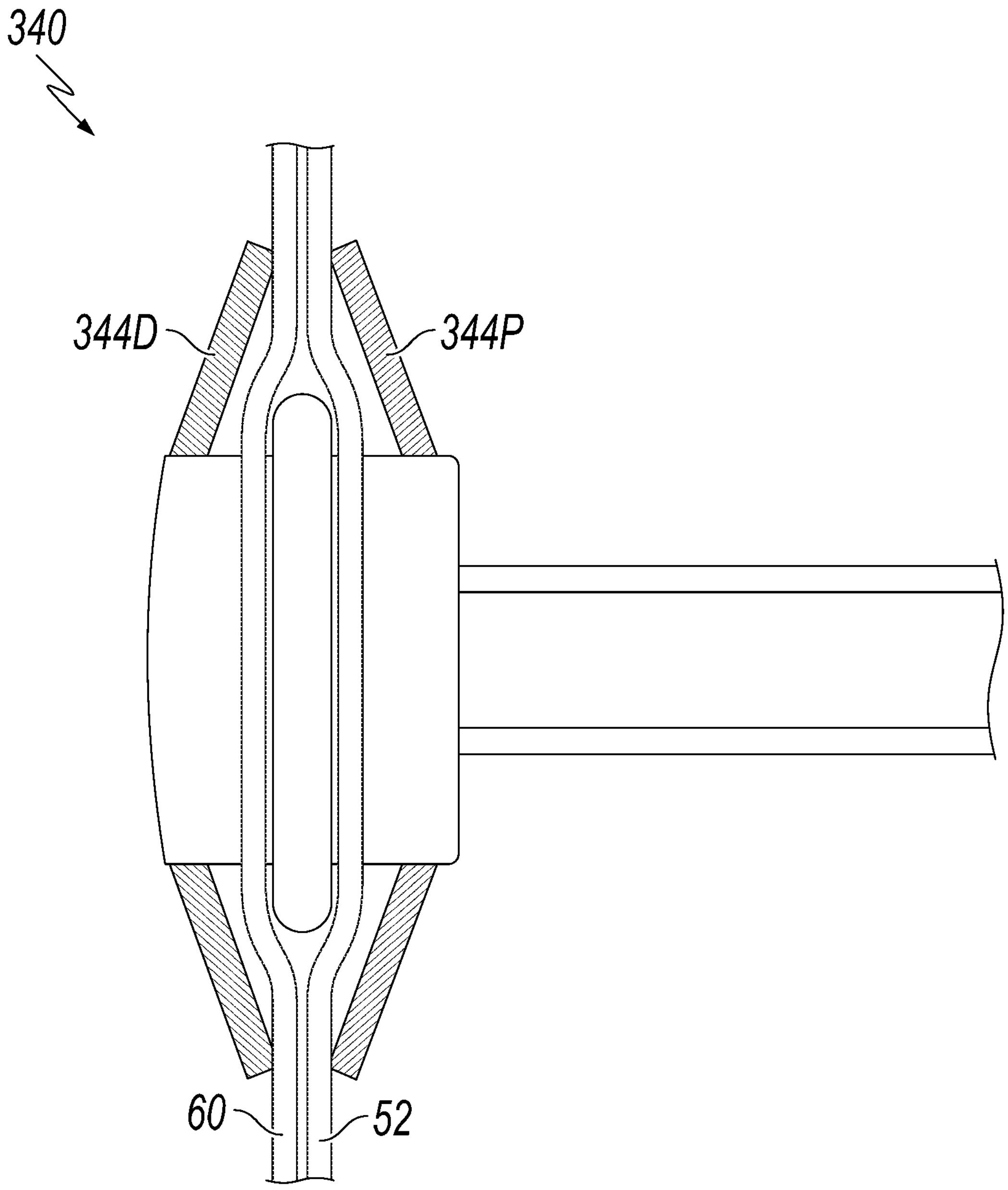
FIG. 66 is a cross-sectional view of the deployed anastomotic coupler of FIG. 65.
Figure 67:
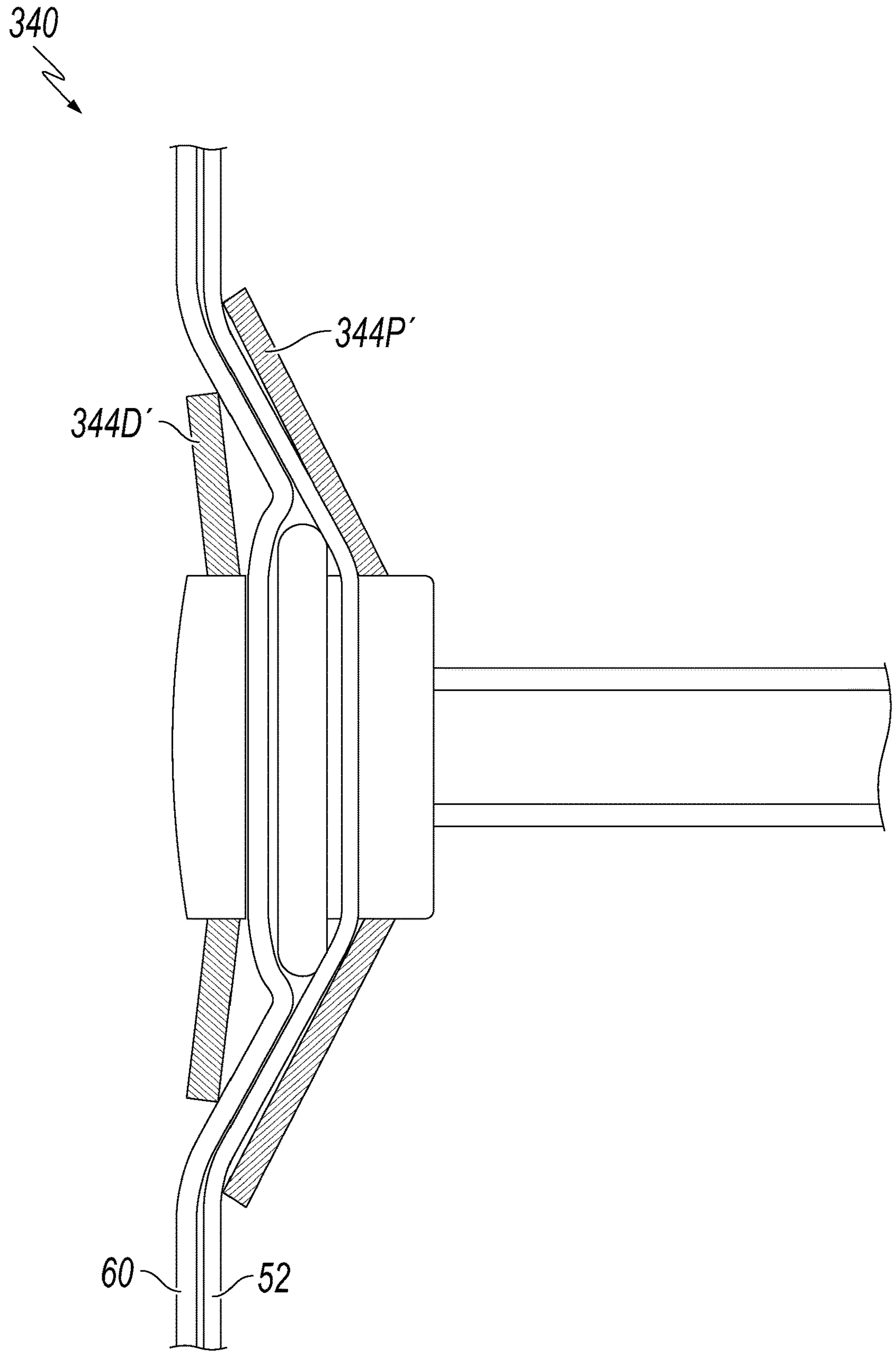
FIG. 67 is a cross-sectional view of a deployed anastomotic coupler, with press ring, having proximal and distal wings with varied lengths and deployment angles, according to another embodiment.

FIGS. 66-67 depict a cross-sectional view of the anastomotic coupler 340 according to certain embodiments. The proximal and distal wings 344P, 344D of the anastomotic coupler 340 can have similar sizes relative to one another for this procedure. Additionally, the proximal and distal wings 344P, 344D of the coupler 340 can be deployed at various angles relative to an axis of the central lumen 341. These angles of deployment can be configured to promote the fusion of the gall bladder 60 and the ileum 52, while simultaneously preventing the pinching of tissue, which could lead to serious complications such as necrosis and infection. For example, in FIG. 66, the proximal wing 344P is deployed at an angle such that radial ends of the proximal wing 344P pass over a middle of the anastomotic coupler 340, and the length of the proximal wing 344P is much greater than the length of the distal wing 344D. This causes the walls of the gall bladder 60 and the ileum 52 to strain, potentially risking damage. In contrast, FIG. 67 illustrates an embodiment of an anastomotic coupler 340 in which both the proximal and distal wings 344P, 344D are similar in length, and their respective angles of deployment are not severe enough as to strain the walls of the gall bladder 60 and the ileum 52.

In some embodiments the wings 344P, 344D can be made to touch each other (such as by increasing the lengths and/or by altering deployment angles thereof), thereby contributing to the creation of a compressive anastomosis, which can result in tissue necrosis. During a healing process of such a necrosis, the outer walls of the ileum and the gallbladder can fuse to each other. The anastomotic coupler 340 can slough off and pass distally through the ileum to be expelled from the patient and leaving a temporary or permanent fluid path therebetween.

After ejection of the anastomotic coupler 340, the actuator assembly 300 can be removed entirely from the patient.

Figure 68:
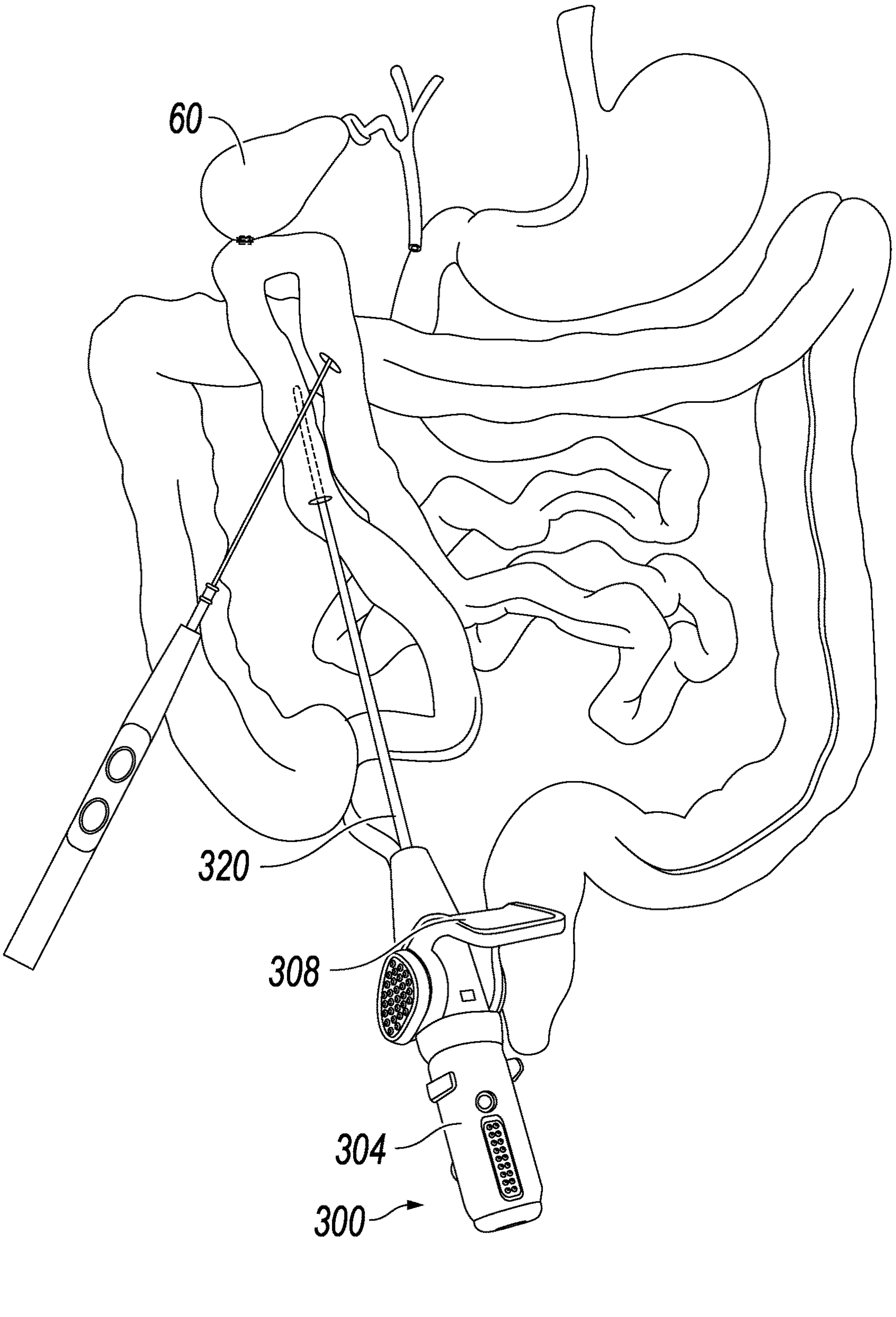
FIG. 68 is a partial front view of the digestion system of FIG. 56 in which an actuator assembly is inserted into the first incision and toward a second incision made in a proximal ileal loop.

From there, the entero-entero anastomosis can be performed, as shown in FIGS. 68-72. To start, a second anastomotic coupler 340' can be delivered by the actuator assembly 300 into the ileum 52 via the incision 54, as shown in FIG. 68. Using a gripping mechanism 70 (e.g., forceps and the like, not shown), a proximal ileal loop 52P can be maneuvered into position proximal to the distal ileal loop 52D. Once the proximal ileal loop 52P is in position, a second incision 55 can be made in the proximal ileal loop 52P in a manner similar to the process for making the incision 54, e.g., a 5 mm enterotomy.

Figure 69:
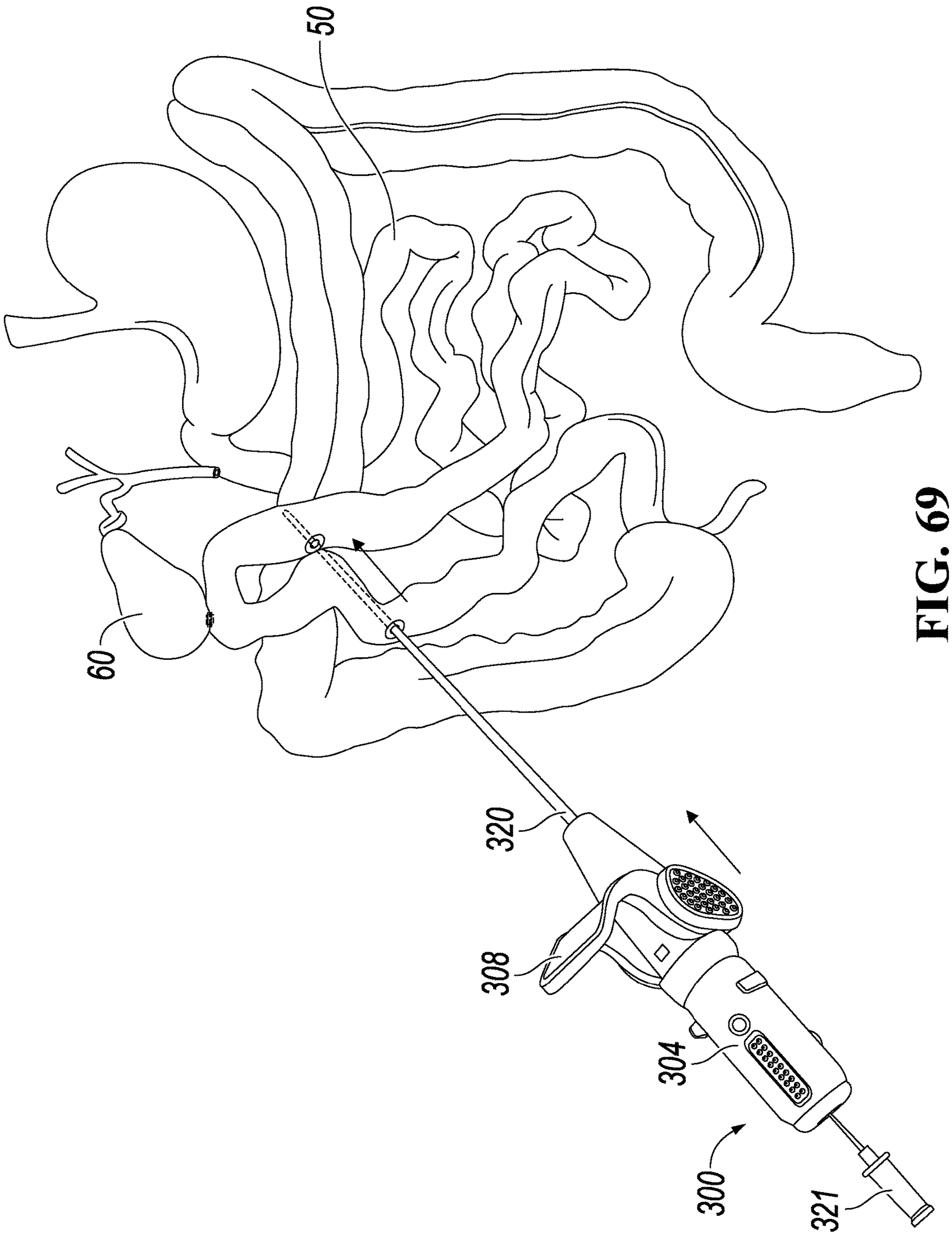
FIG. 69 is a partial front view of the digestion system of FIG. 56 in which a penetrator is inserted through the actuator assembly to pierce through an inner wall of a distal ileal loop and into the second incision.

The actuator assembly 300 can then be oriented as shown in to contact a portion of the ileum 52 while aligning the contacted portion with the second incision 55. Once aligned, the penetrator 321 can be inserted through the actuator assembly 300, as described above, and an incision can be made in the distal ileal loop proximate the second incision 55. The anastomotic coupler 340' can then be inserted, joining both ileal loops 52D, 52P, and the penetrator 321 can be partially withdrawn, as seen in FIG. 69.

Figure 70:
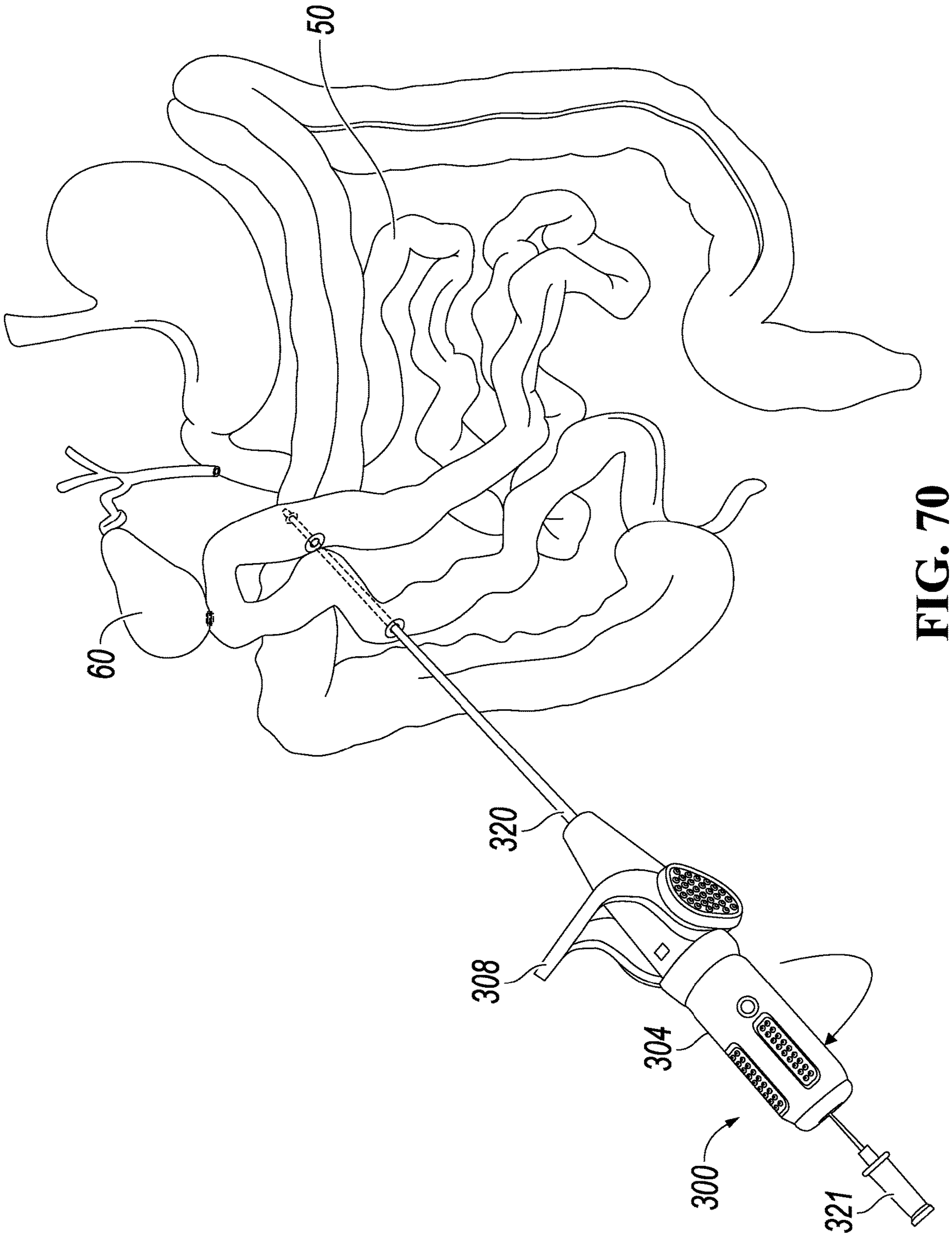
FIG. 70 is a partial front view of the digestion system of FIG. 56 in which a distal wing of a second anastomotic coupler is transformed from a delivery configuration to a deployed configuration within the proximal ileal loop.
Figure 71:
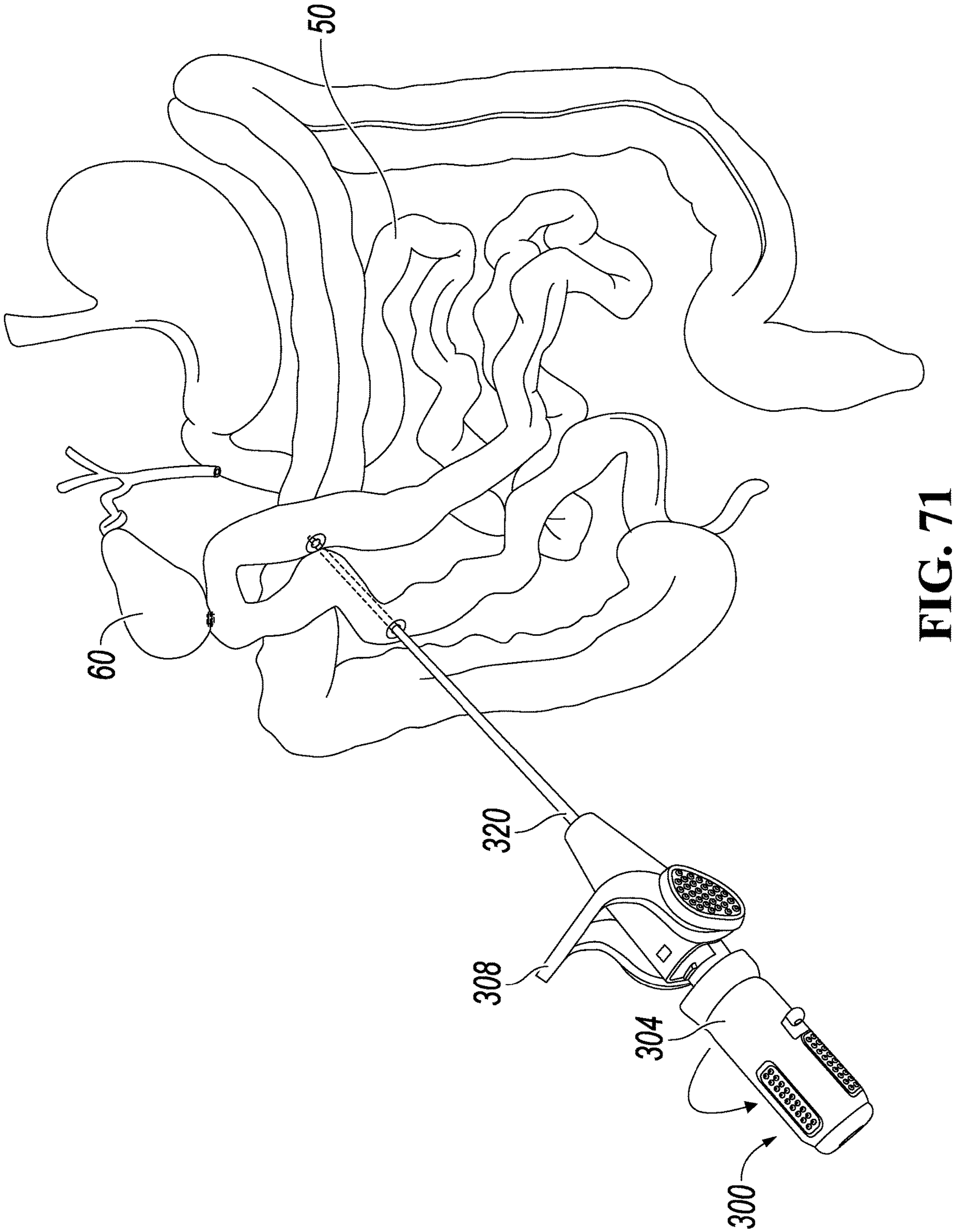
FIG. 71 is a partial front view of the digestion system of FIG. 56 in which a proximal wing of the second anastomotic coupler is transformed from a delivery configuration to a deployed configuration within the distal ileal loop, thereby joining the proximal and distal ileal loops.

Following that, the anastomotic coupler 340' can be deployed in a similar manner as described above. As shown in FIGS. 70-71, a locking tab 310 can be removed, and the handle 304 can be actuated (such as through clockwise rotation) to cause a distal wing 344D to be deployed within the proximal ileal loop 52P. Then, the actuator assembly 300 can be withdrawn to cause the distal wing 344D to contact an inner wall of the distal ileal loop 52D. Once in position, the handle 304 can be actuated again (such as through counter-clockwise rotation) to cause a proximal wing 344P of the anastomotic coupler 340' be deployed within the distal ileal loop 52D, thereby joining the proximal ileal loop 52P and the distal ileal loop 52D together.

The joinder can be checked using a process similar to the one described previously using methylene blue. From there, the lever 308 of the actuator assembly 300 can be actuated to cause the actuator assembly 300 and the anastomotic coupler 340' to separate. The actuator assembly 300 can then be withdrawn from the patient, and the various incisions made during the procedure can be closed.

Figure 72:
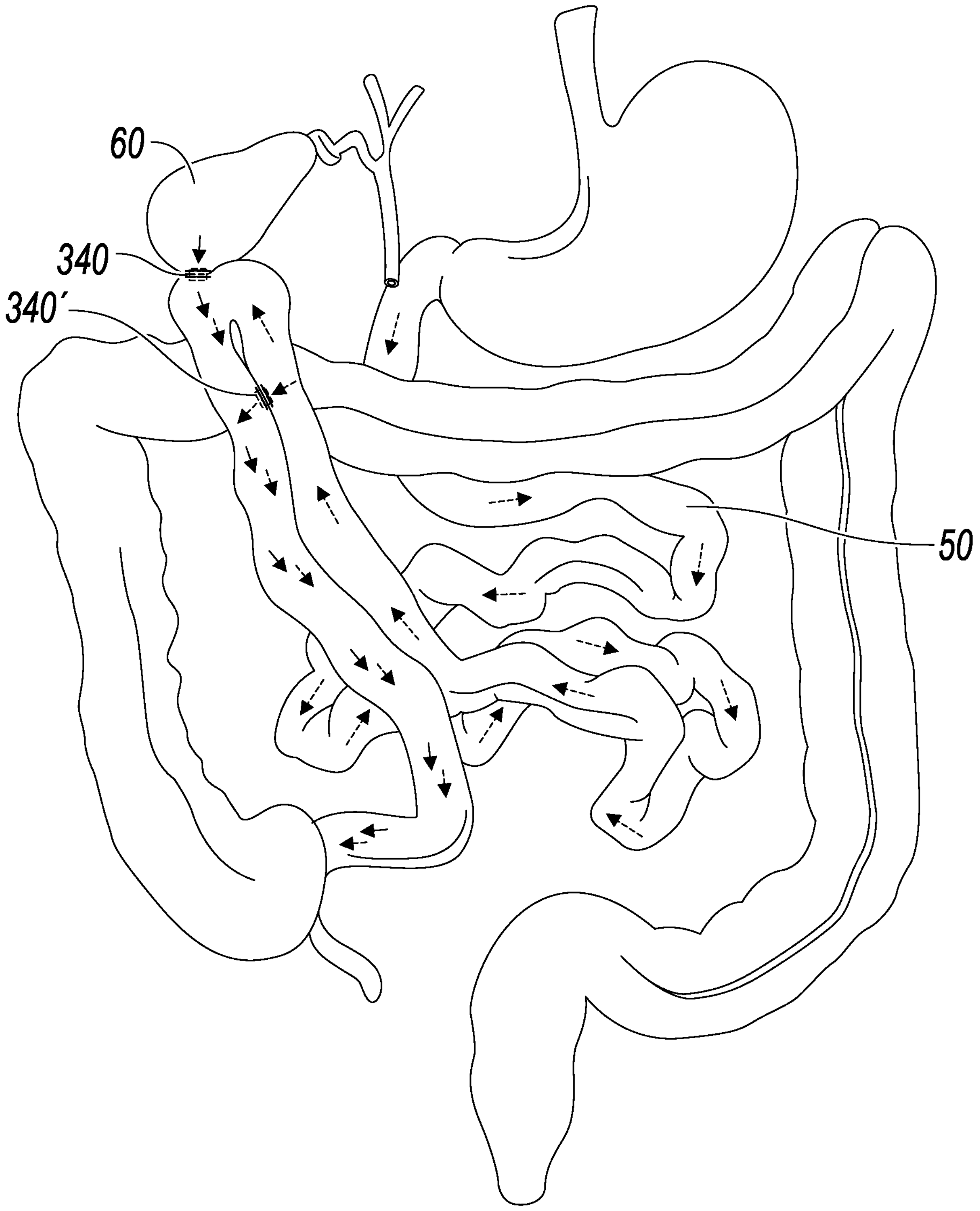
FIG. 72 is a partial front view of the digestion system of FIG. 56 showing a first flow path from the gall bladder through deployed anastomotic coupler and a second flow path from the proximal ileal loop to the distal ileal loop through the deployed second anastomotic coupler.

FIG. 72 depicts the newly created fluid pathways for bile following this medical procedure. Fluid can proceed to flow from the gall bladder 60 and into the small intestine 50 as normal, as well as to flow through each of the anastomotic couplers 340, 340'.

Certain illustrative implementations have been described to provide an overall understanding of the principles of the structure, function, manufacture, and use of the systems, devices, and methods disclosed herein. One or more examples of these implementations have been illustrated in the accompanying drawings. Those skilled in the art will understand that the systems, devices, and methods specifically described herein and illustrated in the accompanying drawings are non-limiting illustrative implementations and that the scope of the present invention is defined solely by the claims. The features illustrated or described in connection with one illustrative implementation may be combined with the features of other implementations. Such modifications and variations are intended to be included within the scope of the present invention. Further, in the present disclosure, like-named components of the implementations generally have similar features, and thus within a particular implementation each feature of each like-named component is not necessarily fully elaborated upon.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

One skilled in the art will appreciate further features and advantages of the invention based on the above-described implementations. Accordingly, the present application is not to be limited by what has been particularly shown and described, except as indicated by the appended claims. All publications and references cited herein are expressly incorporated by reference in their entirety.

What is claimed is:

1. A surgical method, comprising:
- advancing a first coupler through a small intestine to a region of the small intestine proximate a gallbladder, the first coupler being coupled to a distal end of an elongate shaft;
- piercing the region of the small intestine and the gallbladder using a penetrator advanced through the elongate shaft and the first coupler;
- advancing the first coupler at least partially within the gallbladder;
- deploying, via a rotational force applied to the first coupler, a first distal wing of the first coupler within the gallbladder;
- retracting the elongate shaft to cause the first distal wing to contact an inner surface of the gallbladder;
- deploying, via a rotational force applied to the first coupler, a first proximal wing of the first coupler within the small intestine to removably affix the first coupler to the gallbladder and the small intestine; and
- ejecting the first coupler from the distal end of the elongate shaft.

2. The method of claim 1, further comprising:
- advancing a second coupler through the small intestine into an ileal loop that is distal to a proximal ileal loop, the second coupler being coupled to the distal end of the elongate shaft;
- piercing through an inner wall of the distal ileal loop to enter the proximal ileal loop using the penetrator advanced through the elongate shaft and the second coupler;
- deploying a second distal wing of the second coupler within the proximal ileal loop;
- retracting the elongate shaft to cause the second distal wing to contact an inner surface of the proximal ileal loop;
- deploying a second proximal wing of the second coupler within the distal ileal loop to removably affix the second coupler to the proximal ileal loop and the distal ileal loop; and
- ejecting the second coupler from the distal end of the elongate shaft.

3. The method of claim 2, wherein at least one of the first proximal wing and the first distal wing deploys at an acute angle relative to a longitudinal axis of the elongate shaft.

4. The method of claim 3, wherein the other of the first proximal wing and the first distal wing deploys at an acute angle relative to a longitudinal axis of the elongate shaft.

5. The method of claim 3, wherein a radial tip of the first proximal wing, in a deployed configuration, contacts an inner wall of the small intestine and a radial tip of the first distal wing, in a deployed configuration, contacts an inner wall of the gallbladder.

6. The method of claim 1, wherein an angle of deployment of the first proximal wing and an angle of deployment of the first distal wing are substantially equal, and wherein a length of the first proximal wing and a length of the first distal wing are substantially equal.

7. The method of claim 1, wherein the first proximal wing comprises a first plurality of petals and the first distal wing comprises a second plurality of petals, and wherein the first plurality of petals is rotatably offset from the second plurality of petals.

8. A method, comprising:
- deploying, via an actuator tool having an elongate shaft and a first coupler coupled to a distal end of the elongate shaft, a first distal wing of the first coupler within a gallbladder and first proximal wing of the first coupler within an ileum;
- deploying, via the actuator tool having a second coupler coupled to the distal end, a second distal wing of the second coupler within a first loop of the ileum distal to the deployed first coupler, and a second proximal wing of the second coupler within a second loop of the ileum proximal to the deployed first coupler;
- wherein the first coupler defines a first central lumen configured to fluidly join the gallbladder and the ileum therethrough; and
- wherein the second coupler defines a second central lumen configured to fluidly join the first and second loops therethrough.

9. The method of claim 8, further comprising:
- piercing through a wall of the ileum and through a wall of the gall bladder with a penetrator coupled to the distal end of the elongate shaft to position the first coupler at least partially within the gallbladder and at least partially within the ileum.

10. The method of claim 9, wherein at least one of the first proximal wing and the first distal wing deploys at an acute angle relative to a longitudinal axis of the elongate shaft.

11. The method of claim 10, wherein the other of the first proximal wing and the first distal wing deploys at an acute angle relative to a longitudinal axis of the elongate shaft.

12. The method of claim 10, wherein a radial tip of the first proximal wing, in a deployed configuration, contacts an inner wall of the small intestine in and a radial tip of the first distal wing, in a deployed configuration, contacts an inner wall of the gallbladder.

13. The method of claim 9, wherein the angle of deployment of the first proximal wing and the angle of deployment of the first distal wing are substantially equal, and wherein the length of the first proximal wing and the length of the first distal wing are substantially equal.

14. The method of claim 9, wherein the first proximal wing comprise a first plurality of petals and the first distal wing comprise a second plurality of petals, and wherein the first plurality of petals is rotatably offset from the second plurality of petals.

15. A method comprising:
introducing a first coupler into an ileum, the first coupler being attached to an elongate shaft extending distally from an actuator tool, the first coupler and the elongate shaft defining a first central lumen therethrough;
contacting an outer wall of the ileum adjacent an outer wall of a gallbladder with a distal end of the first coupler;
extending a first penetrator through the first central lumen to pierce the inner wall of the ileum and the outer wall of the gallbladder;
advancing the first coupler from the ileum and into the gallbladder;
deploying, through a first rotational force applied by the actuator tool, a distal wing of the first coupler within the gallbladder;
retracting the first coupler to contact an inner wall of the gallbladder with the distal wing;
deploying, through a second rotational force applied by the actuator tool, a proximal wing of the first coupler within the ileum, the gallbladder and the ileum being in fluid communication via the first coupler; and
de-coupling the first coupler from the elongate shaft.

16. The method of claim 15, further comprising:
introducing a second coupler into a distal ileal loop distal of the first coupler, the second coupler being attached to the elongate shaft, the second coupler and the elongate shaft defining a second central lumen therethrough;
incising a region of a proximal ileal loop proximal of the first coupler;
contacting an outer wall of the distal ileal loop adjacent the incised region of the proximal ileal loop;
extending a second penetrator through the second central lumen to pierce the inner wall of the distal ileal loop and the incised region;
advancing the second coupler from the distal ileal loop into the proximal ileal loop through the incised region;
deploying, with the actuator tool, a distal wing of the second coupler within the proximal ileal loop;
retracting the second coupler to contact an inner wall of the proximal ileal loop with the distal wing;
deploying, with the actuator tool, a proximal wing of the second coupler within the distal ileal loop, the proximal and distal ileal loops being in fluid communication via the second coupler; and
de-coupling the second coupler from the elongate shaft.

17. A method, comprising:
inserting a sheath through an ileum and into a gallbladder;
advancing an expandable coupler coupled to a distal end of an actuator tool through the sheath and into the gallbladder;
retracting the sheath from the gallbladder to expose the expandable coupler;
deploying, through a first rotational force applied by the actuator tool, a distal wing of the expandable coupler within the gallbladder;
deploying, through a second rotational force applied by the actuator tool, a proximal wing of the expandable coupler within the ileum, the gallbladder and the ileum being in fluid communication via the deployed expandable coupler; and
de-coupling the expandable coupler from the actuator tool.

* * * * *